United States Patent
Cutrale et al.

(10) Patent No.: US 10,803,558 B2
(45) Date of Patent: Oct. 13, 2020

(54) HYPERSPECTRAL IMAGING SYSTEM

(71) Applicant: University of Southern California, Los Angeles, CA (US)

(72) Inventors: Francesco Cutrale, San Gabriel, CA (US); Scott E. Fraser, Glendale, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 17 days.

(21) Appl. No.: 16/348,102

(22) PCT Filed: Nov. 7, 2017

(86) PCT No.: PCT/US2017/060462
§ 371 (c)(1),
(2) Date: May 7, 2019

(87) PCT Pub. No.: WO2018/089383
PCT Pub. Date: May 17, 2018

(65) Prior Publication Data
US 2019/0287222 A1  Sep. 19, 2019

Related U.S. Application Data

(60) Provisional application No. 62/419,075, filed on Nov. 8, 2016.

(51) Int. Cl.
*G06K 9/00* (2006.01)
*G06T 5/00* (2006.01)
(Continued)

(52) U.S. Cl.
CPC ............ *G06T 5/002* (2013.01); *A61B 5/0075* (2013.01); *G01J 3/00* (2013.01); *G01J 3/2823* (2013.01);
(Continued)

(58) Field of Classification Search
None
See application file for complete search history.

(56) References Cited

U.S. PATENT DOCUMENTS

| 6,094,050 A | 7/2000 | Zaroubi et al. |
| 2007/0098174 A1 | 5/2007 | Trifonov et al. |

(Continued)

FOREIGN PATENT DOCUMENTS

WO  2006126154 A1  11/2006

OTHER PUBLICATIONS

Fereidouni et al., "Spectral phasor analysis allows rapid and reliable unmixing of fluorescence microscopy spectral images", Optics Express. vol. 20 No. 12, pp. 12729-12741, dated Jun. 4, 2012. [retrieved on Dec. 19, 2017]. Available at: https://www.osapublishing.org/DirectPDFAccess/EDEECFB7-9659-A5BB-59B160AFBE2772D8_233521/oe-20-12-12729.pdf, 13 pages.
(Continued)

*Primary Examiner* — Atiba O Fitzpatrick
(74) *Attorney, Agent, or Firm* — McDermott Will & Emery LLP

(57) ABSTRACT

This invention relates to a hyperspectral imaging system for denoising and/or color unmixing multiple overlapping spectra in a low signal-to-noise regime with a fast analysis time. This system may be configured to carry out Hyper-Spectral Phasors (HySP) calculations to effectively analyze hyperspectral time-lapse data. For example, this system may be configured to carry out Hyper-Spectral Phasors (HySP) calculations to effectively analyze five-dimensional (5D) hyper-spectral time-lapse data. Advantages of this imaging system may include: (a) fast computational speed, (b) the ease of phasor analysis, and (c) a denoising algorithm to obtain the minimally-acceptable signal-to-noise ratio (SNR). An unmixed color image of a target may be gener-
(Continued)

ated. These images may be used in diagnosis of a health condition, which may enhance a patient's clinical outcome and evolution of the patient's health.

69 Claims, 46 Drawing Sheets

(51) Int. Cl.
| | |
|---|---|
| *G01J 3/28* | (2006.01) |
| *G01J 3/44* | (2006.01) |
| *G01N 21/64* | (2006.01) |
| *G02B 21/08* | (2006.01) |
| *G02B 21/16* | (2006.01) |
| *G02B 21/36* | (2006.01) |
| *G06T 5/10* | (2006.01) |
| *H04N 5/33* | (2006.01) |
| *H04N 9/68* | (2006.01) |
| *G01J 3/00* | (2006.01) |
| *A61B 5/00* | (2006.01) |
| *G02B 21/00* | (2006.01) |

(52) U.S. Cl.
CPC ........ *G01J 3/4406* (2013.01); *G01N 21/6458* (2013.01); *G02B 21/00* (2013.01); *G02B 21/08* (2013.01); *G02B 21/16* (2013.01); *G02B 21/36* (2013.01); *G06T 5/10* (2013.01); *H04N 5/332* (2013.01); *H04N 9/68* (2013.01); *G01J 2003/2826* (2013.01); *G06T 2207/10024* (2013.01); *G06T 2207/10036* (2013.01); *G06T 2207/10056* (2013.01); *G06T 2207/10064* (2013.01); *G06T 2207/10152* (2013.01); *G06T 2207/20056* (2013.01); *G06T 2207/30024* (2013.01)

(56) References Cited

U.S. PATENT DOCUMENTS

| | | |
|---|---|---|
| 2012/0276578 A1 | 11/2012 | Stringari et al. |
| 2013/0153770 A1 | 6/2013 | Buffington et al. |
| 2015/0030244 A1 | 1/2015 | Robles-Kelly et al. |
| 2016/0238532 A1* | 8/2016 | Freudiger .......... G01N 21/6402 |

OTHER PUBLICATIONS

International Search Report and Written Opinion from PCT Application No. PCT/US2017/060462 dated Jan. 18, 2018, 18 pages.

* cited by examiner

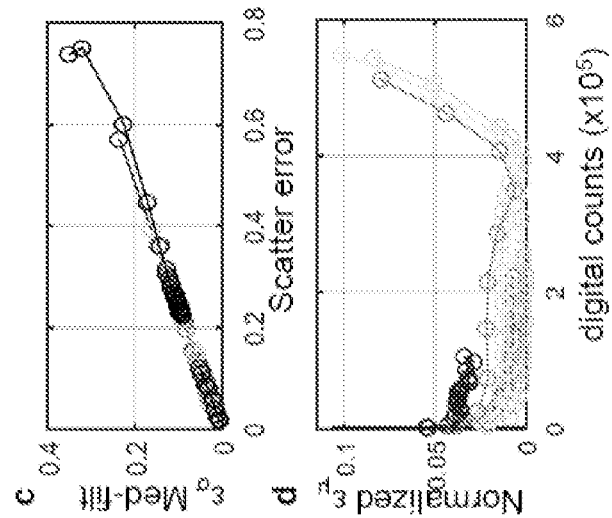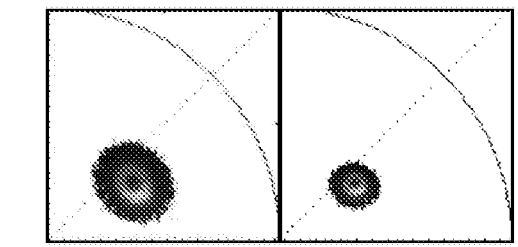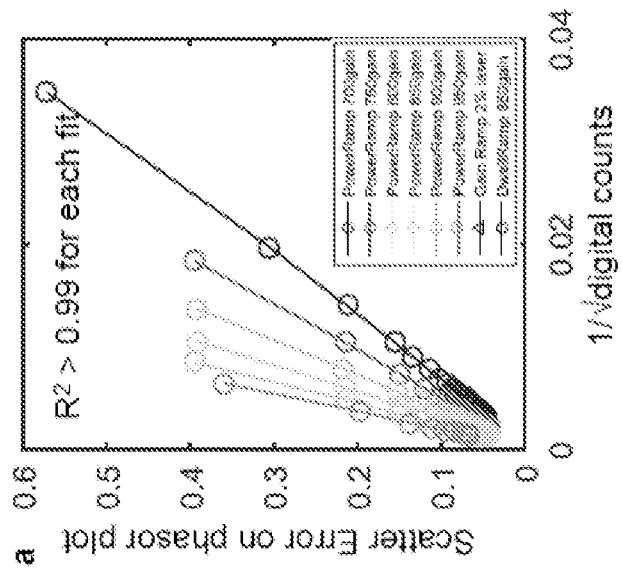

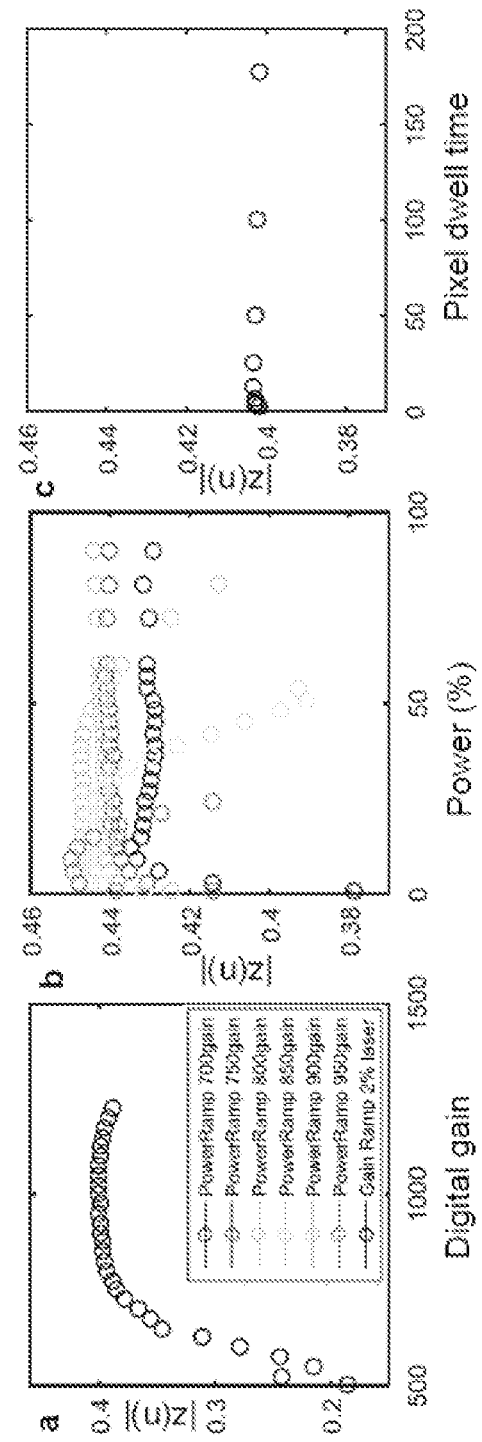

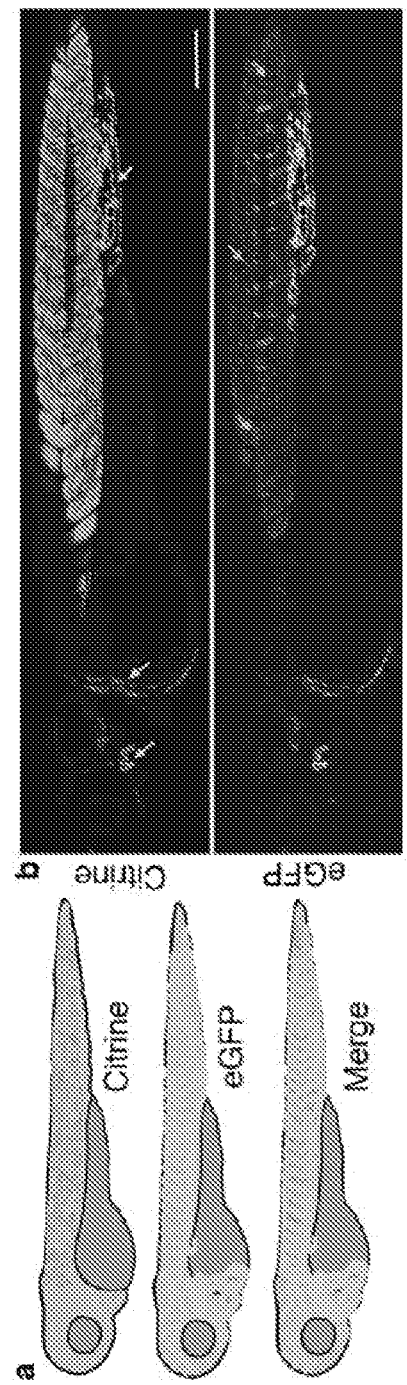

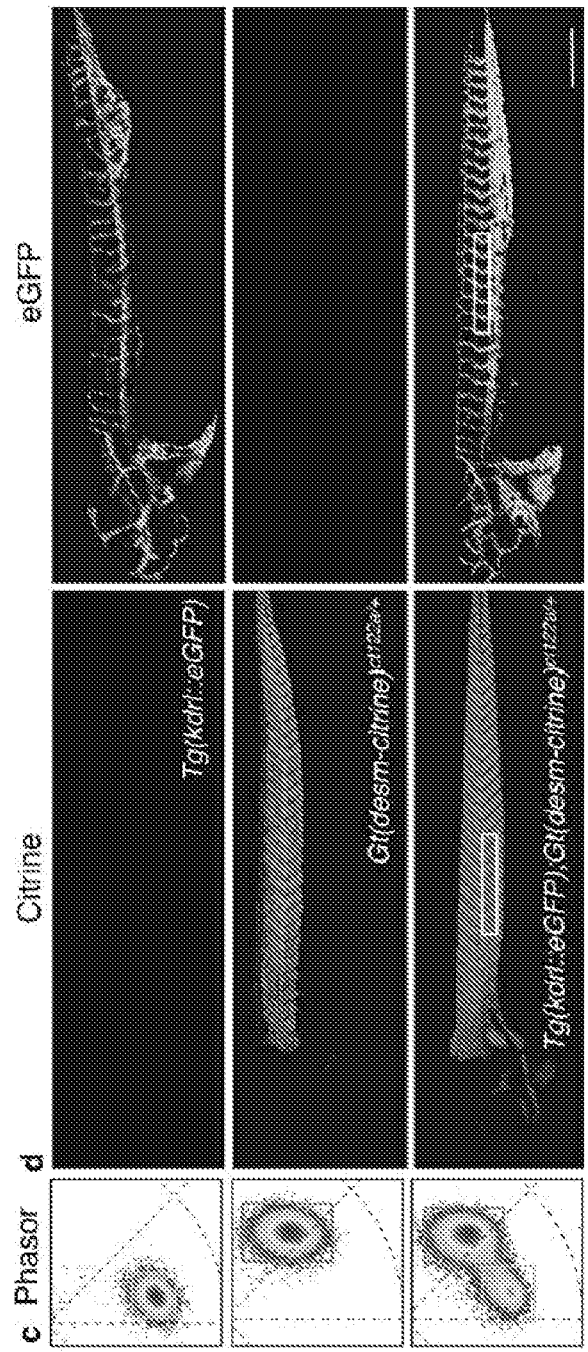

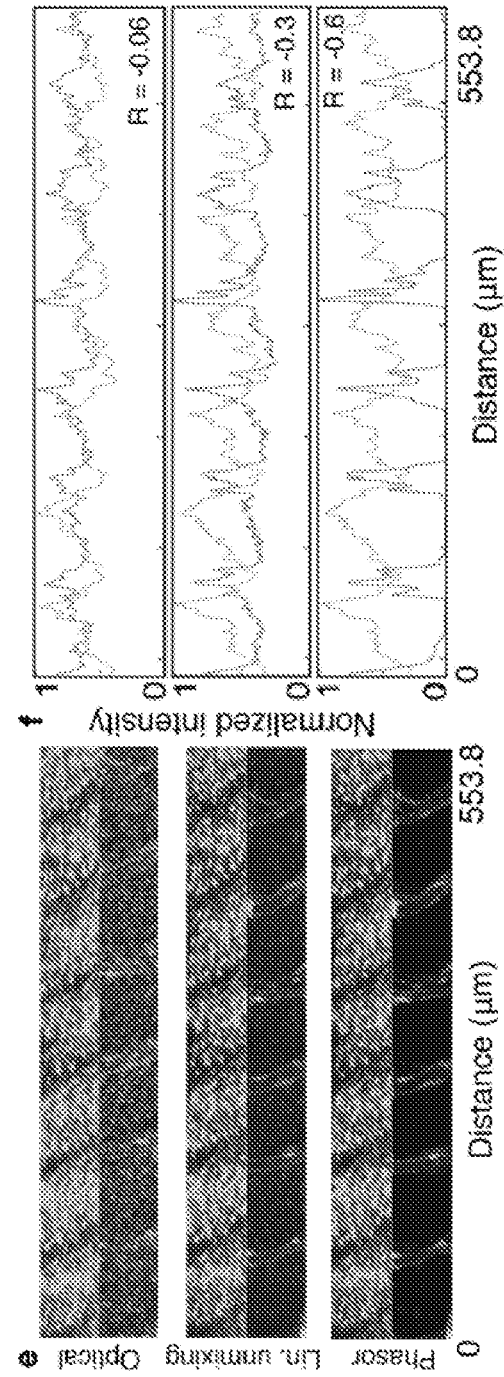

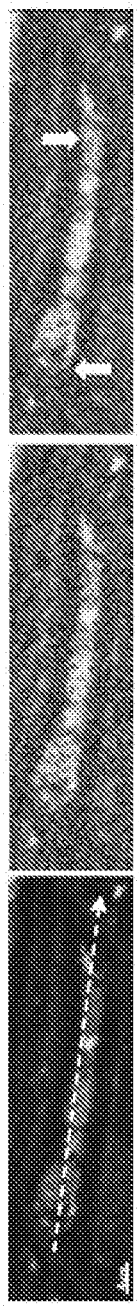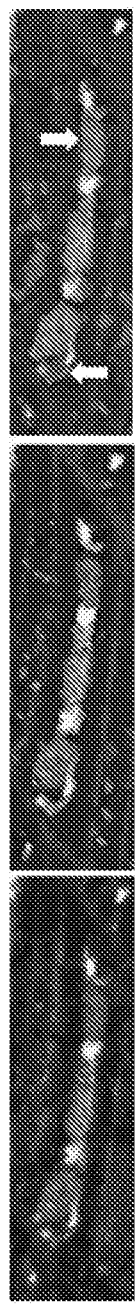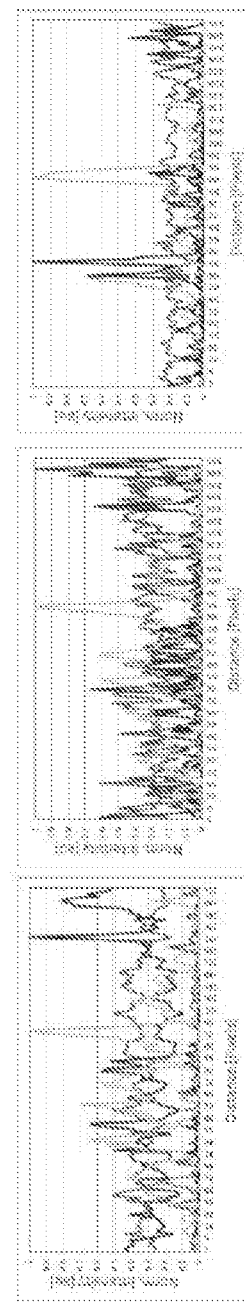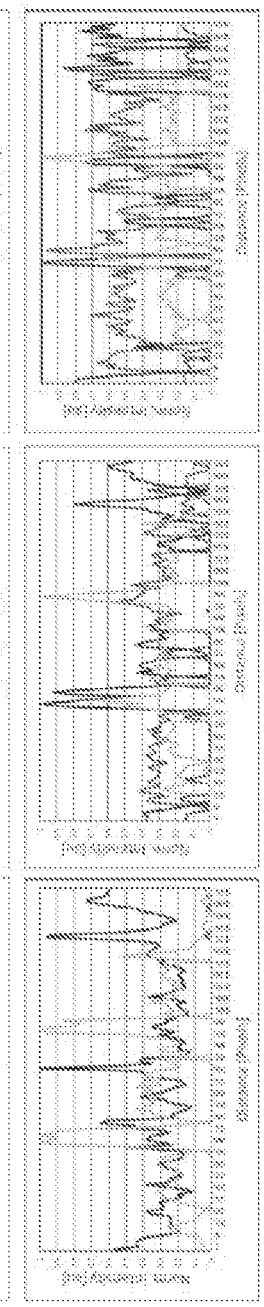
FIG. 11c　　　FIG. 11d

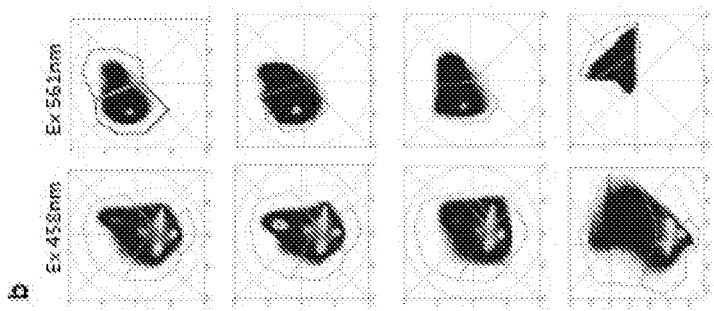
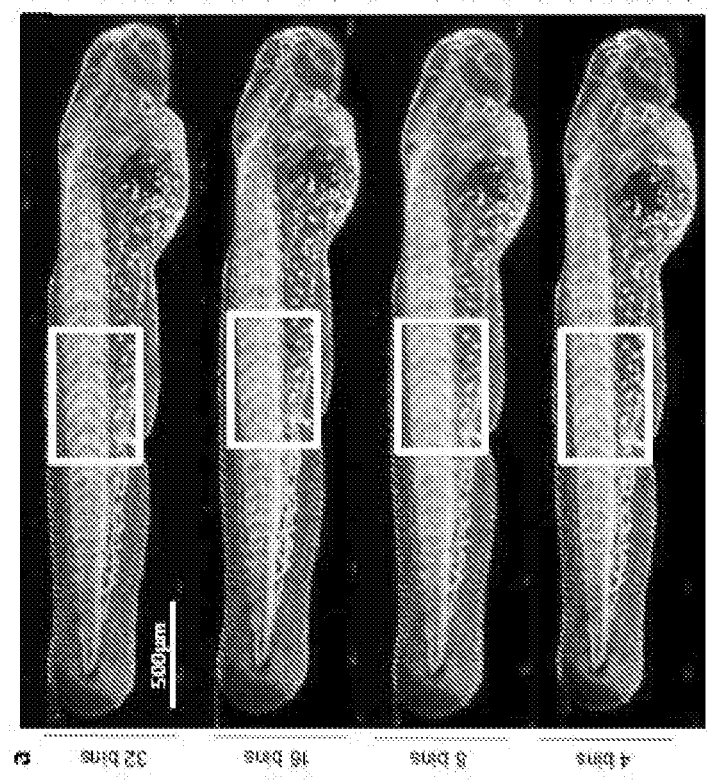
FIG. 13a
FIG. 13b

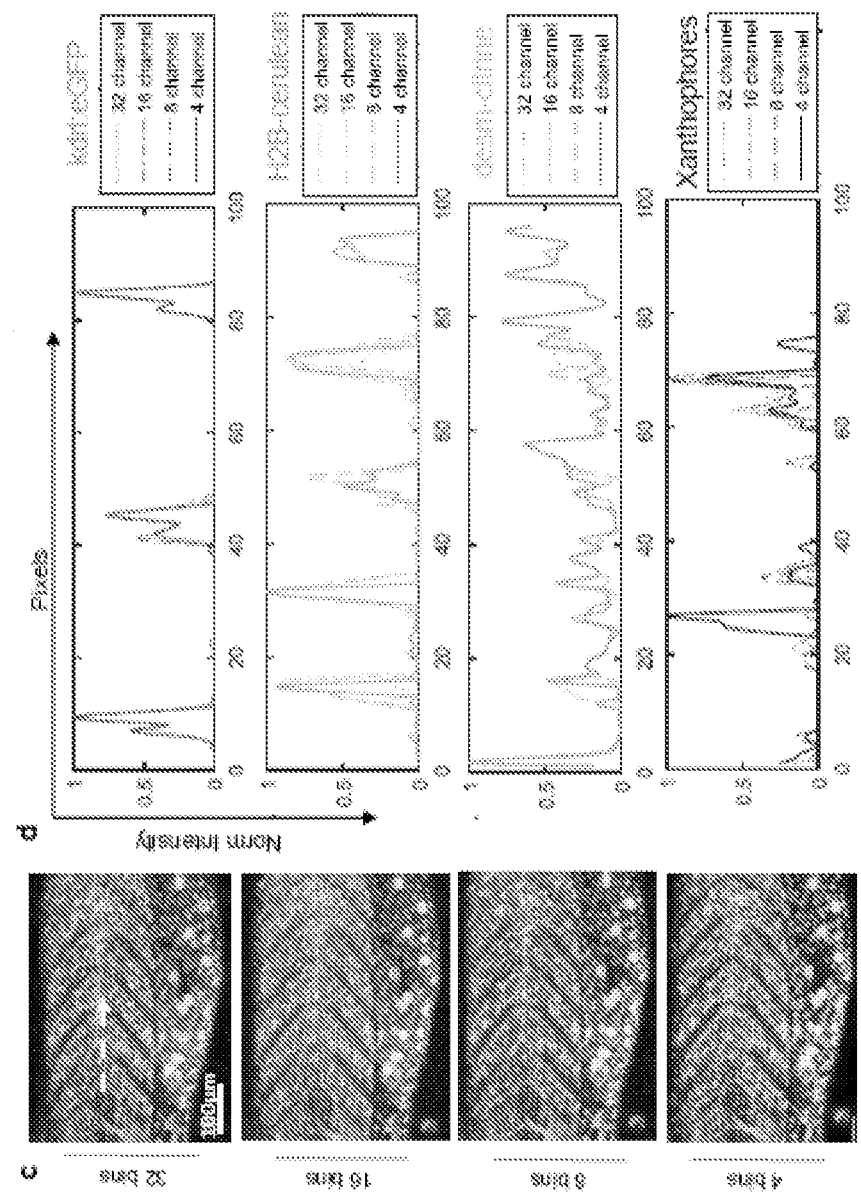

HYPERSPECTRAL IMAGING SYSTEM

CROSS-REFERENCE TO RELATED APPLICATION

This application is a U.S. National Phase Application of International Application No. PCT/US2017/060462, entitled "A Hyperspectral Imaging System," filed on Nov. 7, 2017, which claims the benefit of U.S. Provisional Patent Application No. 62/419,075, entitled "Imaging System," filed Nov. 8, 2016, the complete contents of which are incorporated herein by reference.

STATEMENT REGARDING FEDERALLY SPONSORED RESEARCH

This invention was made with government support under Grant Nos. R01 HD075605 and R01 OD019037 awarded by National Institutes of Health (NIH). The government has certain rights in the invention.

BACKGROUND

Technical Field

This disclosure relates to imaging systems. This disclosure also relates to hyperspectral imaging systems. This disclosure further relates to hyperspectral imaging systems that generate an unmixed color image of a target. This disclosure further relates to hyperspectral imaging systems that are used in diagnosing a health condition.

Description of Related Art

Multi-spectral imaging has emerged as a powerful tool in recent years to simultaneously study multiple labels in biological samples at sub-cellular, cellular and tissue levels [1,2] [all bracketed references are identified below]. Multi-spectral approaches can eliminate the contributions from sample autofluorescence, and permit high levels of signal multiplexing [3-5] since they can unambiguously identify dyes with indistinct spectra [6]. Despite these many advantages and the availability of commercial hardware with multispectral capabilities, these approaches have not been employed, as it has been challenging to simultaneously represent multi-dimensional data (x,y,z,λ,t), either for visual inspection or for quantitative analysis.

Typical approaches using linear unmixing [7] or principal component analysis [8] are computationally challenging and their performance degrades as light levels decrease [7,9]. In the case of time-lapse biological imaging, where the exciting light is usually kept low to minimize photo-toxicity, the noise results in inescapable errors in the processed images [7,9]. Complex datasets often require image segmentation or prior knowledge of the anatomy for such approaches to distinguish unique fluorescent signals in a region of interest [10].

A conventional Spectral Phasor (SP) [14-16] approach offers an efficient processing and rendering tool for multi-spectral data. SP uses Fourier transform to depict the spectrum of every pixel in an image as a point on the phasor plane (FIG. 1a), providing a density plot of the ensemble of pixels. Because SP offers single point representations on a 2D plot of even complex spectra, it simplifies both the interpretation of and interaction with multi-dimensional spectral data. Admixtures of multiple spectra can be graphically analyzed with computational ease. Thus, SP can be adapted to multispectral imaging, and has been shown to be useful for separating up to 3 colors for single time points in biological specimens [14, 15] excluding autofluorescence.

However, existing implementations of the SP approach have not been suitable for the analysis of in vivo multispectral time-lapse fluorescence imaging, especially for a high number of labels. This is primarily due to signal-to-noise (SNR) limitations related to photo-bleaching and phototoxicity when imaging multiple fluorescent proteins with different biophysical properties [17]. Suitable excitation of multiple fluorophores requires a series of excitation wavelengths to provide good SNR images. However, increasing the number of excitation lines impacts the rate of photobleaching and can hamper the biological development dynamics. Furthermore, in the embryo, autofluorescence often increases with the number of excitation wavelengths. The alternative approach of using a single wavelength to excite multiple labels, while reducing the negative photo-effects and amount of autofluorescence, comes at the expense of reduced SNR.

The expanding palette of fluorescent proteins has enabled studies of spatio-temporal interaction of proteins, cells and tissues in vivo within living cells or developing embryos. However, time-lapse imaging of multiple labels remains challenging as noise, photo-bleaching and toxicity greatly compromise signal quality, and throughput can be limited by the time required to unmix spectral signals from multiple labels.

The hyperspectral imaging techniques may be used for medical purposes. For example, see Lu et al. "Medical Hyperspectral Imaging: a Review" Journal of Biomedical Optics 19(1), pages 010901-1 to 010901-23 (January 2014); Vasefi et al. "Polarization-Sensitive Hyperspectral Imaging in vivo: A Multimode Dermoscope for Skin Analysis" Scientific Reports 4, Article number: 4924 (2014); and Burlina et al. "Hyperspectral Imaging for Detection of Skin Related Conditions" U.S. Pat. No. 8,761,476 B2. The entire content of each of these publications is incorporated herein by reference.

RELATED ART REFERENCES

The following publications are related art for the background of this disclosure. One digit or two digit numbers in the box brackets before each reference, i.e. [1] to [29], correspond to the numbers in the box brackets used in the other parts of this disclosure.

[1] Garini, Y., Young, I. T. and McNamara, G. Spectral imaging: principles and applications. Cytometry A 69: 735-747 (2006).

[2] Dickinson, M. E., Simbuerger, E., Zimmermann, B., Waters, C. W. and Fraser, S. E. Multiphoton excitation spectra in biological samples. Journal of Biomedical Optics 8: 329-338 (2003).

[3] Dickinson, M. E., Bearman, G., Tille, S., Lansford, R. & Fraser, S. E. Multi-spectral imaging and linear unmixing add a whole new dimension to laser scanning fluorescence microscopy. Biotechniques 31, 1272-1278 (2001).

[4] Levenson, R. M. and Mansfield, J. R. Multispectral imaging in biology and medicine: Slices of life. Cytometry A 69: 748-758 (2006).

[5] Jahr, W., Schmid, B., Schmied, C., Fahrbach, F. and Huisken, J. Hyperspectral light sheet microscopy. Nat Commun, 6, (2015)

[6] Lansford, R., Bearman, G. and Fraser, S. E. Resolution of multiple green fluorescent protein color variants and dyes using two-photon microscopy and imaging spectroscopy. Journal of Biomedical Optics 6: 311-318 (2001).

[7] Zimmermann, T. Spectral Imaging and Linear Unmixing in Light Microscopy. Adv Biochem Engin/Biotechnol (2005) 95: 245-265

[8] Jolliffe, Ian. Principal component analysis. John Wiley & Sons, Ltd, (2002).

[9] Gong, P. and Zhang, A. Noise Effect on Linear Spectral Unmixing. Geographic Information Sciences 5(1), (1999)

[10] Mukamel, E. A., Nimmerjahn, A., and Schnitzer M. J.; Automated Analysis of Cellular Signals from Large-Scale Calcium Imaging Data; Neuron, 63(6), 747-760

[11] Clayton, A. H., Hanley, Q. S. & Verveer, P. J. Graphical representation and multicomponent analysis of single-frequency fluorescence lifetime imaging microscopy data. J. Microsc. 213, 1-5 (2004)

[12] Redford, G. I. & Clegg, R. M. Polar plot representation for frequency-domain analysis of fluorescence lifetimes. J. Fluoresc. 15, 805-815 (2005).

[13] Digman M A, Caiolfa V R, Zamai M and Gratton E. The phasor approach to fluorescence lifetime imaging analysis. Biophys. J. 94 pp. 14-16 (2008)

[14] Fereidouni F., Bader A. N. and Gerritsen H. C. Spectral phasor analysis allows rapid and reliable unmixing of fluorescence microscopy spectral images. Opt. Express 20 12729-41 (2012)

[15] Andrews L. M., Jones M. R., Digman M. A., Gratton E. Spectral phasor analysis of Pyronin Y labeled RNA microenvironments in living cells. Biomed. Op. Express 4 (1) 171-177 (2013)

[16] Cutrale F., Salih A. and Gratton E. Spectral phasor approach for fingerprinting of photo-activatable fluorescent proteins Dronpa, Kaede and KikGR. Methods Appl. Fluoresc. 1 (3) (2013) 035001

[17] Cranfill P. J., Sell B. R., Baird M. A., Allen J. R., Lavagnino Z., de Gruiter H. M., Kremers G., Davidson M. W., Ustione A., Piston D. W., Quantitative assessment of fluorescent proteins, Nature Methods 13, 557-562 (2016).

[18] Chen, H., Gratton, E., & Digman, M. A. Spectral Properties and Dynamics of Gold Nanorods Revealed by EMCCD-Based Spectral Phasor Method. Microscopy Research and Technique, 78(4), 283-293 (2015)

[19] Vermot, J., Fraser, S. E., Liebling, M. "Fast fluorescence microscopy for imaging the dynamics of embryonic development," HFSP Journal, vol 2, pp. 143-155, (2008)

[20] Dalal, R. B., Digman, M. A., Horwitz, A. F., Vetri, V., Gratton, E., Determination of particle number and brightness using a laser scanning confocal microscope operating in the analog mode, Microsc. Res. Tech., 71(1) pp. 69-81 (2008)

[21] Fereidouni, F., Reitsma, K., Gerritsen, H. C. High speed multispectral fluorescence lifetime imaging, Optics Express, 21(10), pp. 11769-11782 (2013)

[22] Hamamatsu Photonics K. K. Photomultiplier Technical Handbook. (1994) Hamamatsu Photonics K. K

[23] Trinh, L. A. et al., "A versatile gene trap to visualize and interrogate the function of the vertebrate proteome," Genes & development, 25(21), 2306-20 (2011).

[24] Jin S. W., Beis D., Mitchell T., Chen J. N., Stainier D. Y. Cellular and molecular analyses of vascular tube and lumen formation in zebrafish. Development 132, 5199-5209 (2005)

[25] Livet, J., Weissman, T. A., Kang, H., Draft, R. W., Lu, J., Bennis, R. A., Sanes, J. R., Lichtman J. W. Transgenic strategies for combinatorial expression of fluorescent proteins in the nervous system. Nature, 450(7166), 56-62 (2007)

[26] Lichtman, J. W., Livet, J., & Sanes, J. R. A technicolour approach to the connectome. Nature Reviews Neuroscience, 9(6), 417-422 (2008).

[27] Pan, Y. A., Freundlich, T., Weissman, T. A., Schoppik, D., Wang, X. C., Zimmerman, S., Ciruna, B., Sanes, J. R., Lichtman, J. W., Schier A. F. Zebrabow: multispectral cell labeling for cell tracing and lineage analysis in zebrafish. Development, 140(13), 2835-2846. (2013)

[28] Westerfield M. The Zebrafish Book. (1994) Eugene, Oreg.: University Oregon Press.

[29] Megason, S. G. In toto imaging of embryogenesis with confocal time-lapse microscopy. Methods in molecular biology, 546 pp. 317-32 (2009).

The entire content of each of above publications is incorporated herein by reference.

SUMMARY

An imaging system for denoising and/or color unmixing multiple overlapping spectra in a low signal-to-noise regime with a fast analysis time is disclosed. This imaging system may be a hyperspectral imaging system. A system may be configured to carry out Hyper-Spectral Phasors (HySP) calculations to effectively analyze hyper-spectral time-lapse data. For example, this system may be configured to carry out Hyper-Spectral Phasors (HySP) calculations to effectively analyze five-dimensional (5D) hyper-spectral time-lapse data. Advantages of this imaging system may include: (a) fast computational speed, (b) the ease of phasor analysis, and (c) a denoising algorithm to obtain minimally-acceptable signal-to-noise ratio (SNR). This imaging system may also generate an unmixed color image of a target. This imaging system may be used in diagnosis of a health condition.

The hyperspectral imaging system may comprise an optics system, an image forming system, or a combination thereof. For example, the hyperspectral imaging system may comprise an optics system and an image forming system. For example, the hyperspectral imaging system may comprise an image forming system.

The optics system may comprise at least one optical component. Examples of the at least one optical component are a detector ("optical detector"), a detector array ("optical detector array"), a source to illuminate the target ("illumination source"), a first optical lens, a second optical lens, a dispersive optic system, a dichroic mirror/beam splitter, a first optical filtering system, a second optical filtering system, or a combination thereof. For example, the at least one optical detector may comprise at least one optical detector. For example, the at least one optical detector may comprise at least one optical detector and at least one illumination source. A first optical filtering system may be placed between the target and the at least one optical detector. A second optical filtering system may be placed between the first optical filtering system and the at least one optical detector.

The optical system may comprise an optical microscope. The components of the optical system may be configured to form this optical microscope. Examples of the optical microscope may be a confocal fluorescence microscope, a two-photon fluorescence microscope, or a combination thereof.

The at least one optical detector may have a configuration that detects electromagnetic radiation absorbed, transmitted, refracted, reflected, and/or emitted ("target radiation") by at least one physical point on the target. The target radiation may comprise at least one wave ("target wave"). The target radiation may comprise at least two target waves. Each target wave may have an intensity and a different wavelength. The at least one optical detector may have a configuration that detects the intensity and the wavelength of each target wave. The at least one optical detector may have a configuration that transmits the detected intensity and wavelength of each target wave to the image forming system. The at least one optical detector may comprise a photomultiplier tube, a photomultiplier tube array, a digital camera, a hyperspectral camera, an electron multiplying charge coupled device, a Sci-CMOS, a digital camera, or a combination thereof.

The target radiation may comprise an electromagnetic radiation emitted by the target. The electromagnetic radiation emitted by the target may comprise luminescence, thermal radiation, or a combination thereof. The luminescence may comprise fluorescence, phosphorescence, or a combination thereof. For example, the electromagnetic radiation emitted by the target may comprise fluorescence, phosphorescence, thermal radiation, or a combination thereof.

The at least one optical detector may detect the electromagnetic radiation emitted by the target at a wavelength in the range of 300 nm to 800 nm. The at least one optical detector may detect the electromagnetic radiation emitted by the target at a wavelength in the range of 300 nm to 1,300 nm.

The hyperspectral imaging system may also form a detected image of the target using the target radiation comprising at least four wavelengths, wherein the at least four wavelengths with detected intensities form a spectrum. Color resolution of the image may thereby be increased.

The at least one illumination source may generate an electromagnetic radiation ("illumination source radiation"). The illumination source radiation may comprise at least one wave ("illumination wave"). The illumination source radiation may comprise at least two illumination waves. Each illumination wave may have a different wavelength. The at least one illumination source may directly illuminate the target. In this configuration, there is no optical component between the illumination source and the target. The at least one illumination source may indirectly illuminate the target. In this configuration, there is at least one optical component between the illumination source and the target. The illumination source may illuminate the target at each illumination wavelength by simultaneously transmitting all illumination waves. The illumination source may illuminate the target at each illumination wavelength by sequentially transmitting all illumination waves.

The illumination source may comprise a coherent electromagnetic radiation source. The coherent electromagnetic radiation source may comprise a laser, a diode, a two-photon excitation source, a three-photon excitation source, or a combination thereof.

The illumination source radiation may comprise an illumination wave with a wavelength in the range of 300 nm to 1,300 nm. The illumination source radiation may comprise an illumination wave with a wavelength in the range of 300 nm to 700 nm. The illumination source radiation may comprise an illumination wave with a wavelength in the range of 690 nm to 1,300 nm.

The image forming system may comprise a control system, a hardware processor, a memory, a display, or a combination thereof.

The image forming system may have a configuration that causes the optical detector to detect the target radiation and to transmit the detected intensity and wavelength of each target wave to the image forming system; acquires the detected target radiation comprising the at least two target waves; forms an image of the target using the detected target radiation ("target image"), wherein the target image comprises at least two pixels, and wherein each pixel corresponds to one physical point on the target; forms at least one spectrum for each pixel using the detected intensity and wavelength of each target wave ("intensity spectrum"); transforms the formed intensity spectrum of each pixel using a Fourier transform into a complex-valued function based on the intensity spectrum of each pixel, wherein each complex-valued function has at least one real component and at least one imaginary component; applies a denoising filter on both the real component and the imaginary component of each complex-valued function at least once so as to produce a denoised real value and a denoised imaginary value for each pixel; forms one point on a phasor plane ("phasor point") for each pixel by plotting the denoised real value against the denoised imaginary value of each pixel; maps back the phasor point to a corresponding pixel on the target image based on the phasor point's geometric position on the phasor plane; assigns an arbitrary color to the corresponding pixel based on the geometric position of the phasor point on the phasor plane; and generates an unmixed color image of the target based on the assigned arbitrary color. The image forming system may also have a configuration that displays the unmixed color image of the target on the image forming system's display.

The image forming system may have a configuration that uses at least one harmonic of the Fourier transform to generate the unmixed color image of the target. The image forming system may be configured to use at least a first harmonic of the Fourier transform to generate the unmixed color image of the target. The image forming system may be configured to use at least a second harmonic of the Fourier transform to generate the unmixed color image of the target. The image forming system may be configured to use at least a first harmonic and a second harmonic of the Fourier transform to generate the unmixed color image of the target The denoising filter may comprise a median filter.

The unmixed color image of the target may be formed at a signal-to-noise ratio of the at least one spectrum in the range of 1.2 to 50. The unmixed color image of the target may be formed at a signal-to-noise ratio of the at least one spectrum in the range of 2 to 50.

The target may be any target. The target may be any target that has a specific spectrum of color. For example, the target may be a tissue, a fluorescent genetic label, an inorganic target, or a combination thereof.

The hyperspectral imaging system may be calibrated by using a reference material to assign arbitrary colors to each pixel. The reference material may be any known reference material. For example, the reference may be any reference material wherein unmixed color image of the reference material is determined prior to the generation of unmixed color image of the target. For example, the reference material may be a physical structure, a chemical molecule, a biological molecule, a biological activity (e.g. physiological change) as a result of physical structural change and/or disease.

Any combination of above features/configurations is within the scope of the instant disclosure.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps. The colors disclosed in the following brief description of drawings and other parts of this disclosure refer to the color drawings and photos as originally filed with the U.S. provisional patent application 62/419,075, entitled "An Imaging System," on Nov. 8, 2016. The patent application file contains these drawings and photos executed in color. Copies of this patent application file with color drawings will be provided by the United States Patent and Trademark Office upon request and payment of the necessary fee.

The following reference numerals are used for the system features disclosed in the following figures: a hyperspectral imaging system 10, an optics system 20, an image forming system 30, a control system 40, a hardware processor(s) 50, a memory system 60, a display 70, a fluorescence microscope 100, a multiple illumination wavelength microscope 200, a multiple wavelength detection microscope 300, a multiple wavelength detection device 400, a multiple illumination wavelength and multiple wavelength detection microscope 500, a multiple wavelength detection device 600, a multiple wavelength detection device 700, an illumination source 101, a dichroic mirror/beam splitter 102, a first optical lens 103, a second optical lens 104, a target (i.e. sample) 105, a (optical) detector 106, an illumination source radiation 107, an emitted target radiation 108, an illumination source radiation at a first wavelength 201, an illumination source radiation at a second wavelength 202, an emitted target radiation or reflected illumination source radiation at a first wavelength 203, an emitted target radiation or reflected illumination source radiation at a second wavelength 204, an emitted target radiation or reflected illumination source radiation 301, a dispersive optic 302, a spectrally dispersed target radiation 303, an optical detector array 304, a target image formation 401, a spectrum formation 402, a Fourier transformation 403, a real component of the Fourier function 404, an imaginary component of the Fourier function 405, a denoising filter 406, a plotting on phasor plane 407, a mapping back to target image 408, and a formation of unmixed color image of the target 409.

FIG. 4 Errors on spectral phasor plot. (a) scatter error may scale inversely as the square root of the total digital counts. The legend is applicable to all parts of the figure. Scatter error may also depend on the Poissonian noise in the recording. R-squared statistical method may be used to confirm linearity with the reciprocal of square root of counts. The slope may be a function of the detector gain used in acquisition showing the counts-to-scatter error dynamic range is inversely proportional to the gain. Lower gains may produce smaller scatter error at lower intensity values. (b) Denoising in the phasor space may reduce the scatter error without affecting the location of expected values ($z_e(n)$) on the phasor plot. (c) Denoised scatter error may linearly depend on the scatter error without filtering, irrespective of the acquisition parameters. The slope may be determined by the filter size (3×3 here). (d) Denoising may not affect normalized shifted-mean errors since the locations of $z_e(n)$'s on the phasor plot remain unaltered due to filtering (d).

FIG. 6 Phasor analysis for unmixing hyper-spectral fluorescent signals in vivo. (a) Schematic of the expression patterns of Citrine (skeletal muscles) and eGFP (endothelial tissue) in transgenic zebrafish lines Gt(desm-citrine)$^{ct122a/+}$ and Tg(kdrl:eGFP) respectively. (b) Conventional optical filter separation for Gt(desm-citrine)$^{ct122a/+}$ Tg(kdrl:eGFP). Using emission bands on detector of spectrally overlapping fluorophores (eGFP and citrine) may not overcome the problem of bleed-through of signal in respective channels. Arrows indicate erroneous detection of eGFP or Citrine expressions in the other channel. Scale bar, about 200 µm. (c) Phasor plots showing spectral fingerprints (scatter densities) for Citrine and eGFP in individually expressed embryo and double transgenic. The individual Citrine and eGFP spectral fingerprints may remain preserved in the double transgenic line. (d) Maximum intensity projection images reconstructed by mapping the scatter densities from phasor plot to the original volume. eGFP and Citrine fingerprints may cleanly distinguish the skeletal muscles from interspersed blood vessels (endothelial tissue), though within the same anatomical region of the embryo, in both single and double transgenic lines. Scale bar about 300 µm. Embryos imaged about 72 hours post fertilization. (e,f) HySP analysis may outperform optical separation and linear unmixing in distinguishing spectrally overlapping fluorophores in vivo. (e) Maximum intensity projection images of the region in Tg(kdrl:eGFP); Gt(desm-citrine)$^{ct122a/+}$ shown in (d) compares the signal for eGFP and Citrine detected by optical separation, linear unmixing and phasor analysis. (f) Corresponding normalized intensity profiles along the width (600 pixels, about 553.8 µm) of the image integrated over a height of 60 pixels. Correlation values (R) reported for the three cases show the lowest value for HySP analysis, as expected by the expressions of the two proteins.

Lowering SNR, however, affects the linear unmixing more than the phasor. This can improve unmixing of labels in volumetric imaging of biological samples, where generally SNR decreases with depth and explains the differences in FIG. 2e, f; FIG. 6e, f; FIG. 10 and FIG. 12. One advantage of HySP, in this SNR comparison, may be the spectral denoising in Fourier space. Spectral denoising may be performed by applying filters directly in phasor space. This may maintain the original image resolution but may improve spectral fingerprinting in the phasor plot. A median filter may be applied as the filter. However, other filtering approaches may also be possible. For any image of a given size (n×m pixels), S and G values may be obtained for every pixel, yielding 2 new 2D matrices, for S and G, with dimensions n×m. Since the initial S and G matrix entries may have the same indices as the pixels in the image, the filtered matrices S* and G*, therefore, may preserve the geometrical information. Effectively by using filtering in phasor space, S and G matrices may be treated as 2D images. First, this may reduce the scatter error, i.e. the localization precision on phasor plot increases (FIG. 8a-b), improving the spectral fingerprinting resolution while improving the already minimal Shifted-Mean Error (FIG. 8c-d). The effect on data may be an improved separation of distinct fluorescent proteins (FIG. 9a-d). Second, denoising in (G,S) coordinates may preserve both geometry, intensity profile as well as the original resolution at which the images were acquired (FIG. 9e-g). Effectively filtering in phasor space may affect the spectral dimension of the data achieving denoising of spectral noise without interfering with intensities. (e) Intensity profile (dashed arrow in (c)) comparison may show the improvement of HySP at low SNR. Under decreased SNR H2B-cerulean (cyan) and desm-citrine (yellow) (solid arrows in (c)) may consistently be identified in HySP while they may be partially mislabeled in linear unmixing. For example, some noisy may be identified as kdrl:eGFP (green) while, anatomically no vasculature is present in this region of interest.

FIG. 12 Comparison of HySP and Linear unmixing in resolving seven fluorescent signals. (a) Gray scale images from different optical sections, same as the ones used in FIG. 2 (Regions 1-3), comparing the performance of HySP analysis and linear unmixing. (b) Normalized intensity plots for comparison of HySP analysis and linear unmixing. Similar to the corresponding panels in FIG. 2f, the x-axes denote the normalized distance and y-axes in all graphs were normalized to the value of maximum signal intensity among the seven channels to allow relative comparison. The panels show all intensity profiles for seven channels in the respective images.

FIG. 13 Effect of binning on HySP analysis of seven in vivo fluorescent signals. The original dataset acquired with 32 channels may be computationally binned sequentially to 16, 8 and 4 channels to understand the limits of HySP in unmixing the selected fluorescence spectral signatures. The binning may not produce visible deterioration of the unmixing. White square area may be used for zoomed comparison of different bins. Spectral phasor plots at about 458 nm and about 561 nm excitation. Binning of data may result in shorter phasor distances between different fluorescent spectral fingerprints. Clusters, even if closer, may still be recognizable. Zoomed-in comparison of embryo trunk (box in (a)). Differences for HySP analysis for the same dataset at different binning values may still be subtle to the eye. One volume may be chosen for investigating intensity profiles (white dashed arrow). Intensity profiles for kdrl:eGFP, H2B-cerulean, desm-citrine and Xanthophores at different binning for summed intensities of a volume of about 26.60 µm×about 0.27 µm×about 20.00 µm (white dashed arrow (c)). The effects of binning may now be visible. For vasculature the unmixing may not be excessively deteriorated by the binning. Same result for nuclei. Desm and xanthophores may seem to be more affected by binning. This result may suggest that, in our case of zebrafish embryo with seven separate spectral fingerprints acquired sequentially using two different lasers, it is possible to use 4 bins at the expense of a deterioration of the unmixing.

DETAILED DESCRIPTION OF ILLUSTRATIVE EMBODIMENTS

Illustrative embodiments are now described. Other embodiments may be used in addition or instead. Details that may be apparent or unnecessary may be omitted to save space or for a more effective presentation. Some embodiments may be practiced with additional components or steps and/or without all of the components or steps that are described.

Following acronyms are used.
2D: Two dimensional
5D: Five dimensional.
HySP: Hyper-Spectral Phasors
IACUC: Institutional Animal Care and Use Committee
N: Number of acquired photons
n: Harmonic number
PMT: Photomultiplier tube
PTU: 1-phenyl-2-thiourea
SBR: Signal-to-background ratios
SNR: signal to noise
SP: Spectral Phasor
USC: University of Southern California This disclosure relates to a hyperspectral imaging system. This disclosure further relates to a hyperspectral imaging system that generates an unmixed color image of a target. This imaging system may be used for denoising and/or color unmixing multiple overlapping spectra in a low signal-to-noise regime with a fast analysis time. The unmixed color image of the target may be used in diagnosing a health condition.

The hyperspectral imaging system may be configured to carry out Hyper-Spectral Phasor (HySP) calculations to effectively analyze hyper-spectral time-lapse data. For example, this system may be configured to carry out HySP calculations to effectively analyze five-dimensional (5D) hyper-spectral time-lapse data. The main advantages of this system may comprise: (a) fast computational speed, (b) the ease of phasor analysis, and (c) a denoising system to obtain the minimally-acceptable signal-to-noise ratio (SNR), as demonstrated by way of example in FIG. 1.

This hyperspectral imaging system may efficiently reduce spectral noise, remove autofluorescence, and distinguish multiple spectrally-overlapping fluorophores within biological samples. This system may improve in vivo imaging, both by expanding the fluorophore palette choice and by reducing the contribution from background autofluorescence. In an example below, the robustness of HySP is demonstrated by imaging developing zebrafish embryos with seven colors during light-sensitive stages of development (FIGS. 2-3).

Figure 14:
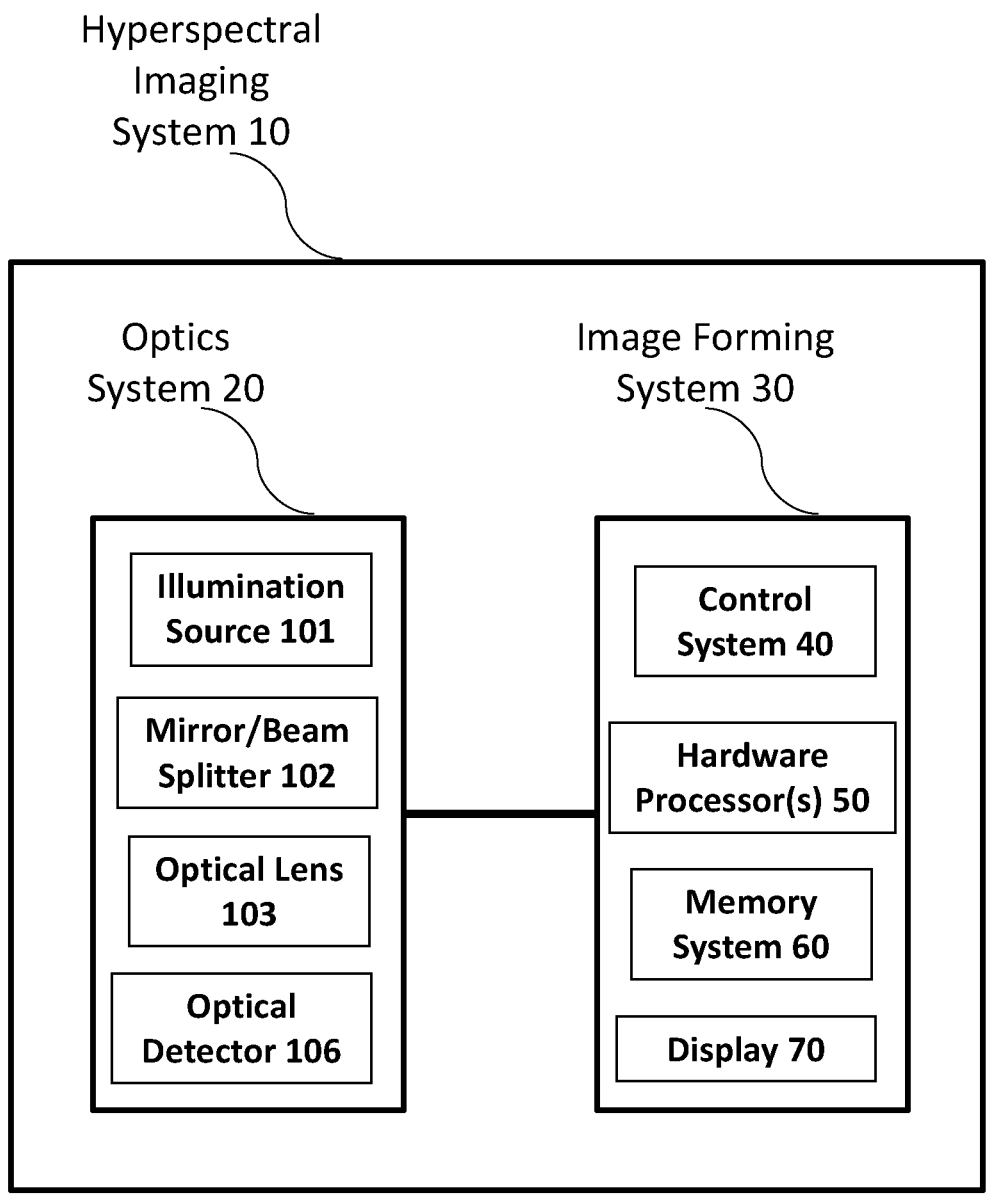
FIG. 14 An exemplary hyperspectral imaging system comprising an exemplary optics system and an exemplary image forming system.
Figure 22:
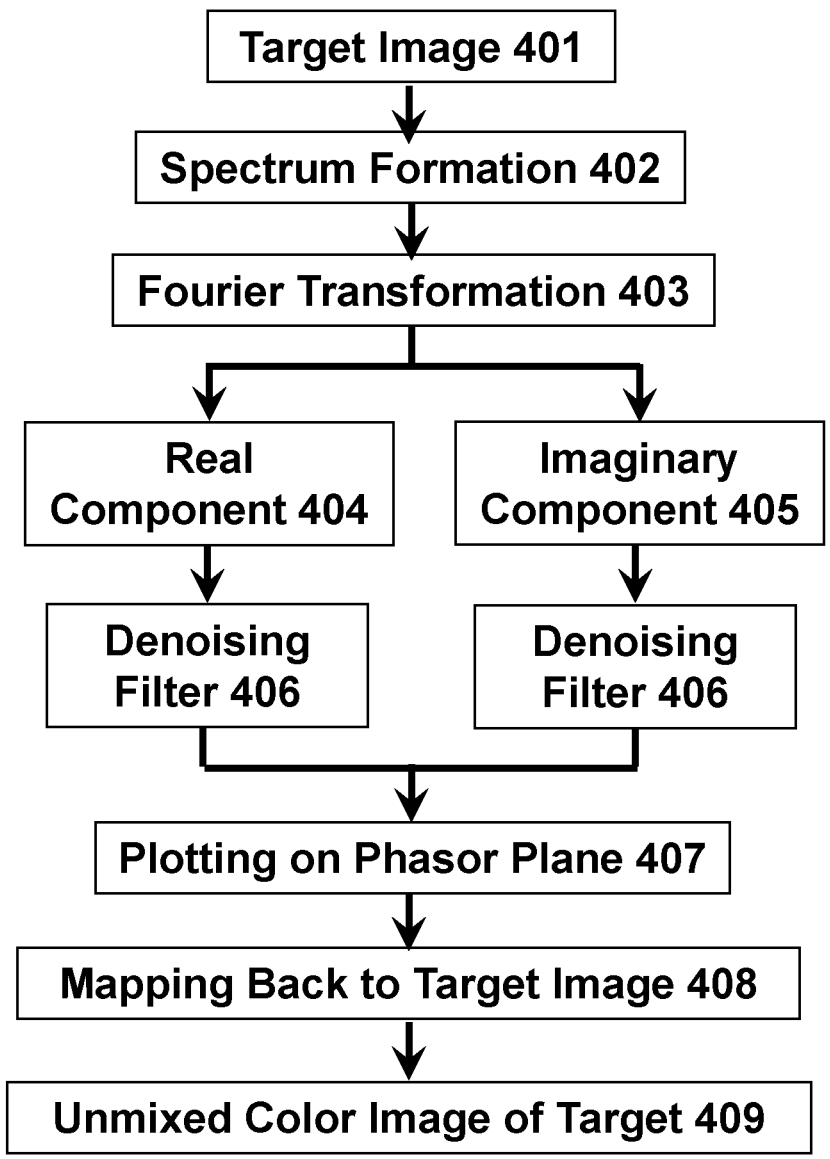
FIG. 22 Features of an exemplary image forming system that may be used to generate an unmixed color image of a target.
Figure 23:
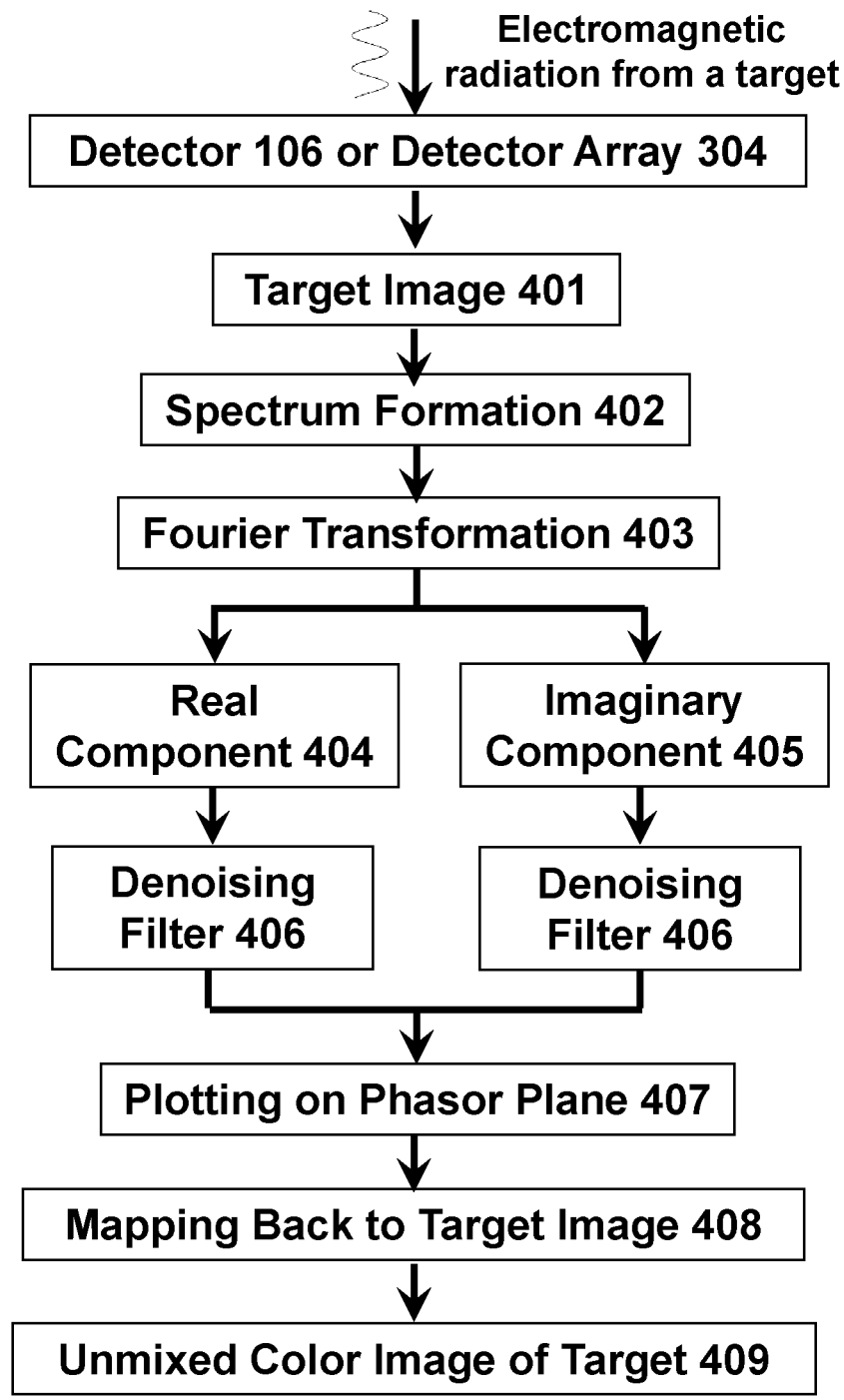
FIG. 23 Features of an exemplary image forming system that may be used to generate an unmixed color image of a target.

The hyperspectral imaging system 10 may comprise an optics system 20, an image forming system 30, or a combination thereof. For example, the hyperspectral imaging system may comprise and an optics system and an image forming system. For example, the hyperspectral imaging system may comprise an image forming system. One example of the exemplary hyperspectral imaging system comprising an optics system and an image forming system is schematically shown in FIG. 14. Exemplary optics systems are shown in FIGS. 15-21. An exemplary configuration of the image forming system is shown in FIG. 22. An exemplary configuration of the hyperspectral imaging system is shown in FIG. 23.

In this disclosure, the optics system may comprise at least one optical component. Examples of the at least one optical component are a detector ("optical detector"), a detector array ("optical detector array"), a source to illuminate the target ("illumination source"), a first optical lens, a second optical lens, an optical filter, a dispersive optic system, a dichroic mirror/beam splitter, a first optical filtering system placed between the target and the at least one optical detector, a second optical filtering system placed between the first optical filtering system and the at least one optical detector, or a combination thereof. For example, the at least one optical component may comprise at least one optical detector. For example, the at least one optical component may comprise at least one optical detector and at least one illumination source. For example, the at least one optical component may comprise at least one optical detector, at least one illumination source, at least one optical lens, at least one optical filter, and at least one dispersive optic system. For example, the at least one optical component may comprise at least one optical detector, at least one illumination source, a first optical lens, a second optical lens, and a dichroic mirror/beam splitter. For example, the at least one optical component may comprise at least one optical detector, at least one illumination source, an optical lens, a dispersive optic; and wherein at least one optical detector is an optical detector array. For example, the at least one optical component may comprise at least one optical detector, at least one illumination source, an optical lens, a dispersive optic, a dichroic mirror/beam splitter; and wherein at least one optical detector is an optical detector array. For example, the at least one optical component may comprise at least one optical detector, at least one illumination source, an optical lens, a dispersive optic, a dichroic mirror/beam splitter; wherein at least one optical detector is an optical detector array; and wherein the illumination source directly illuminates the target. These optical components may be configured to form, for example, the exemplary optics systems shown in FIGS. 15-21.

In this disclosure, the optical system may comprise an optical microscope. Examples of the optical microscope may be a confocal fluorescence microscope, a two-photon fluorescence microscope, or a combination thereof.

In this disclosure, the at least one optical detector may have a configuration that detects electromagnetic radiation absorbed, transmitted, refracted, reflected, and/or emitted ("target radiation") by at least one physical point on the target. The target radiation may comprise at least one wave ("target wave"). The target radiation may comprise at least two target waves. Each target wave may have an intensity and a different wavelength. The at least one optical detector may have a configuration that detects the intensity and the wavelength of each target wave. The at least one optical detector may have a configuration that transmits the detected target radiation to the image forming system. The at least one optical detector may have a configuration that transmits the detected intensity and wavelength of each target wave to the image forming system. The at least one optical detector may have any combination of these configurations.

The at least one optical detector may comprise a photomultiplier tube, a photomultiplier tube array, a digital camera, a hyperspectral camera, an electron multiplying charge coupled device, a Sci-CMOS, a digital camera, or a combination thereof. The digital camera may be any digital camera. The digital camera may be used together with an active filter for detection of the target radiation. The digital camera may also be used together with an active filter for detection of the target radiation, for example, comprising, luminescence, thermal radiation, or a combination thereof.

In this disclosure, the target radiation may comprise an electromagnetic radiation emitted by the target. The electromagnetic radiation emitted by the target may comprise luminescence, thermal radiation, or a combination thereof. The luminescence may comprise fluorescence, phosphorescence, or a combination thereof. For example, the electromagnetic radiation emitted by the target may comprise fluorescence, phosphorescence, thermal radiation, or a combination thereof. For example, the electromagnetic radiation emitted by the target may comprise fluorescence. The at least one optical component may further comprise a first optical filtering system. The at least one optical component may further comprise a first optical filtering system and a second optical filtering system. The first optical filtering system may be placed between the target and the at least one optical detector. The second optical filtering system may be placed between the first optical filtering system and the at least one optical detector. The first optical filtering system may comprise a dichroic filter, a beam splitter type filter, or a combination thereof. The second optical filtering system may comprise a notch filter, an active filter, or a combination thereof. The active filter may comprise an adaptive optical system, an acousto-optic tunable filter, a liquid crystal tunable bandpass filter, a Fabry-Perot interferometric filter, or a combination thereof.

In this disclosure, the at least one optical detector may detect the target radiation at a wavelength in the range of 300 nm to 800 nm. The at least one optical detector may detect the target radiation at a wavelength in the range of 300 nm to 1,300 nm.

In this disclosure, the at least one illumination source may generate an electromagnetic radiation ("illumination source radiation"). The illumination source radiation may comprise at least one wave ("illumination wave"). The illumination source radiation may comprise at least two illumination waves. Each illumination wave may have a different wavelength. The at least one illumination source may directly illuminate the target. In this configuration, there is no optical component between the illumination source and the target. The at least one illumination source may indirectly illuminate the target. In this configuration, there is at least one optical component between the illumination source and the target. The illumination source may illuminate the target at each illumination wavelength by simultaneously transmitting all illumination waves. The illumination source may illuminate the target at each illumination wavelength by sequentially transmitting all illumination waves.

In this disclosure, the illumination source may comprise a coherent electromagnetic radiation source. The coherent electromagnetic radiation source may comprise a laser, a diode, a two-photon excitation source, a three-photon excitation source, or a combination thereof.

In this disclosure, the illumination source radiation may comprise an illumination wave with a wavelength in the range of 300 nm to 1,300 nm. The illumination source radiation may comprise an illumination wave with a wavelength in the range of 300 nm to 700 nm. The illumination source radiation may comprise an illumination wave with a wavelength in the range of 690 nm to 1,300 nm. For example, the illumination source may be a one-photon excitation source that is capable of generating electromagnetic radiation in the range of 300 to 700 nm. For example, such one-photon excitation source may generate an electromagnetic radiation that may comprise a wave with a wavelength of about 405 nm, about 458 nm, about 488 nm, about 514 nm, about 554 nm, about 561 nm, about 592 nm, about 630 nm, or a combination thereof. In another example, the source may be a two-photon excitation source that is capable of generating electromagnetic radiation in the range of 690 nm to 1,300 nm. Such excitation source may be a tunable laser. Yet in another example, the source may a one-photon excitation source and a two-photon excitation source that is capable of generating electromagnetic radiation in the range of 300 nm to 1,300 nm. For example, such one-photon excitation source may generate an electromagnetic radiation that may comprise a wave with a wavelength of about 405 nm, about 458 nm, about 488 nm, about 514 nm, about 554 nm, about 561 nm, about 592 nm, about 630 nm, or a combination thereof. For example, such two-photon excitation source may be capable of generating electromagnetic radiation in the range of 690 nm to 1,300 nm. Such two-photon excitation source may be a tunable laser.

In this disclosure, the intensity of the illumination source radiation may not be higher than a certain level such that when the target is illuminated the target is not damaged by the illumination source radiation.

In this disclosure, the hyperspectral imaging system may comprise a microscope. The microscope may be any microscope. For example, the microscope may be an optical microscope. Any optical microscope may be suitable for the system. Examples of an optical microscope may be a two-photon microscope, a one-photon confocal microscope, or a combination thereof. Examples of the two-photon microscopes are disclosed in Alberto Diaspro "Confocal and Two-Photon Microscopy: Foundations, Applications and Advances" Wiley-Liss, New York, November 2001; and Greenfield Sluder and David E. Wolf "Digital Microscopy" 4th Edition, Academic Press, Aug. 20, 2013. The entire content of each of these publications is incorporated herein by reference.

Figure 15:
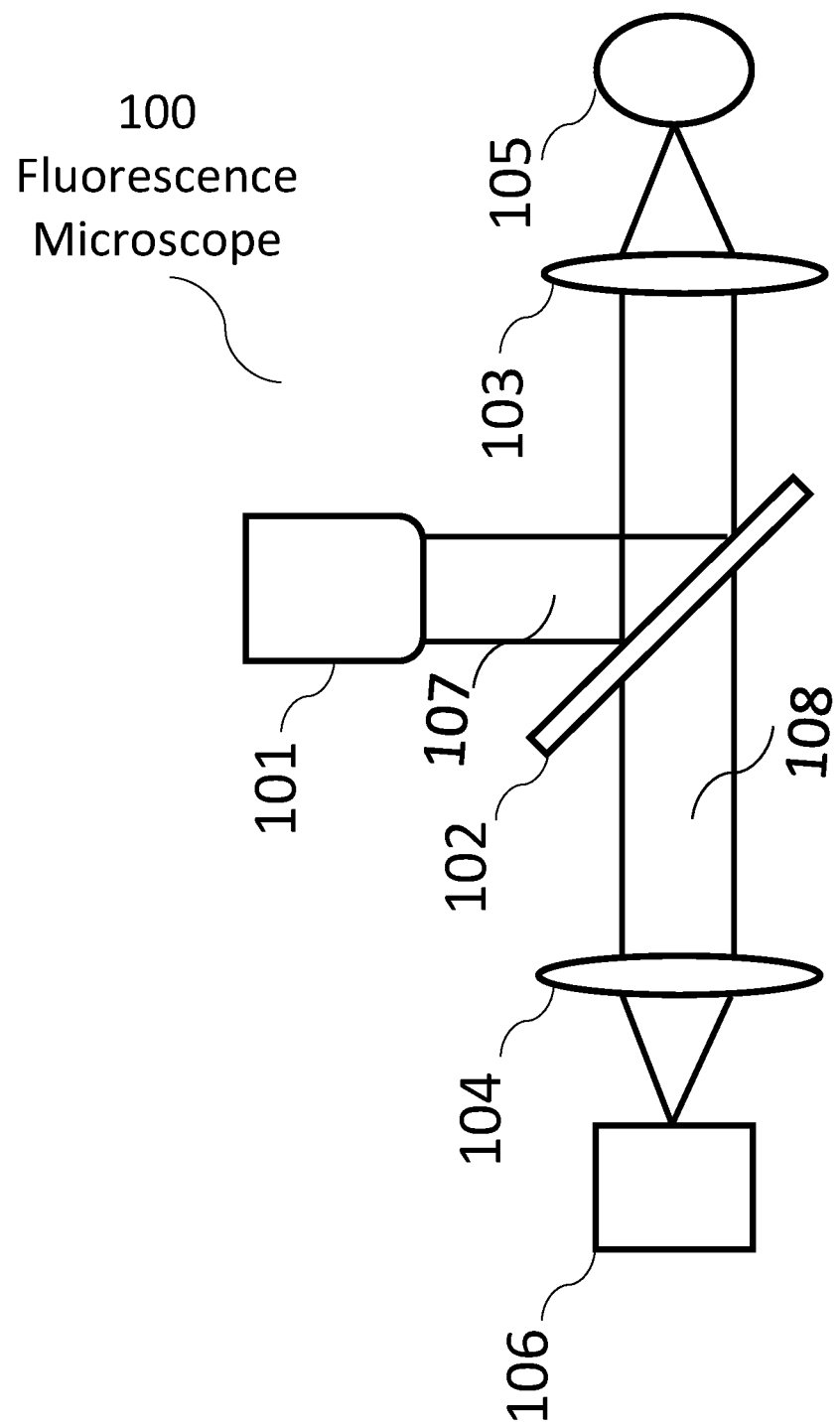
FIG. 15 An exemplary hyperspectral imaging system comprising an exemplary optics system, a fluorescence microscope. This system may generate an unmixed color image of a target by using an exemplary image forming system comprising features disclosed, for example in FIGS. 22-23.

An exemplary optics system comprising a fluorescence microscope 100 is shown in FIG. 15. This exemplary optics system may comprise at least one optical component. In this system, optical components may comprise an illumination source 101, a dichroic mirror/beam splitter 102, a first optical lens 103, a second optical lens 104, and a detector 106. These optical components may form a fluorescence microscope 100. This exemplary system may be suitable to form an image of a target 105. The source may generate an illumination source radiation 107. The dichroic mirror/beam splitter 102 may reflect the illumination wave to illuminate the target 105. The target, as a result, may emit an electromagnetic radiation (e.g. fluorescence) 108 and reflect back the illumination source radiation 107. The dichroic mirror/beam splitter 102 may filter the illumination source radiation from the target and may substantially prevent the illumination source radiation reflected from the target reaching the detector. The detected image of the target and the measured intensity of the target radiation by using these optical components may generate an unmixed color image of the target by using the system features/configurations of this disclosure. For example, this unmixed color image of the target may be generated by using any of the system features/configurations schematically shown in FIGS. 22-23.

Figure 16:
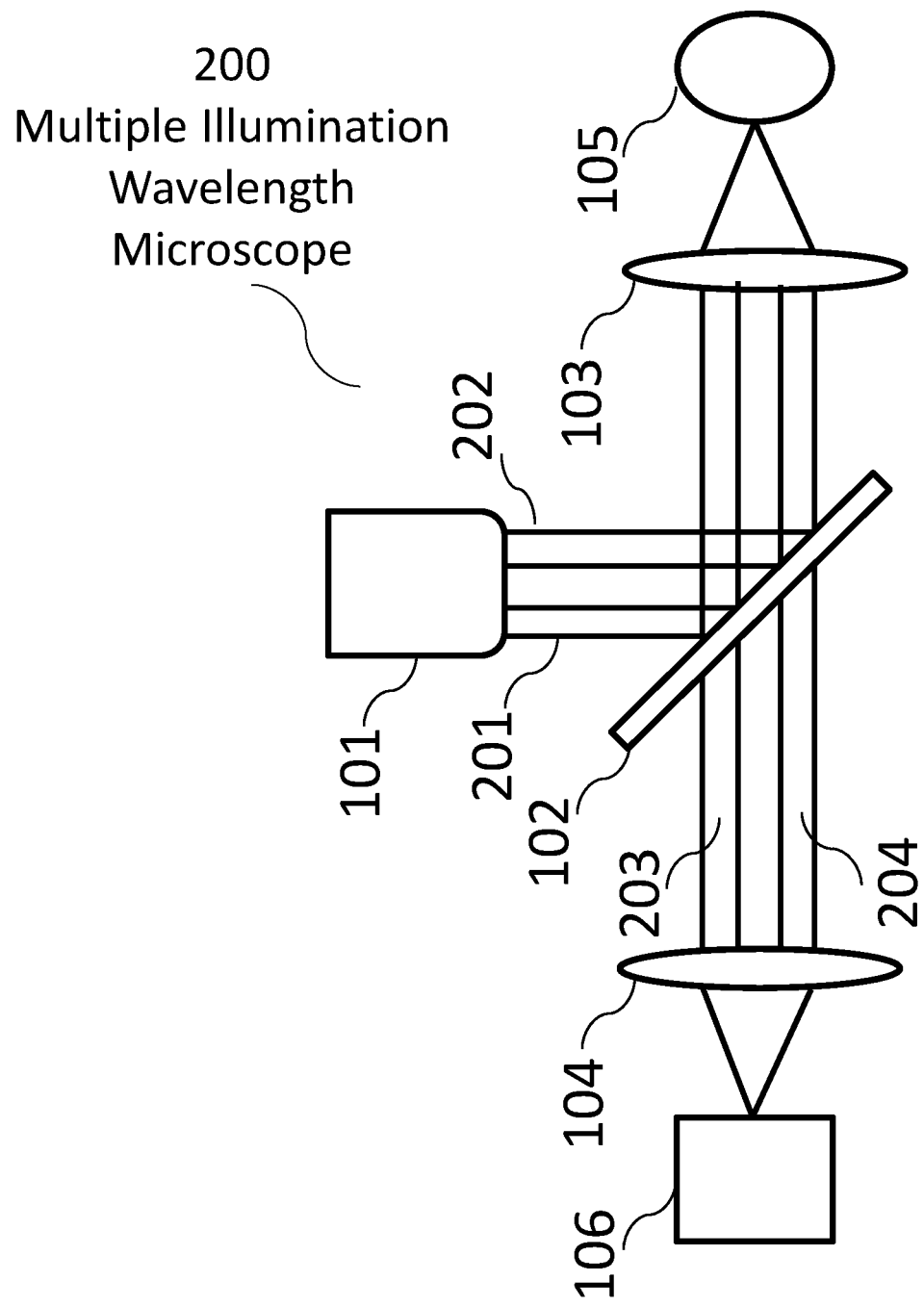
FIG. 16 An exemplary hyperspectral imaging system comprising an exemplary optics system, a multiple illumination wavelength microscope. This system may generate an unmixed color image of a target by using an exemplary image forming system comprising features disclosed, for example in FIGS. 22-23.

An exemplary optics system comprising a multiple illumination wavelength microscope 200 is shown in FIG. 16. This exemplary optics system may comprise at least one optical component. In this system, the optical components may comprise an illumination source 101, a dichroic mirror/beam splitter 102, a first optical lens 103, a second optical lens 104, and a detector 106. These optical components may form a hyperspectral imaging system comprising a fluorescence microscope, a reflectance microscope, or a combination thereof. This exemplary system may be suitable to form an image of a target 105. The illumination source may generate an illumination source radiation comprising multiple waves wherein each wave may have a different wavelength. For example, the illumination source in this example may generate an illumination source radiation comprising two waves each having a different wavelength, 201 and 202. The source may sequentially illuminate the target at each wavelength. The dichroic mirror/beam splitter 102 may reflect the illumination source, radiation to illuminate the target 105. The target, as a result, may emit and/or may reflect back a wave of the electromagnetic radiation. In one example, the dichroic mirror/beam splitter 102 may filter the electromagnetic radiation from the target and may substantially allow emitted radiation to reach the detector and substantially prevent the illumination source radiation reflected from the target reaching the detector. In another example, the dichroic mirror/beam splitter 102 may transmit only the reflected waves from the target, but substantially filter emitted waves from the target, thereby allowing only the reflected waves from the target to reach the detector. Yet in another example, the dichroic mirror/beam splitter 102 may transmit both the reflected radiation and emitted radiation from the target, thereby allowing both the reflected radiation and the reflected radiation from the target to reach the detector. In this example, multiple waves may reach the detector, each having a different wavelength. For example, the electromagnetic radiation reaching the detector may have two waves 203 and 204, each having a different wavelength. The detected image of the target and the measured intensity of the target radiation by using these optical components may generate an unmixed color image of the target by using the system features/configurations of this disclosure. For example, this unmixed color image of the target may be generated by using any of the system features/configurations schematically shown in FIGS. 22-23.

Figure 17:
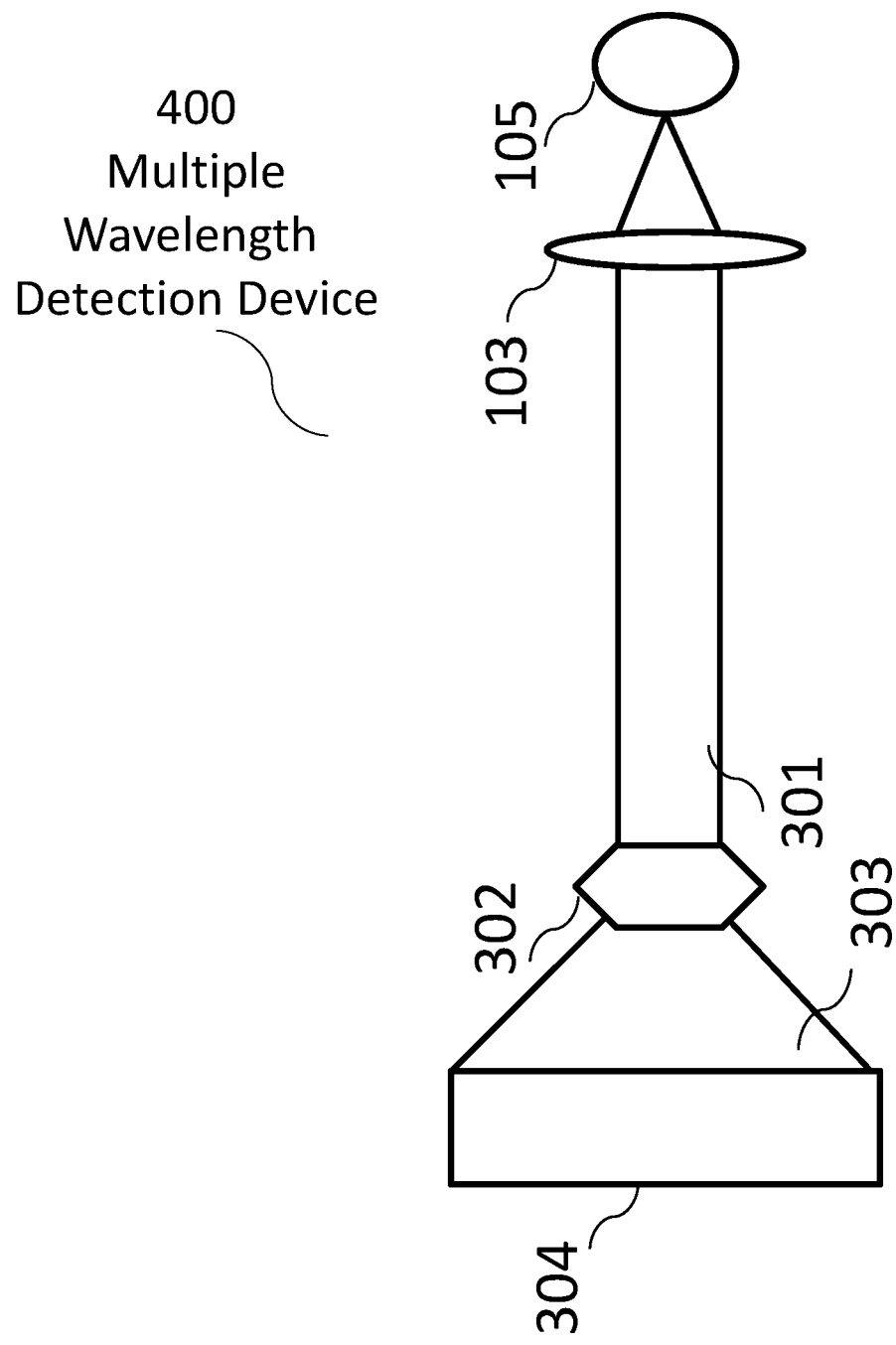
FIG. 17 An exemplary hyperspectral imaging system comprising an exemplary optics system, a multiple illumination wavelength device. This system may generate an unmixed color image of a target by using an exemplary image forming system comprising features disclosed, for example in FIGS. 22-23.

Another exemplary hyperspectral imaging system comprising a multiple wavelength detection microscope 300 is shown in FIG. 17. This exemplary hyperspectral imaging system may comprise at least one optical component. In this system, the optical components may comprise a first optical lens 103, a dispersive optic 302, and a detector array 304. These optical components may form a hyperspectral imaging system comprising a fluorescence device, a reflectance device, or a combination thereof. This exemplary system may be suitable to form an image of a target 105. The target may emit and/or may reflect a wave 301 of an electromagnetic radiation. In this example, at least one wave or at least two waves may reach the detector array. Each wave may have a different wavelength. The dispersive optic 302 may form a spectrally dispersed electromagnetic radiation 303. The detected image of the target and the measured intensity of the target radiation by using these optical components may generate an unmixed color image of the target by using the system features/configurations of this disclosure. For example, this unmixed color image of the target may be generated by using any of the system features/configurations schematically shown in FIGS. 22-23.

Figure 18:
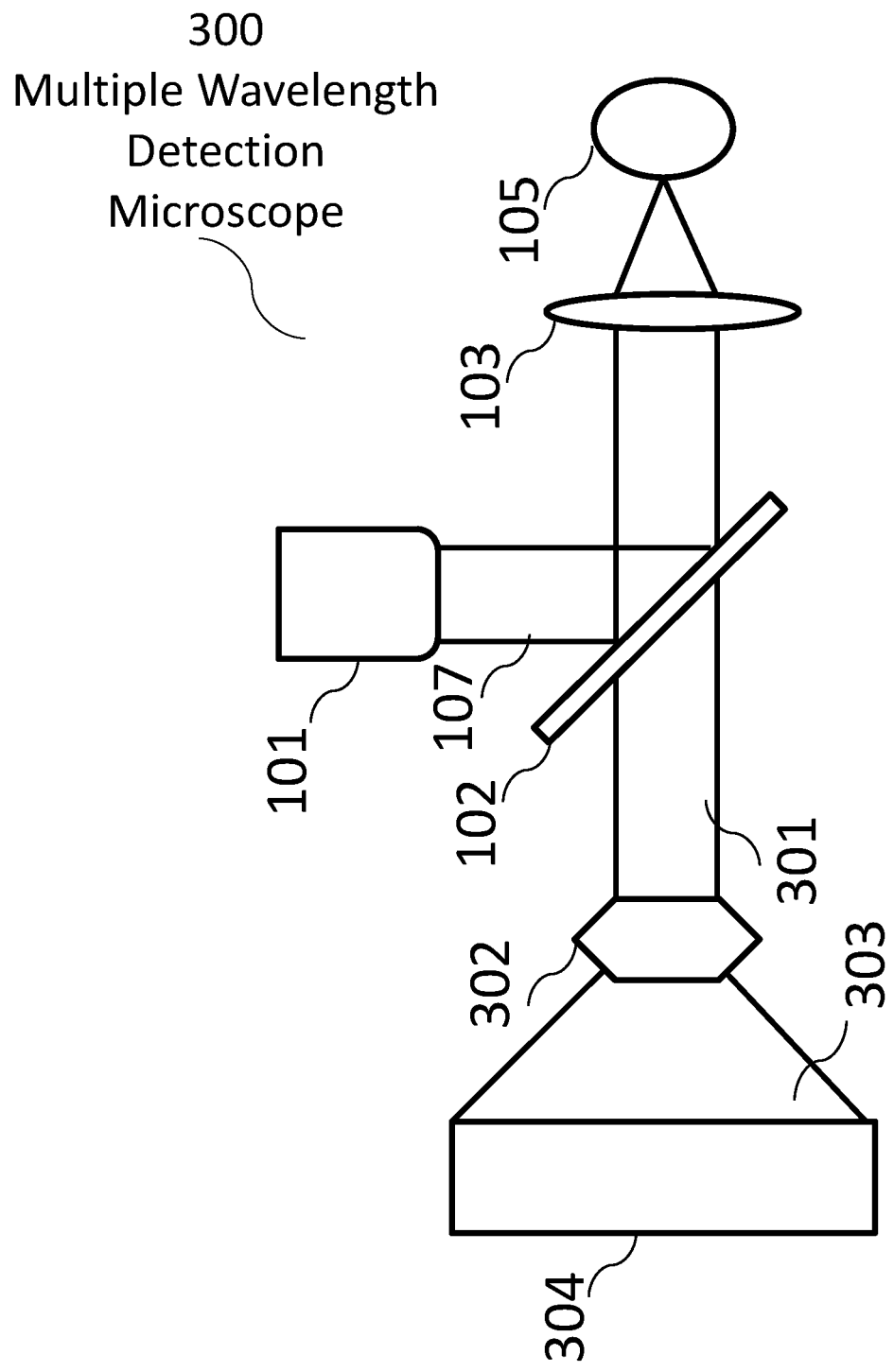
FIG. 18 An exemplary hyperspectral imaging system comprising an exemplary optics system, a multiple wavelength detection microscope. This system may generate an unmixed color image of a target by using an exemplary image forming system comprising features disclosed, for example in FIGS. 22-23.

Another exemplary hyperspectral imaging system comprising a multiple wavelength detection microscope 400 is shown in FIG. 18. This exemplary hyperspectral imaging system may comprise at least one optical component. In this system, the optical components may comprise an illumination source 101, a dichroic mirror/beam splitter 102, a first optical lens 103, a dispersive optic 302, and a detector array 304. These optical components may form a hyperspectral imaging system comprising a fluorescence device. This exemplary system may be suitable to form an image of a target 105. The illumination source may generate an illumination source radiation comprising at least one wave 107. Each wave may have a different wavelength. The source may sequentially illuminate the target at each wavelength. The dichroic mirror/beam splitter 102 may reflect the illumination wave to illuminate the target 105. The target, as a result, may emit a wave of the electromagnetic radiation. The dichroic mirror/beam splitter 102 may substantially allow the emitted wave 301 to reach the detector array, but may filter the target radiation and thereby substantially prevent the waves reflected from the target to reach the detector array. In this example, the emitted radiation reaching detector array may comprise multiple waves, each having a different wavelength. The dispersive optic 302 may form a spectrally dispersed electromagnetic radiation 303. The detected image of the target and the measured intensity of the target radiation by using these optical components may generate an unmixed color image of the target by using the system features disclosed above. For example, this unmixed color image of the target may be generated by using any of the system features schematically shown in FIGS. 22-23.

Figure 19:
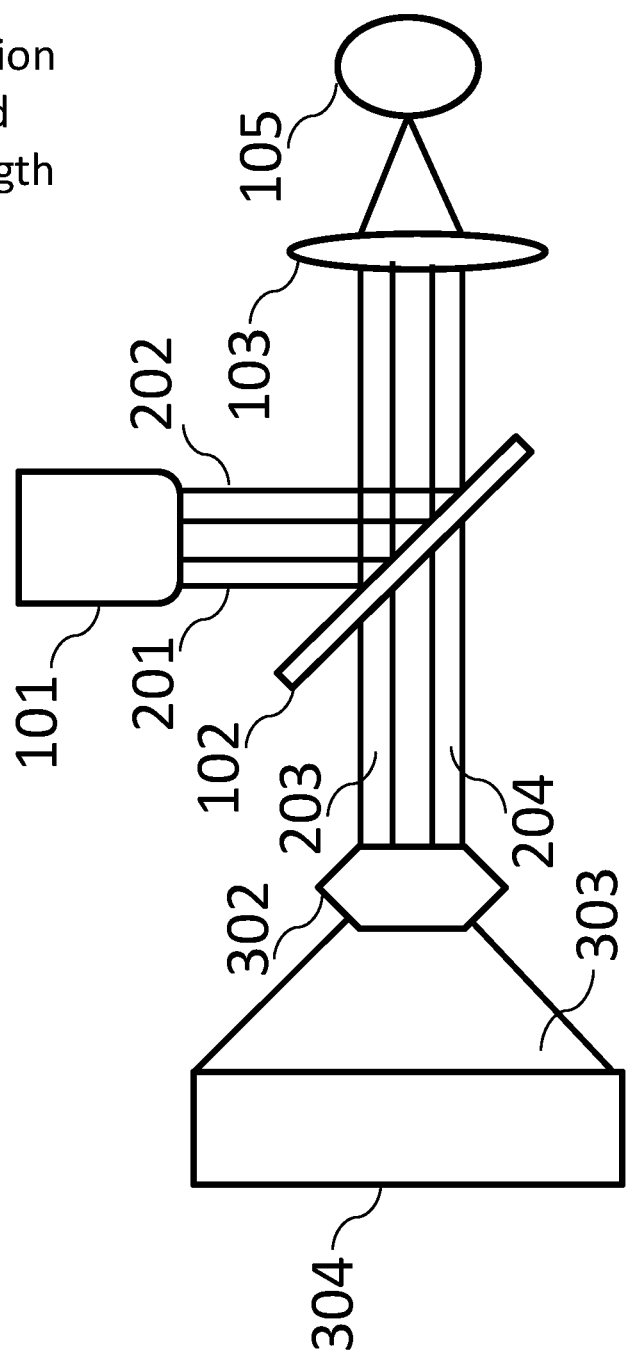
FIG. 19 An exemplary hyperspectral imaging system comprising an exemplary optics system, a multiple illumination wavelength and multiple wavelength detection microscope. This system may generate an unmixed color image of a target by using an exemplary image forming system comprising features disclosed, for example in FIGS. 22-23.

Another exemplary hyperspectral imaging system comprising a multiple illumination wavelength and multiple wavelength detection device 500 is shown in FIG. 19. This exemplary hyperspectral imaging system may comprise at least one optical component. In this system, the optical components may comprise an illumination source 101, a dichroic mirror/beam splitter 102, a first optical lens 103, a dispersive optic 302, and a detector array 304. These optical components may form a hyperspectral imaging system comprising a fluorescence microscope, a reflectance microscope, or a combination thereof. This exemplary system may be suitable to form an image of a target 105. The source may generate an illumination wave comprising multiple waves wherein each wave may have a different wavelength. For example, the illumination source in this example may generate an illumination source radiation comprising two waves each having a different wavelength, 201 and 202. The illumination source may sequentially illuminate the target at each wavelength. The dichroic mirror/beam splitter 102 may reflect the illumination radiation to illuminate the target 105. The target, as a result, may emit and/or may reflect back the electromagnetic radiation. In one example, the dichroic mirror/beam splitter 102 may filter the radiation from the target substantially allowing only emitted radiation reaching the detector array, but substantially preventing the radiation reflected from the target to reach the detector array. In another example, the dichroic mirror/beam splitter 102 may transmit only the reflected waves from the target, but substantially filter emitted waves from the target, thereby substantially allowing only the reflected waves from the target to reach the detector array. Yet in another example, the dichroic mirror/beam splitter 102 may substantially transmit both the reflected waves and emitted waves from the target, thereby allowing both the reflected waves and the reflected beams from the target to reach the detector array. In this example, the beam reaching detector array may have multiple waves, each having a different wavelength. For example, the beam reaching the detector array may have two waves 203 and 204, each having a different wavelength. The dispersive optic 302 may form a spectrally dispersed electromagnetic radiation 303. The detected image of the target and the measured intensity of the target radiation by using these optical components may generate an unmixed color image of the target by using the system features/configurations of this disclosure. For example, this unmixed color image of the target may be generated by using any of the system features/configurations schematically shown in FIGS. 22-23.

Figure 20:
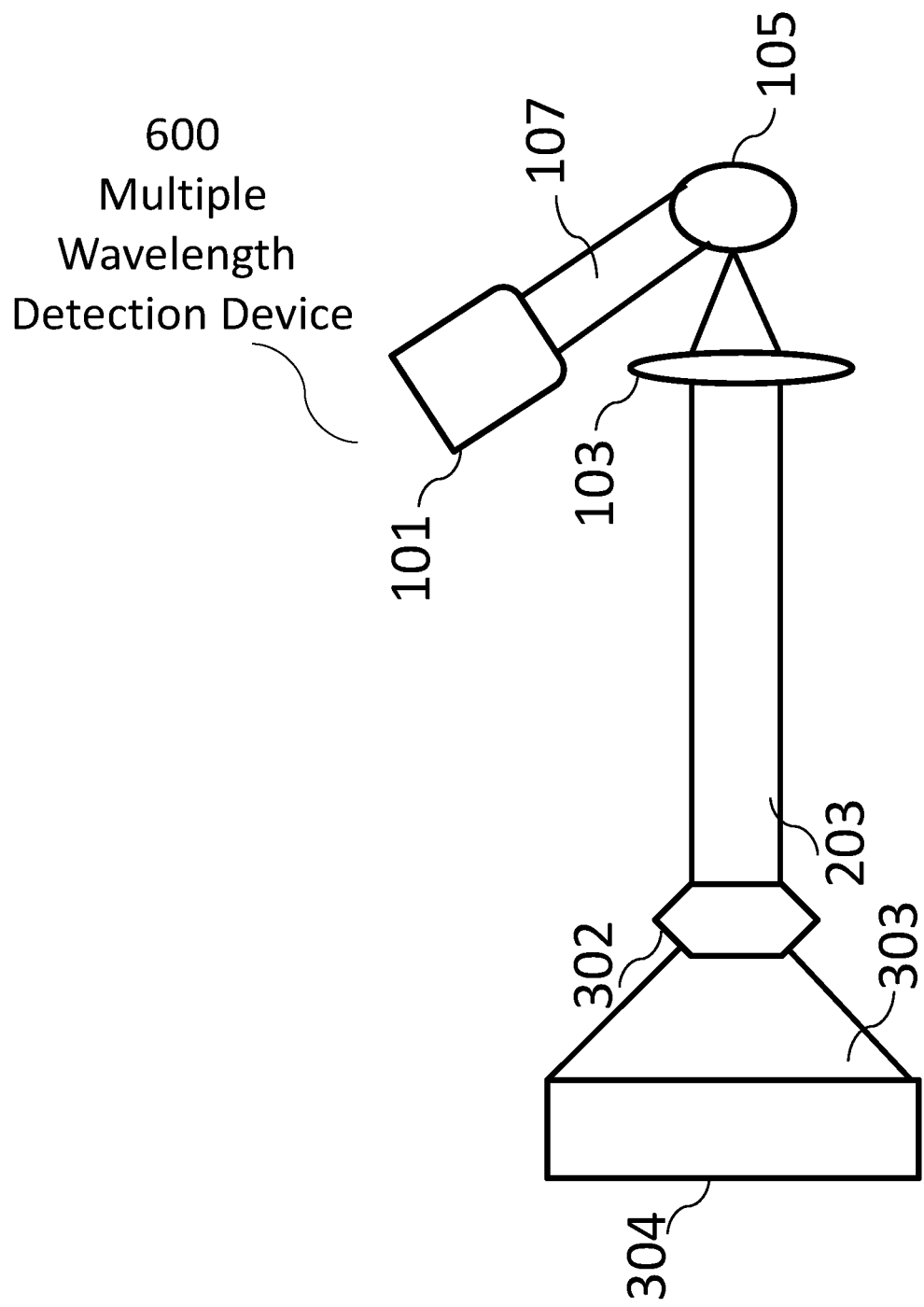
FIG. 20 An exemplary hyperspectral imaging system comprising an exemplary optics system, a multiple wavelength detection device. This system may generate an unmixed color image of a target by using an exemplary image forming system comprising features disclosed, for example in FIGS. 22-23.

Another exemplary optical system comprising a multiple wavelength detection device 600 is shown in FIG. 20. This exemplary optical system may comprise at least one optical component. In this system, the optical components may comprise an illumination source 101, a first optical lens 103, a dispersive optic 302, and a detector array 304. These optical components may form a hyperspectral imaging system comprising a fluorescence and/or reflectance device. This exemplary system may be suitable to form an image of a target 105. The illumination source may generate an illumination source radiation comprising at least one wave 107. Each wave may have a different wavelength. The source may sequentially illuminate the target at each wavelength. The target, as a result, may emit, reflect, refract, and/or absorb a beam 203 of the electromagnetic radiation. In this example, the emitted, reflected, refracted, and/or absorbed beam reaching detector array may comprise multiple waves, each having a different wavelength. The dispersive optic 302 may form a spectrally dispersed electromagnetic radiation 303. The detected image of the target and the measured intensity of the target radiation by using these optical components may generate an unmixed color image of the target by using the system features/configurations of this disclosure. For example, this unmixed color image of the target may be generated by using any of the system features/configurations schematically shown in FIGS. 22-23.

Figure 21:
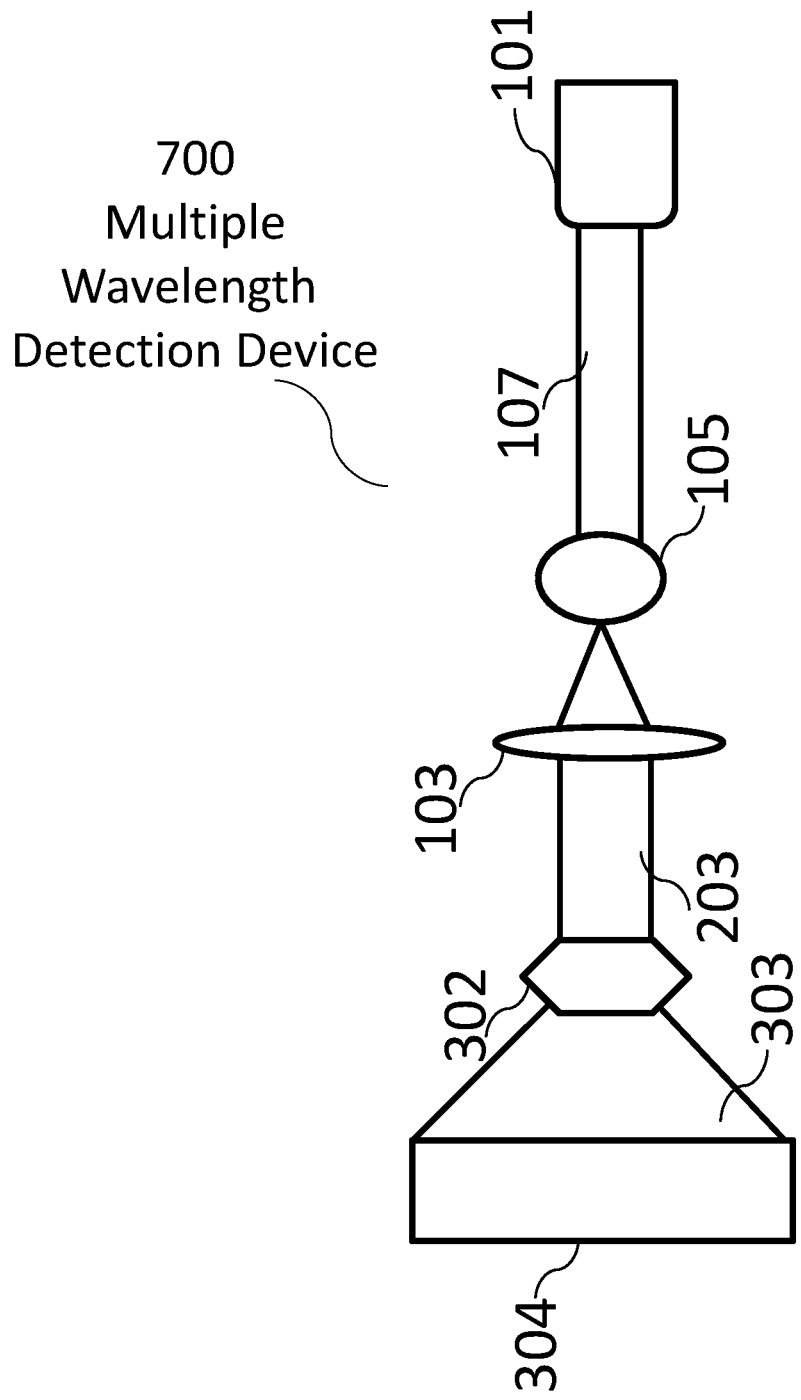
FIG. 21 An exemplary hyperspectral imaging system comprising an exemplary optics system, a multiple wavelength detection device. This system may generate an unmixed color image of a target by using an exemplary image forming system comprising features disclosed, for example in FIGS. 22-23.

Another exemplary optics system comprising a multiple wavelength detection device 700 is shown in FIG. 21. This optics system may comprise at least one optical component. In this system, the optical components may comprise an illumination source 101, a first optical lens 103, a dispersive optic 302, and a detector array 304. These optical components may form a hyperspectral imaging system comprising a fluorescence and/or reflectance device. This exemplary system may be suitable to form an image of a target 105. The illumination source may generate an illumination source radiation comprising at least one wave 107. Each wave may have a different wavelength. The source may sequentially illuminate the target at each wavelength. The target, as a result, may emit, transmit, refract, and/or absorb a beam 203 of the electromagnetic radiation. In this example, the emitted, transmitted, refracted, and/or absorbed electromagnetic radiation reaching detector array may comprise multiple waves, each having a different wavelength. The dispersive optic 302 may form a spectrally dispersed electromagnetic radiation 303. The detected image of the target and the measured intensity of the target radiation by using these optical components may generate an unmixed color image of the target by using the system features/configurations of this disclosure. For example, this unmixed color image of the target may be generated by using any of the system features/configurations schematically shown in FIGS. 22-23.

In this disclosure, the image forming system may comprise a control system 40, a hardware processor 50, a memory system 60, a display 70, or a combination thereof. An exemplary image forming system is shown in FIG. 14. The control system may be any control system. For example, the control system may be configured to control the optics system. For example, the control system may be configured to control at least one optical component of the optics system. For example, the control system may be configured to control the at least one optical detector to detect target radiation, detect the intensity and the wavelength of each target wave, transmit the detected intensity and wavelength of each target wave to the image forming system, and display the unmixed color image of the target. For example, the control system may be configured to control motions of the optical components, for example, opening and closure of optical shutters, motions of mirrors, and the like. The hardware processor may be any hardware processor. For example, the hardware processor may be configured to form the target image, perform phasor analysis, perform the Fourier transform of the intensity spectrum, apply the denoising filter, form the phasor plane, map back the phasor point(s), assigns the arbitrary color(s), generate the unmixed color image of the target, the like, or a combination of such configurations thereof. The memory system may be any memory system. For example, the memory system may be configured to receive and store inputs from the hardware processor. These inputs, for example, may be the target image, the target radiation, the intensity spectrum, the phasor plane, the unmixed color image of the target, the like, or a combination of such configurations. For example, the memory system may be configured to provide outputs to other components of the image forming system, for example, to the processor and/or the display. These outputs, for example, may be the target image, the target radiation, the intensity spectrum, the phasor plane, the unmixed color image of the target, the like, or a combination of such configurations. The display may be any display. For example, the display may be configured to display the target image, the intensity spectrum, the phasor plane, the unmixed color image of the target, the like, or a combination of such configurations.

In this disclosure, the image forming system may have a configuration that causes the optical detector to detect the target radiation and to transmit the detected intensity and wavelength of each target wave to the image forming system.

In this disclosure, the image forming system may have a configuration that acquires the detected target radiation comprising the at least two target waves.

In this disclosure, the image forming system may have a configuration that acquires a target radiation comprising at least two target waves, each wave having an intensity and a different wavelength.

In this disclosure, the image forming system may have a configuration that acquires a target image, wherein the target image comprises at least two pixels, and wherein each pixel corresponds to one physical point on the target.

In this disclosure, the image forming system may have a configuration that forms an image of the target using the detected target radiation ("target image"). The target image may comprise at least one pixel. The target image may comprise at least two pixels. Each pixel corresponds to one physical point on the target.

In this disclosure, the target image may be formed/acquired in any form. For example, the target image may have a visual form and/or a digital form. For example, the formed/acquired target image may be a stored data. For example, the formed/acquired target image may be stored in the memory system as data. For example, the formed/acquired target image may be displayed on the image forming system's display. For example, the formed/acquired target image may be an image printed on a paper or any similar media.

In this disclosure, the image forming system may have a configuration that forms at least one spectrum for each pixel using the detected intensity and wavelength of each target wave ("intensity spectrum").

In this disclosure, the image forming system may have a configuration that acquires at least one intensity spectrum for each pixel, wherein the intensity spectrum comprises at least two intensity points.

In this disclosure, the intensity spectrum may be formed/acquired in any form. For example, the intensity spectrum may have a visual form and/or a digital form. For example, the formed/acquired intensity spectrum may be a stored data. For example, the formed/acquired intensity spectrum may be stored in the memory system as data. For example, the formed/acquired intensity spectrum may be displayed on the image forming system's display. For example, the formed/acquired intensity spectrum may be an image printed on a paper or any similar media.

In this disclosure, the image forming system may have a configuration that transforms the formed intensity spectrum of each pixel using a Fourier transform into a complex-valued function based on the intensity spectrum of each pixel, wherein each complex-valued function has at least one real component and at least one imaginary component.

In this disclosure, the image forming system may have a configuration that applies a denoising filter on both the real component and the imaginary component of each complex-valued function at least once so as to produce a denoised real value and a denoised imaginary value for each pixel.

In this disclosure, the image forming system may have a configuration that forms one point on a phasor plane ("phasor point") for each pixel by plotting the denoised real value against the denoised imaginary value of each pixel. The image forming system may form the phasor plane, for example, by using its hardware components, for example, the control system, the hardware processor, the memory or a combination thereof. The image forming system may display the phasor plane.

In this disclosure, the phasor point and/or phasor plane may be formed/acquired in any form. For example, the phasor point and/or phasor plane may have a visual form and/or a digital form. For example, the formed/acquired phasor point and/or phasor plane may be a stored data. For example, the formed/acquired phasor point and/or phasor plane may be stored in the memory system as data. For example, the formed/acquired phasor point and/or phasor plane may be displayed on the image forming system's display. For example, the formed/acquired phasor point and/or phasor plane may be an image printed on a paper or any similar media.

In this disclosure, the image forming system may have a configuration that maps back the phasor point to a corresponding pixel on the target image based on the phasor point's geometric position on the phasor plane. In this disclosure, the image forming system may have a configuration that maps back the phasor plane to the corresponding target image based on each phasor point's geometric position on the phasor plane. The image forming system may map back the phasor point, for example, by using its hardware components, for example, the control system, the hardware processor, the memory or a combination thereof.

In this disclosure, the phasor point and/or phasor plane may be mapped back in any form. For example, the mapped back phasor point and/or phasor plane may have a visual form and/or a digital form. For example, the mapped back phasor point and/or phasor plane may be a stored data. For example, the mapped back phasor point and/or phasor plane may be stored in the memory system as data. For example, the mapped back phasor point and/or phasor plane may be displayed on the image forming system's display. For example, the mapped back phasor point and/or phasor plane may be an image printed on a paper or any similar media.

In this disclosure, the image forming system may have a configuration that assigns an arbitrary color to the corresponding pixel based on the geometric position of the phasor point on the phasor plane.

In this disclosure, the image forming system may have a configuration that generates an unmixed color image of the target based on the assigned arbitrary color.

In this disclosure, the unmixed color image may be formed in any form. For example, the unmixed color image may have a visual form and/or a digital form. For example, the unmixed color image may be a stored data. For example, the unmixed color image may be stored in the memory system as data. For example, the unmixed color image may be displayed on the image forming system's display. For example, the unmixed color image may be an image printed on a paper or any similar media.

In this disclosure, the image forming system may have a configuration that displays the unmixed color image of the target on the image forming system's display.

In this disclosure, the image forming system may have any combination of above configurations.

In this disclosure, the image forming system may be configured to use at least one harmonic of the Fourier transform to generate the unmixed color image of the target. The image forming system may be configured to use at least a first harmonic of the Fourier transform to generate the unmixed color image of the target. The image forming system may be configured to use at least a second harmonic of the Fourier transform to generate the unmixed color image of the target. The image forming system may be configured to use at least a first harmonic and a second harmonic of the Fourier transform to generate the unmixed color image of the target.

In this disclosure, the denoising filter may be any denoising filter. For example, the denoising filter may be a denoising filter such that when the denoising filter is applied, the image quality is not compromised. For example, when the denoising filter is applied, the detected electromagnetic radiation intensity at each pixel in the image may not change. An example of a suitable denoising filter may comprise a median filter.

In this disclosure, the unmixed color image of the target may be formed at a signal-to-noise ratio of the at least one spectrum in the range of 1.2 to 50. The unmixed color image of the target may be formed at a signal-to-noise ratio of the at least one spectrum in the range of 2 to 50.

In one example, an exemplary hyperspectral imaging system for generating an unmixed color image of a target may comprise an optics system and an image forming system. The optics system may comprise at least one optical component. The at least one optical component may comprise at least one optical detector. The at least one optical detector may have a configuration that detects electromagnetic radiation absorbed, transmitted, refracted, reflected, and/or emitted ("target radiation") by at least one physical point on the target, the target radiation comprises at least two waves ("target waves"), each wave having an intensity and a different wavelength; detects the intensity and the wavelength of each target wave; and transmits the detected target radiation, and each target wave's detected intensity and wavelength to the image forming system. The image forming system may comprise a control system, a hardware processor, a memory, and a display. The image forming system may have a configuration that forms an image of the target using the detected target radiation ("target image"), wherein the target image comprises at least two pixels, and wherein each pixel corresponds to one physical point on the target; forms at least one spectrum for each pixel using the detected intensity and wavelength of each target wave ("intensity spectrum"); transforms the formed intensity spectrum of each pixel using a Fourier transform into a complex-valued function based on the intensity spectrum of each pixel, wherein each complex-valued function has at least one real component and at least one imaginary component; applies a denoising filter on both the real component and the imaginary component of each complex-valued function at least once so as to produce a denoised real value and a denoised imaginary value for each pixel; forms one point on a phasor plane ("phasor point") for each pixel by plotting the denoised real value against the denoised imaginary value of each pixel; maps back the phasor point to a corresponding pixel on the target image based on the phasor point's geometric position on the phasor plane; assigns an arbitrary color to the corresponding pixel based on the geometric position of the phasor point on the phasor plane; generates an unmixed color image of the target based on the assigned arbitrary color; and displays the unmixed color image of the target on the image forming system's display.

In one example, the image forming system may have a configuration that causes the optical detector to detect the target radiation and to transmit the detected intensity and wavelength of each target wave to the image forming system. This image forming system may acquire the detected target radiation comprising the at least two target waves; form an image of the target using the detected target radiation ("target image"), wherein the target image comprises at least two pixels, and wherein each pixel corresponds to one physical point on the target; forms at least one spectrum for each pixel using the detected intensity and wavelength of each target wave ("intensity spectrum"); transform the formed intensity spectrum of each pixel using a Fourier transform into a complex-valued function based on the intensity spectrum of each pixel, wherein each complex-valued function has at least one real component and at least one imaginary component; apply a denoising filter on both the real component and the imaginary component of each complex-valued function at least once so as to produce a denoised real value and a denoised imaginary value for each pixel; form one point on a phasor plane ("phasor point") for each pixel by plotting the denoised real value against the denoised imaginary value of each pixel; map back the phasor point to a corresponding pixel on the target image based on the phasor point's geometric position on the phasor plane; assign an arbitrary color to the corresponding pixel based on the geometric position of the phasor point on the phasor plane; and generate an unmixed color image of the target based on the assigned arbitrary color. This image forming system may have a further configuration that displays the unmixed color image of the target on the image forming system's display.

In another example, the image forming system may have a configuration that acquires a target radiation comprising at least two target waves, each wave having an intensity and a different wavelength; forms a target image, wherein the target image comprises at least two pixels, and wherein each pixel corresponds to one physical point on the target; forms at least one intensity spectrum for each pixel using the intensity and the wavelength of each target wave; transforms the formed intensity spectrum of each pixel using a Fourier transform into a complex-valued function based on the intensity spectrum of each pixel, wherein each complex-valued function has at least one real component and at least one imaginary component; applies a denoising filter on both the real component and the imaginary component of each complex-valued function at least once so as to produce a denoised real value and a denoised imaginary value for each pixel; forms one phasor point for each pixel by plotting the denoised real value against the denoised imaginary value of each pixel; maps back the phasor point to a corresponding pixel on the target image based on the phasor point's geometric position on the phasor plane; assigns an arbitrary color to the corresponding pixel based on the geometric position of the phasor point on the phasor plane; and generates an unmixed color image of the target based on the assigned arbitrary color. This exemplary image forming system may have a further configuration that displays the unmixed color image of the target on the image forming system's display.

In another example, the image forming system may have a configuration that acquires a target image, wherein the target image comprises at least two pixels, and wherein each pixel corresponds to one physical point on the target; acquires at least one intensity spectrum for each pixel, wherein the intensity spectrum comprises at least two intensity points; transforms the intensity spectrum of each pixel using a Fourier transform into a complex-valued function based on the intensity spectrum of each pixel, wherein each complex-valued function has at least one real component and at least one imaginary component; applies a denoising filter on both the real component and the imaginary component of each complex-valued function at least once so as to produce a denoised real value and a denoised imaginary value for each pixel; forms one phasor point for each pixel by plotting the denoised real value against the denoised imaginary value of each pixel; maps back the phasor point to a corresponding pixel on the target image based on the phasor point's geometric position on the phasor plane; assigns an arbitrary color to the corresponding pixel based on the geometric position of the phasor point on the phasor plane; and generates an unmixed color image of the target based on the assigned arbitrary color. This exemplary image forming system may have a further configuration that displays the unmixed color image of the target on the image forming system's display.

One example of the hyperspectral imaging system is schematically shown in FIG. 22. In this example, the imaging system may obtain an image of a target 401. The image may comprise at least two waves and at least two pixels. The system may form an image of the target using intensities of each wave ("intensity spectrum") 402. The system may transform the intensity spectrum of each pixel by using a Fourier transform 403, thereby forming a complex-valued function based on the detected intensity spectrum of each pixel. Each complex-valued function may have at least one real component 404 and at least one imaginary component 405. The system may apply a denoising filter 406 on both the real component and the imaginary component of each complex-valued function at least once. The system may thereby obtain a denoised real value and a denoised imaginary value for each pixel. The system may plot the denoised real value against the denoised imaginary value for each pixel. The system may thereby form a point on a phasor plane 407. The system may form at least one additional point on the phasor plane by using at least one more pixel of the image. The system may select at least one point on the phasor plane, based on its geometric position on the phasor plane. The system may map back 408 the selected point on the phasor plane to corresponding pixel on the image of the target and may assign a color to the corresponding pixel, and wherein the color is assigned based on the geometric position of the point on the phasor plane. As a result, the system may thereby generate an unmixed color image of the target 409.

Another example of the hyperspectral imaging system is schematically shown in FIG. 23. In this example, the hyperspectral imaging system further comprises at least one detector 106 or a detector array 304. This imaging system may form an image of a target 401 by using the detector or the detector array. The image may comprise at least two waves and at least two pixels. The system may form an image of the target using intensities of each wave ("intensity spectrum") 402. The system may transform the intensity spectrum of each pixel by using a Fourier transform 403, thereby forming a complex-valued function based on the detected intensity spectrum of each pixel. Each complex-valued function may have at least one real component 404 and at least one imaginary component 405. The system may apply a denoising filter 406 on both the real component and the imaginary component of each complex-valued function at least once. The system may thereby obtain a denoised real value and a denoised imaginary value for each pixel. The system may plot the denoised real value against the denoised imaginary value for each pixel. The system may thereby form a point on a phasor plane 407. The system may form at least one additional point on the phasor plane by using at least one more pixel of the image. The system may select at least one point on the phasor plane, based on its geometric position on the phasor plane. The system may map back 408 the selected point on the phasor plane to corresponding pixel on the image of the target and may assign a color to the corresponding pixel, and wherein the color is assigned based on the geometric position of the point on the phasor plane. As a result, the system may thereby generate an unmixed color image of the target 409.

In this disclosure, the target may be any target. The target may be any target that has a specific spectrum of color. For example, the target may be a tissue, a fluorescent genetic label, an inorganic target, or a combination thereof.

In this disclosure, the system may be calibrated by using a reference to assign colors to each pixel. The reference may be any known reference. For example, the reference may be any reference wherein unmixed color image of the reference is determined prior to the generation of unmixed color image of the target. For example, the reference may be a physical structure, a chemical molecule, a biological molecule, a biological activity (e.g. physiological change) as a result of physical structural change and/or disease.

In this disclosure, the target radiation may comprise fluorescence. The hyperspectral imaging system suitable for fluorescence detection may comprise an optical filtering system. Examples of the optical filtering system are: a first optical filter to substantially decrease the intensity of the source radiation reaching to the detector. The first optical filter may be placed between the target and the detector. The first optical filter may be any optical filter. Examples of the first optical filter may be dichroic filter, a beam splitter type filter, or a combination thereof.

In this disclosure, the hyperspectral imaging system suitable for fluorescence detection may further comprise a second optical filter. The second optical filter may be placed between the first optical filter and the detector to further decrease the intensity of the source radiation reaching the detector. The second optical filter may be any optical filter. Examples of the second optical filter may be a notch filter, an active filter, or a combination thereof. Examples of the active filter may be an adaptive optical system, an acousto-optic tunable filter, a liquid crystal tunable bandpass filter, a Fabry-Perot interferometric filter, or a combination thereof.

In this disclosure, the hyperspectral imaging system may be calibrated by using a reference material to assign colors to each pixel. The reference material may be any known reference material. For example, the reference material may be any reference material wherein unmixed color image of the reference material is determined prior to the generation of unmixed color image of the target. For example, the reference material may be a physical structure, a chemical molecule (i.e. compound), a biological activity (e.g. physiological change) as a result of physical structural change and/or disease. The chemical compound may be any chemical compound. For example, the chemical compound may be a biological molecule (i.e. compound).

In this disclosure, the hyperspectral imaging system may be used to diagnose any health condition. For example, the hyperspectral imaging system may be used to diagnose any health condition of any mammal. For example, the hyperspectral imaging system may be used to diagnose any health condition of a human. Examples of the health condition may comprise a disease, a congenital malformation, a disorder, a wound, an injury, an ulcer, an abscess, or the like. The health condition may be related to a tissue. The tissue may be any tissue. For example, the tissue may comprise a skin. Examples of a health condition related to a skin or tissue may be a skin lesion. The skin lesion may be any skin lesion. Examples of the skin lesion may be a skin cancer, a scar, an acne formation, a wart, a wound, an ulcer, or the like. Other examples of a health condition of a skin or tissue may be a makeup of a tissue or a skin, for example, the tissue or the skin's moisture level, oiliness, collagen content, hair content, or the like.

In this disclosure, the target may comprise a tissue. The hyperspectral imaging system may display an unmixed color image of the tissue. The health condition may cause differentiation of chemical composition of the tissue. This chemical composition may be related to chemical compounds such as hemoglobin, melanin, a protein (e.g. collagen), oxygen water, the like, or a combination thereof. Due to the differentiation of the tissue's chemical composition, color of the tissue that is affected by the health condition may appear to be different than that of the tissue that is not affected by the health condition. Because of such color differentiation, the health condition of the tissue may be diagnosed. The hyperspectral imaging system may therefore allow a user to diagnose, for example, a skin condition, regardless of room lighting and skin pigmentation level.

For example, an illumination source radiation delivered to a biological tissue may undergo multiple scattering from inhomogeneity of biological structures and absorption by chemical compounds such as hemoglobin, melanin, and water present in the tissue as the electromagnetic radiation propagates through the tissue. For example, absorption, fluorescence, and scattering characteristics of the tissue may change during the progression of a disease. For example, therefore, the reflected, fluorescent, and transmitted light from tissue detected by the optical detector of the hyperspectral imaging of this disclosure may carry quantitative diagnostic information about tissue pathology.

The diagnosis of the health condition may be performed by any user, including a physician, a medical staff, or a consumer.

The diagnostic information, obtained by using the hyperspectral imaging system, may determine the health condition of the tissue. As such, this diagnostic information may enhance a patient's clinical outcome, for example, before, during, and/or after surgery or treatment. This hyperspectral imaging system, for example, may be used to track a patient's evolution of health over time by determining the health condition of, for example, the tissue of the patient. In this disclosure, the patient may be any mammal. For example, the mammal may be a human.

In this disclosure, the reference material disclosed above may be used in the diagnosis of the health condition.

In this disclosure, the hyperspectral imaging system comprising HySP may be configured to apply Fourier transform to convert all photons collected across spectrum into one point in the two dimensional (2D) phasor plot ("density plot"). The reduced dimensionality may perform well in low SNR regime compared to linear unmixing method, where each channel's error may contribute to the fitting result. In any imaging system, the number of photons emitted by a dye during a time interval may be a stochastic (Poissonian) process, where the signal (total digital counts) may scale as the average number of acquired photons, N; and the noise may scale as square-root of N, $\sqrt{N}$. Such Poissonian noise of the fluorescence emission and the detector readout noise may become more significant at lower light levels. First, the error on HySP plots may be quantitatively assessed. Then, this information may be used to develop a noise reduction approach to demonstrate that the hyperspectral imaging system comprising HySP is a robust system for resolving time-lapse hyper-spectral fluorescent signals in vivo in a low SNR regime.

The following features are also within the scope of this disclosure.

For each pixel in a dataset, the Fourier coefficients of its normalized spectra may define the coordinates of its phasor point (z(n)), with n the harmonic number (Equation 1, below). The Sine and Cosine transforms here may be used to guarantee that two normalized identical spectra yield identical phasor points (FIG. 1b, inset). When these transforms are applied to real data, the system (for example, the system comprising a microscope) may have multiple sources of noise that might affect the exact coordinates of the phasor point. Poissonian and detector noise in each spectral bin may cause a scatter of points on phasor plot, which is called scatter error, (std{z(n)}) hereafter. In addition, compromised SNR and signal saturation may alter the mean position of the scatter distribution itself, which is called shifted-mean error hereafter.

Figure 1A:
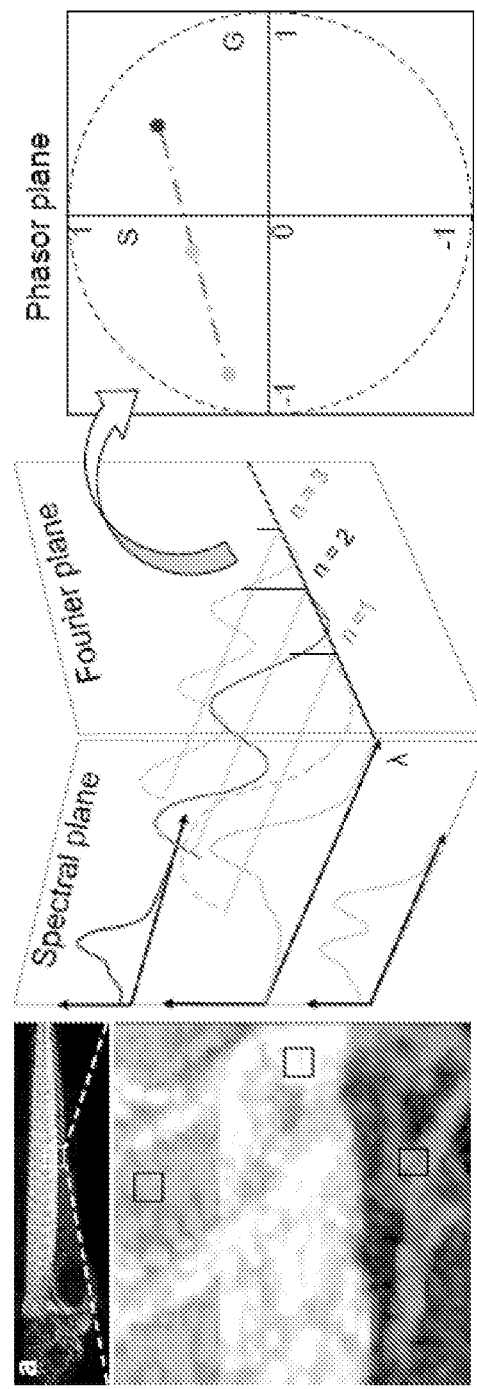
FIG. 1 Hyper-Spectral Phasor analysis. (a) Schematic principle of the HySP method. Spectra from every voxel in the multi-dimensional (x,y,z,λ) dataset are represented in terms of its Fourier coefficients (harmonics, n). Typically, n=2 is chosen and the corresponding coefficients are represented on the phasor plot (for other harmonics, see FIG. 5f). (b) Representative recordings of fluorescein (about 5 μM in ethanol) spectra at a fixed gain value (about 800) but varying laser power (about 1% to about 60%). The error bars denote the variation in intensity values over 10 measurements. Color coding represents intensities, blue for low-intensities and red for high-intensities. The inset shows that when normalized, emissions spectra overlap, provided recordings are made below the saturation limit of the detector. Imaging was done on Zeiss LSM780 equipped with QUASAR detector. (c) Scatter error ($\varepsilon_\sigma$) on phasor plot, resulting from the Poissonian noise in recording of a spectrum, is defined as the standard deviation of the scatter around expected phasor value ($z_e(n)$). Inset shows the 3D histogram of the distribution of phasor points around $z_e$. (d) Shifted-mean error ($\varepsilon_\mu$) on phasor plot result from changes in the shape of normalized spectrum that move the mean phasor point away from the true phasor coordinates corresponding to a given spectrum. (e) Scatter error, varies inversely with the number of total digital counts, being most sensitive to the detector gain. The legend is applicable to (e) and (f). (f) Normalized shifted-mean error remains nearly constant and below 5% over a large range of total digital counts form different imaging parameters. In an effort to understand which error is dominating, ratios of the two errors were plotted (inset). The ratio shows that scatter error ($\varepsilon_\sigma$) is almost an order of magnitude higher than the shifted-mean error ($\varepsilon_\mu$).
Figure 1B:
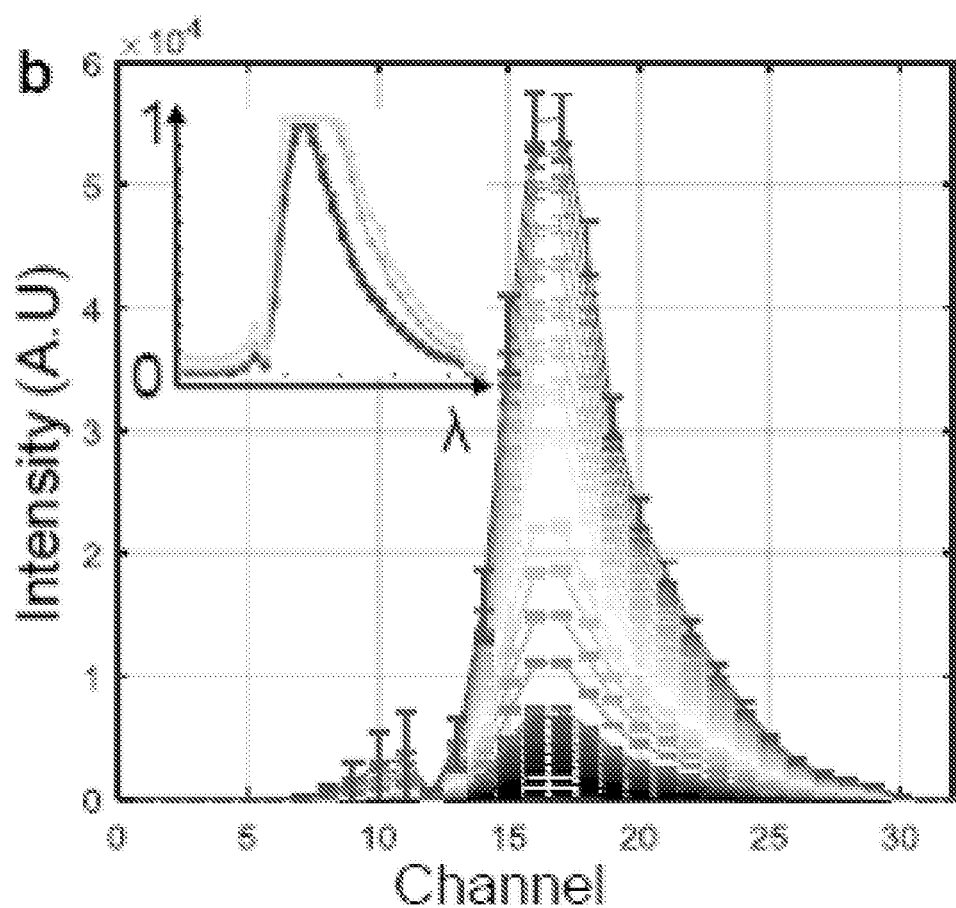
Figure 1C:
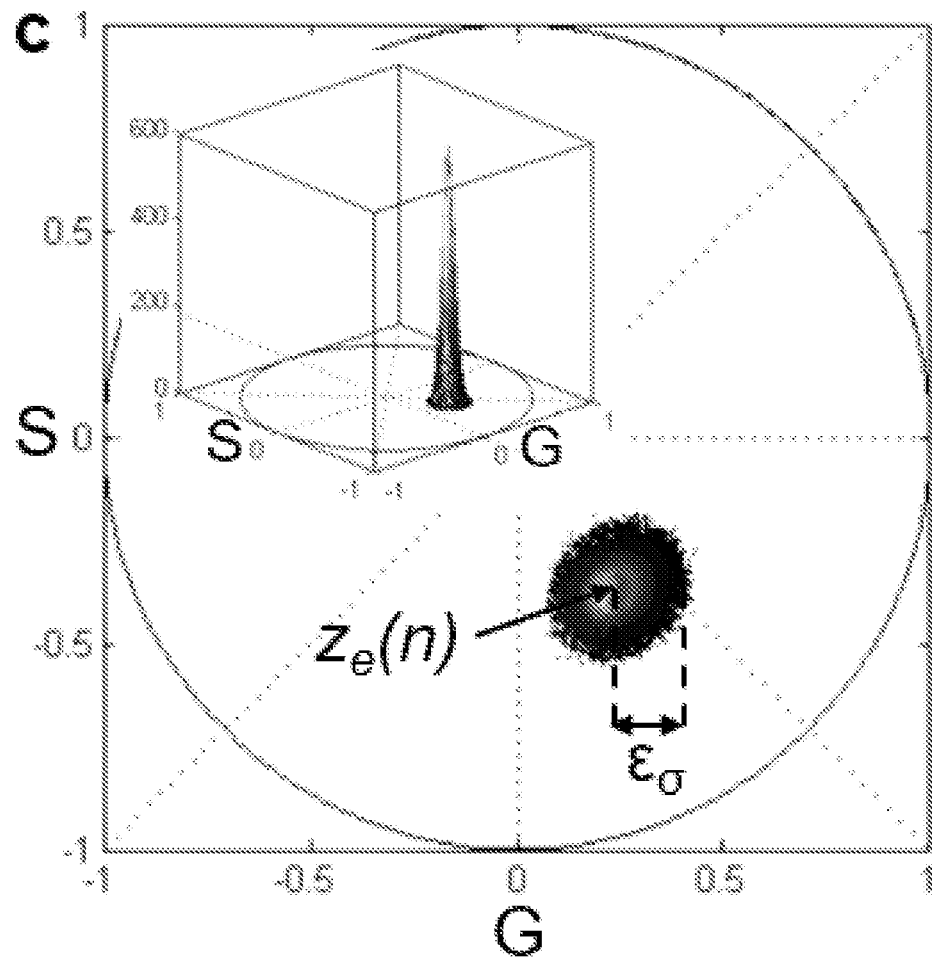
Figure 1D:
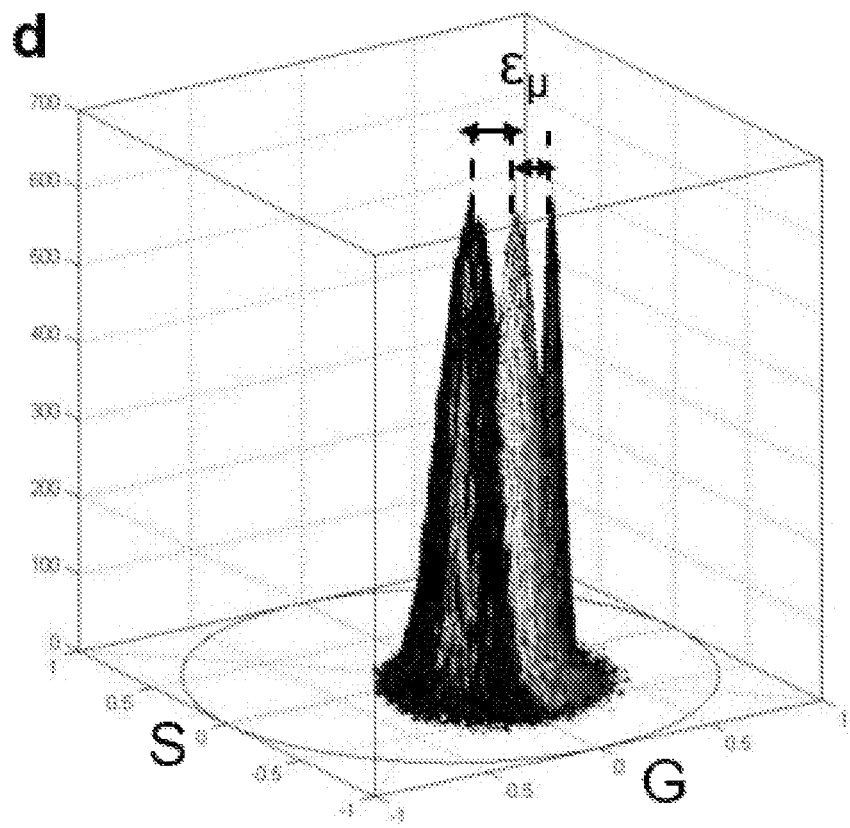

Scatter error may be observed around the expected fingerprint $z_e(n)$ of a spectrum when multiple measurements of the same fluorophore are represented on the phasor plot, and may be viewed as the standard deviation of phasor points around $z_e(n)$ (FIG. 1c). Shifted-mean error may be the result of degraded spectral shape from reduced SNR, inappropriate black-level settings, or inappropriate gain settings (saturation). Depending upon settings of the system, the average fingerprint position on the phasor plot may be shifted from its expected position $z_e(n)$ by the amount of the shifted-mean error (FIG. 1d). Combined, these two errors may disperse the points around the correct position on the phasor-plot $z_e(n)$.

Photon counting in an experiment may help quantify estimation of the bounds on either form of error. The detectors on most microscopes, and commercial multi-spectral confocal systems in particular, may record analog signals rather than photon counts. For the systems comprising such microscopes, quantitative estimates of these errors, in terms of recorded intensity values in the analog mode may be achieved.

To develop an experimental approach for estimating the contributions of both sources of error on the phasor plot, the emission spectra of fluorescein on a commercial confocal microscope equipped with parallel multi-channel spectral detector, at different acquisition parameters (Table 1, shown below) were recorded.

TABLE 1

Parameters for Fluorescein imaging.

| | Gain (A.U.) | 488 nm laser power (%) | Pixel dwell time (µs) |
|---|---|---|---|
| Experiment 1 | 500-1250 in steps of 25 | 2 | 6.3 |
| Experiment 2 | 700 | 1-60 in steps of 3 | 6.3 |
| Experiment 3 | 750 | 1-60 in steps of 3 | 6.3 |
| Experiment 4 | 800 | 1-21 in steps of 3 | 6.3 |
| Experiment 5 | 850 | 1-21 in steps of 3 | 6.3 |
| Experiment 6 | 900 | 1-21 in steps of 3 | 6.3 |
| Experiment 7 | 950 | 1-21 in steps of 3 | 6.3 |
| Experiment 8 | 850 | 21 | 2.55-177.32 in steps dictated by controlling software |

Figure 1E:
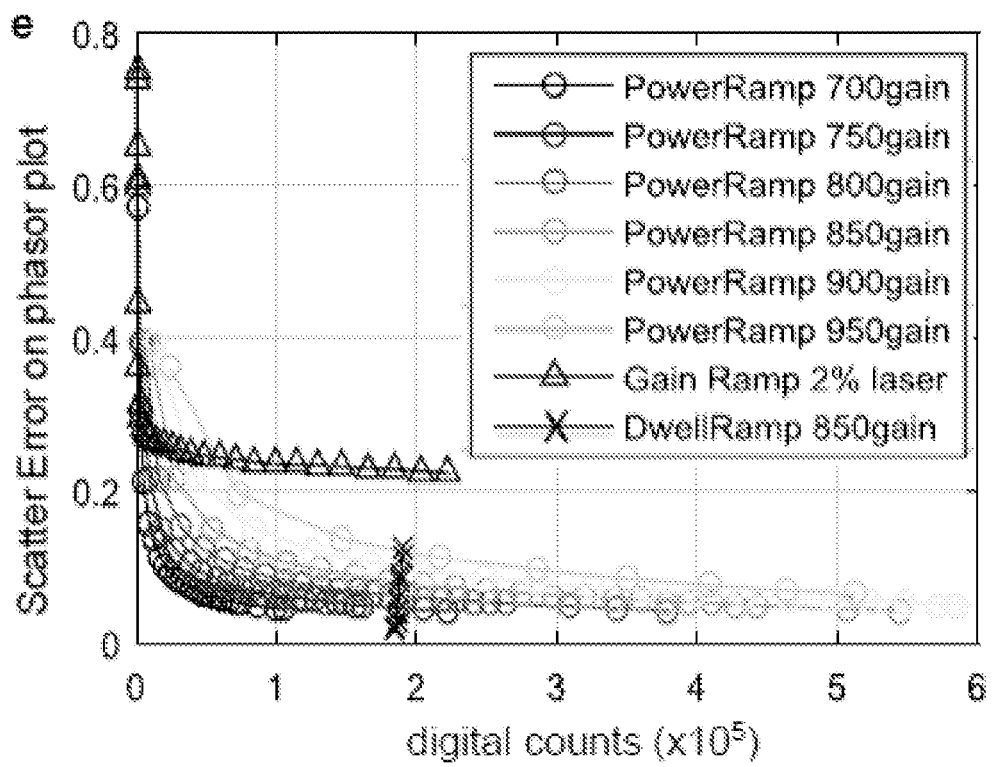

Based on the transform used in this disclosure and by propagation of statistical errors, scatter error, std{z(n)} may be derived. It may scale inversely as the square root of the total digital counts N (Equation 2, below). Experimental data confirm that scatter error scales inversely as $\sqrt{N}$ for different acquisition parameters within the standard range of microscope settings (FIG. 1e, FIG. 4a). Furthermore, the constant of proportionality in Equation 2, depends on the detector gain used in the acquisition (FIG. 5e and Table 2, shown below).

TABLE 2

Proportionality constant for curves to calculate scatter error on phasor plot.

| Gain (A.U.) | Slope | |z(n)| | Proportionality constant |
|---|---|---|---|
| 700 | 1.35 | 0.43 | 3.14 |
| 750 | 1.8 | 0.437 | 4.12 |
| 800 | 2.34 | 0.437 | 5.36 |
| 850 | 3.03 | 0.443 | 6.83 |
| 900 | 3.89 | 0.446 | 8.72 |
| 950 | 4.79 | 0.45 | 10.65 |

Figure 5D:
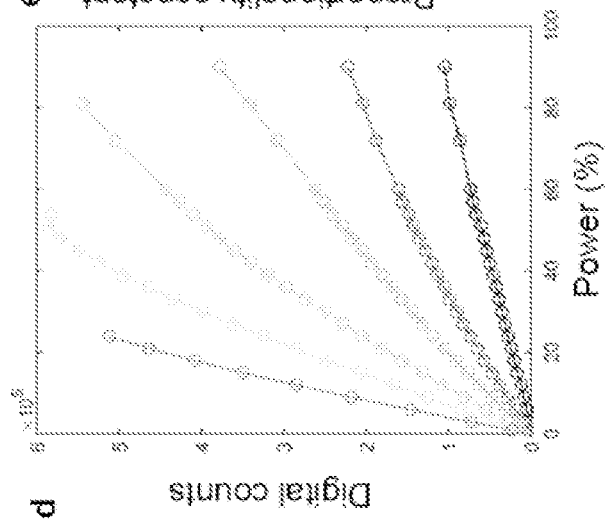
FIG. 5 Sensitivity of phasor point. (a,b,c) $|Z(n)|$ may remain nearly constant for different imaging parameters. Legend applies to (a,b,c,d,e). (d) Total digital counts as a function of laser power. (e) Proportionality constant in Equation 2 may depend on the gain. (f) Relative magnitudes of residuals ($R(n)$) on phasor plots shows that harmonics n=1 and 2 may be sufficient for unique representation of spectral signals.
Figure 5E:
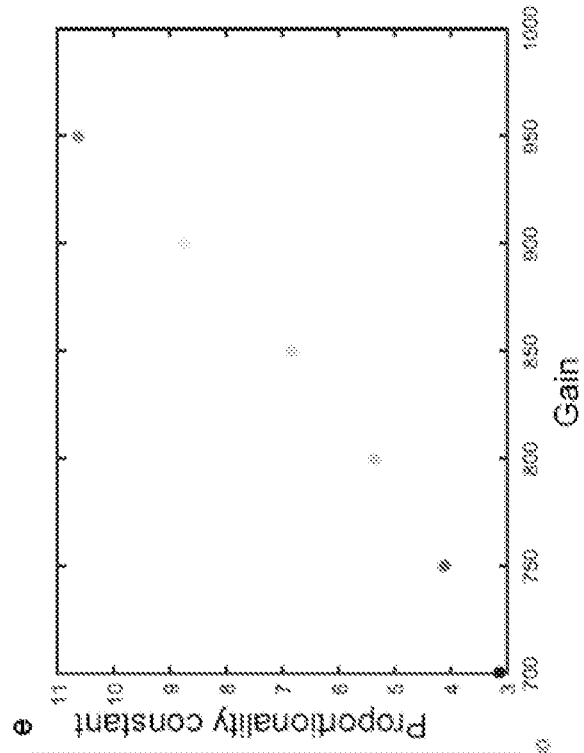

Detector shot noise may be proportional to gain [22], and scatter error empirically shows this characteristic (FIG. 5d-e). Given identical normalized spectra measured with different microscope settings, the one with higher gain value may have higher scatter error. However, the expected position of the spectral fingerprint $|z_e(n)|$ may remain constant over a large range of total digital counts for different imaging parameters (FIG. 5a-c).

Changes in Shifted-Mean of a spectrum. Phasor plot may rely on normalized spectrum of a pixel to determine the coordinates. However, both the saturation of signal and very low photon counts (low signal to noise ratio (SNR)) may result in non-identical normalized spectra (FIG. 1b, inset). This may change the values of |z(n)| at the extreme values of total digital counts (FIG. 4a-c). At low SNR the signal may be indistinguishable from noise. At very high SNR, identical intensity values for several wavelengths, corresponding to saturation value on detector (FIG. 1b, inset), may render the spectrum non-informative again. In either cases, the phasor point may move to be closer to origin leading to low values of |z(n)|. Within the constant regime (FIG. 4a-e), the values of |z(n)| may be most sensitive to changes in the values of detector gain among the three parameters—namely detector gain, power and pixel dwell time (FIG. 4a-c).

The type of detect use for measures may affect the error on phasor. In any imaging system, the number of photons emitted by a dye during a time interval may be a stochastic (Poissonian) process, where the signal may scale as the average number of acquired photons N, and the noise may scale as $\sqrt{N}$. Typically the source of noise may comprise of shot noise resulting from (i) signal light (ii) background light and (iii) dark current.

In experiments, analog detectors were used for all measures. A typical Photomultiplier Tube (PMT) may measure the pulse of electrons at the anode resulting from a photon striking at its photocathode. These pulses may be counted both individually and as an averaged photocurrent in a given interval, thereby allowing both digital (photon-counting) and analog modes of operation respectively. While the noise (Poissonian) from signal and background light may remain the same for both analog and digital counts, shot noise from dark currents may vary in the two modes. The dark current may consist of thermal electrons with a typical pulse height distribution that, in photon-counting, may be discriminated robustly from the signal using a pulse height discriminator and thus eliminated. In analog mode, the averaged pulse may also incorporate the dark current leading to a higher noise. Signal to noise ratio (SNR) in the digital mode may improve compared to analog mode. Additionally, photon-counting mode may better perform at low signal levels, so as to avoid simultaneous arrival of two photons. Analog mode may operate over a wide range of photon levels.

For the purpose of HySP, the Fourier transforms may convert all photons collected across spectrum into one point in the phasor plot. In the photon-counting mode, HySP performance may be expected to be further enhanced due to the improved SNR compared to analog mode at low signal levels.

Figure 1F:
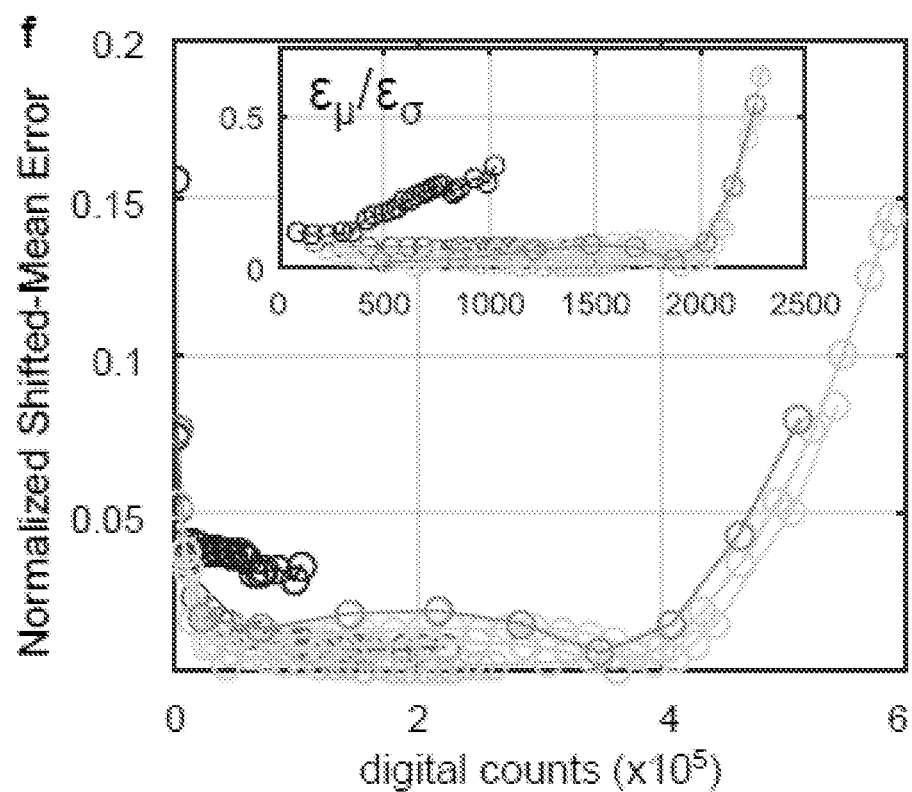

The repeatability of the spectral fingerprint may have two major effects on the shifted-mean error, a measure for the quality of fingerprinting. First, since it may be a function of $|z_e(n)|$, this error may remain below 5% over a large range of digital counts except for extreme counts values (FIG. 10. Similar to scatter error, within reasonable range, it may only slightly sensitive to changes in detector gain. Second, comparison of the magnitudes of the two errors may show that scatter error may be dominant in phasor analysis (FIG. 1f, inset). Thus, any shift in the phasor point due to suboptimal imaging parameters may be likely to be buried within the scatter.

Because scatter error may dominate the error on HySP plot, and the phasor plot may reduce spectral dimensionality from 32 to 2, it may be possible to denoise the spectral images without altering the intensity data by directly applying filters in phasor space to reduce scatter error. Here, a denoising filter in phasor space was applied to reduce scatter error in the data, and significant recovery of fingerprint position $|z_e(n)|$ was observed, especially at low signal values. The plots show that denoising may not alter the location of the expected values ($z_e(n)$) (FIG. 4b-d), yet scatter error may be reduced (FIG. 4c). Repeated applications of a denoising filter may lead to a plateau of improvement that may typically occur after five iterations. Since the filter may be applied in phasor space, it may not affect the intensity profile of the image (FIGS. 9 and 10).

Figure 8A:
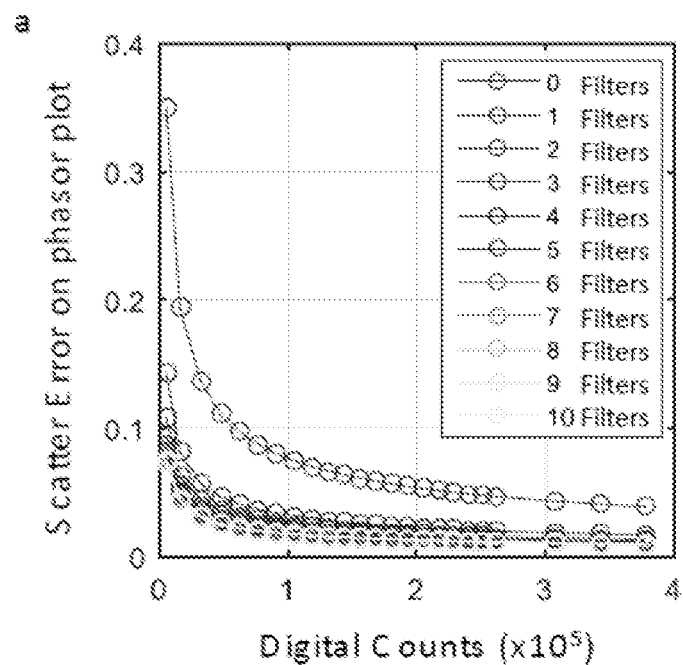
FIG. 8 Effect of phasor space denoising on Scatter Error and Shifted-Mean Error. (a) Scatter Error as a function of digital counts for different number of denoising filters with 3 by 3 mask. Data origin is fluorescein dataset acquired at gain of about 800. (b) Scatter Error as a function of number of denoising filters with 3 by 3 mask for different laser powers. (c) Shifted-Mean Error as a function of digital counts for different number of denoising filters with 3 by 3 mask. Data origin is fluorescein dataset acquired at gain of about 800. (d) Shifted-Mean Error as a function of number of filters with 3 by 3 mask for different laser powers. (e) Relative change of Scatter Error as a function of number of denoising filters applied for different mask sizes. (f) Relative change of Shifted-Mean Error as a function of number of filters applied for different mask sizes. "Filters" of this figure are denoising filters.
Figure 8B:
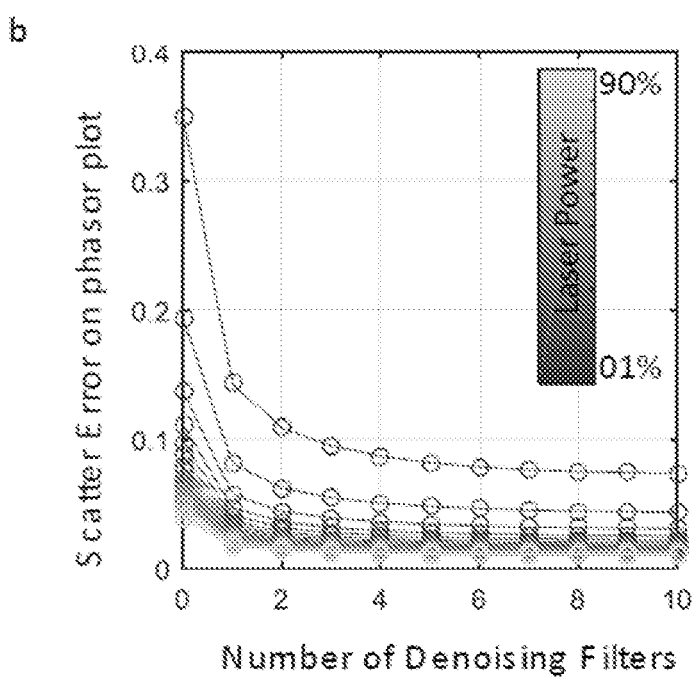
Figure 8C:
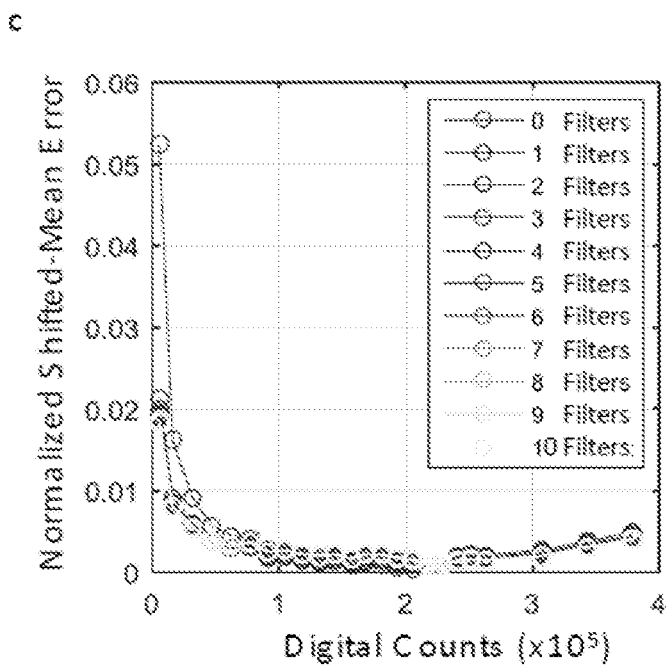
Figure 8D:
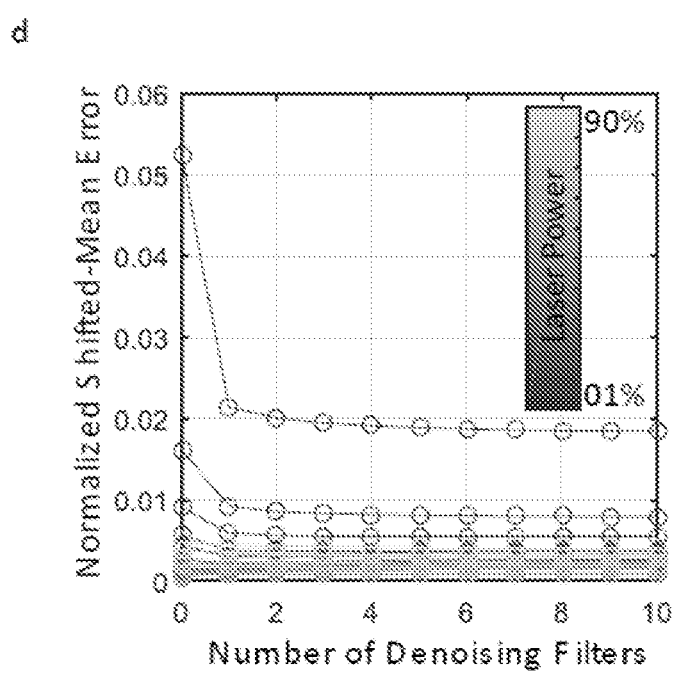
Figure 8E:
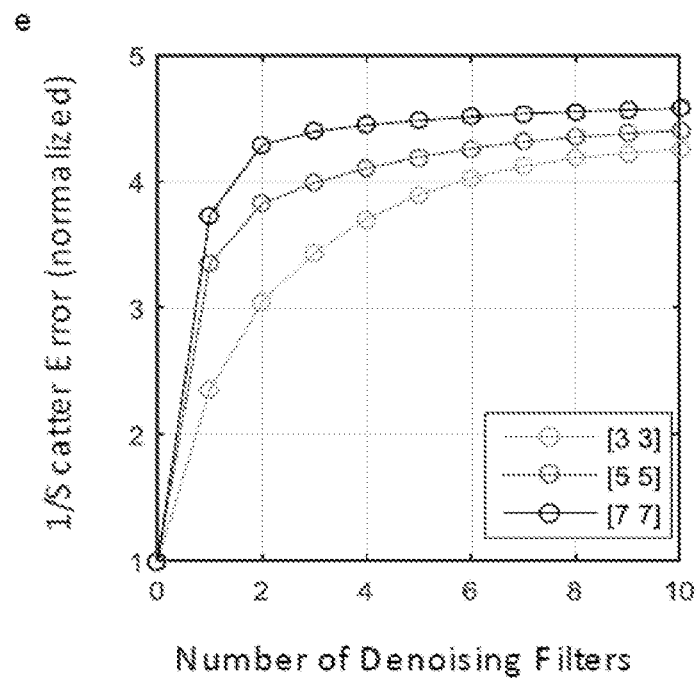
Figure 8F:
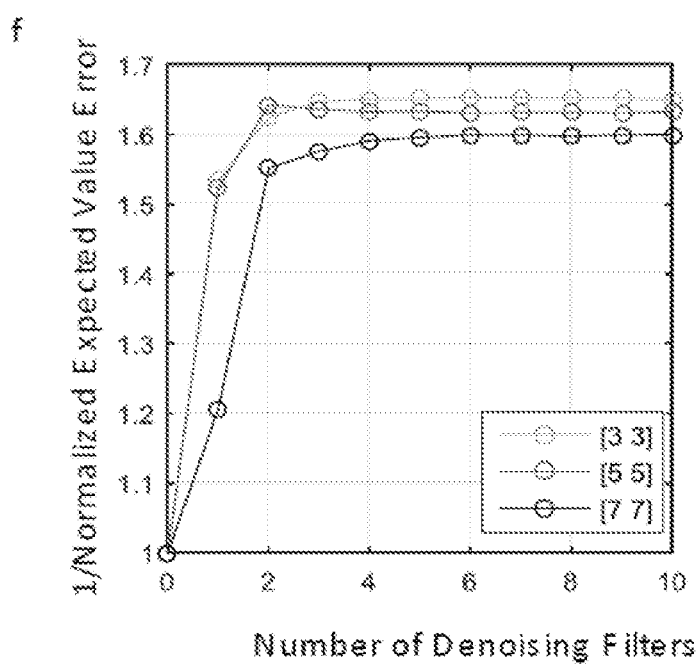
Figure 9A:
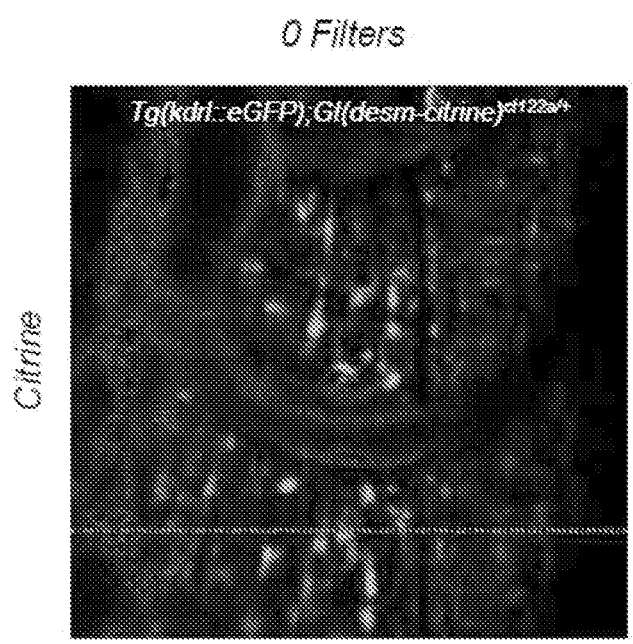
FIG. 9 Effect of phasor space denoising on image intensity. (a,b) HySP processed Citrine channel of a dual labeled eGFP-Citrine sample (132.71 um×132.71 um) before and after filtering in phasor space. (c,d) HySP processed eGFP channel of the sample in (a,b) before and after filtering in phasor space. (e) Total intensity profile of the green line highlighted in (a,b,c,d) for different number of denoising filters. Intensity values may not be changing. (f) eGFP channel intensity profile of green line highlighted in (a,b,c,d) for different number of denoising filters. (g) Citrine channel intensity profile of green line highlighted in (a,b,c,d) for different number of denoising filters. "Filters" of this figure are denoising filters.
Figure 9B:
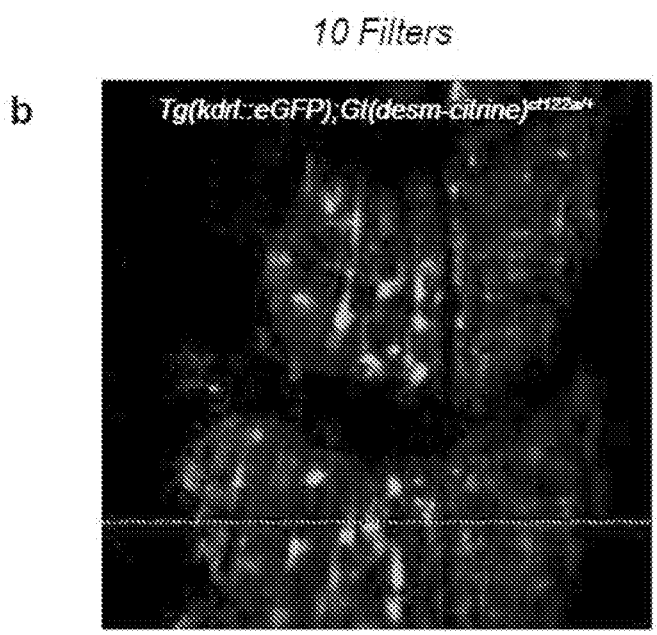
Figure 9C:
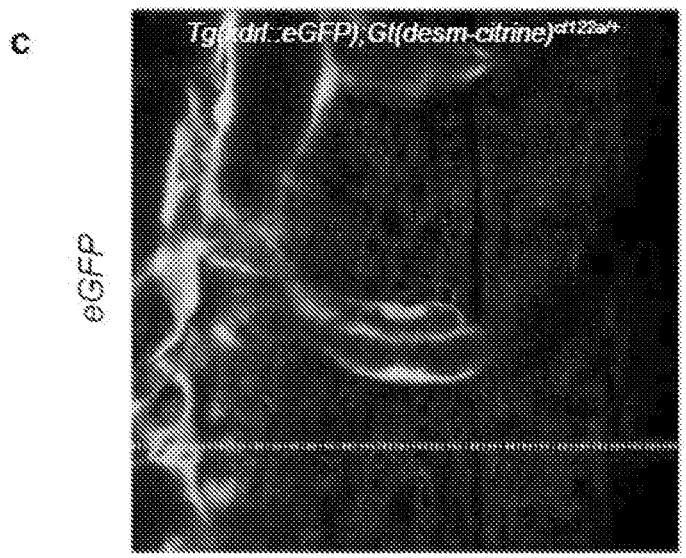
Figure 9D:
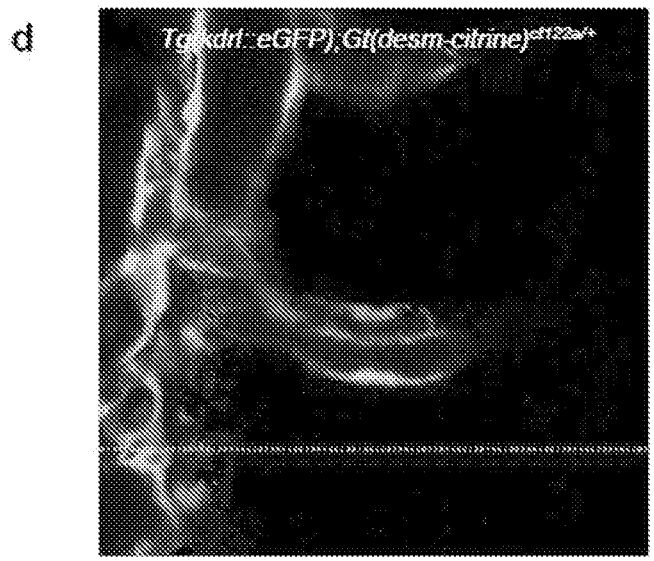
Figure 9E:
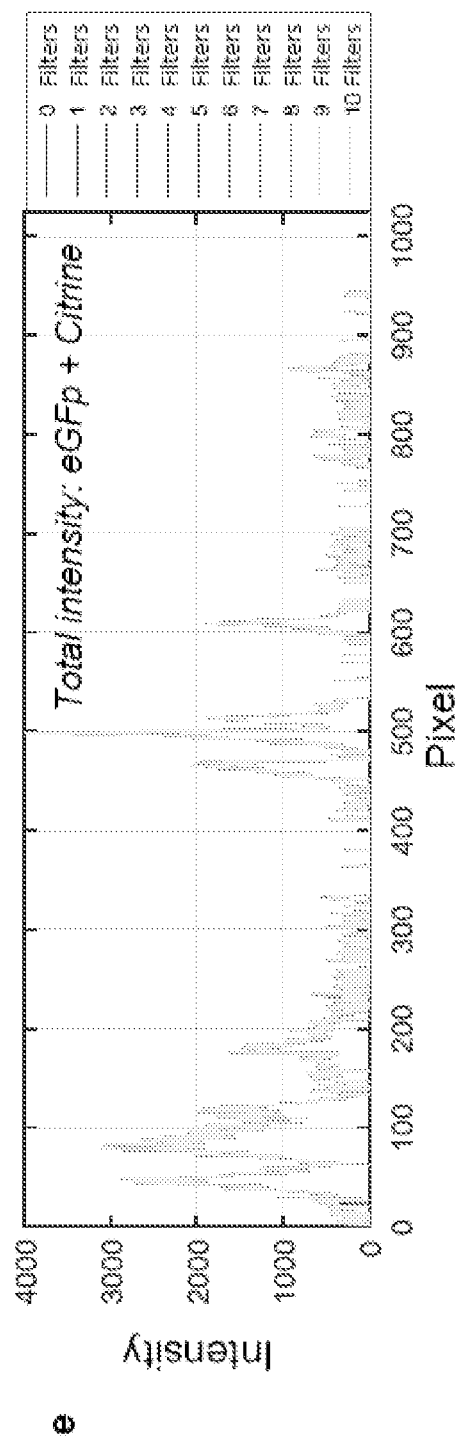
Figure 9F:
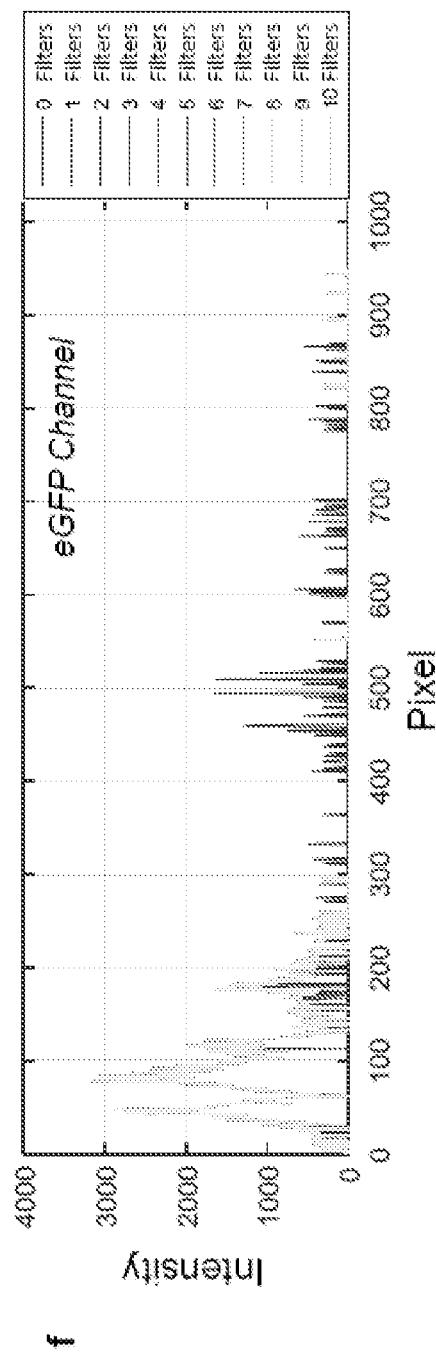
Figure 9G:
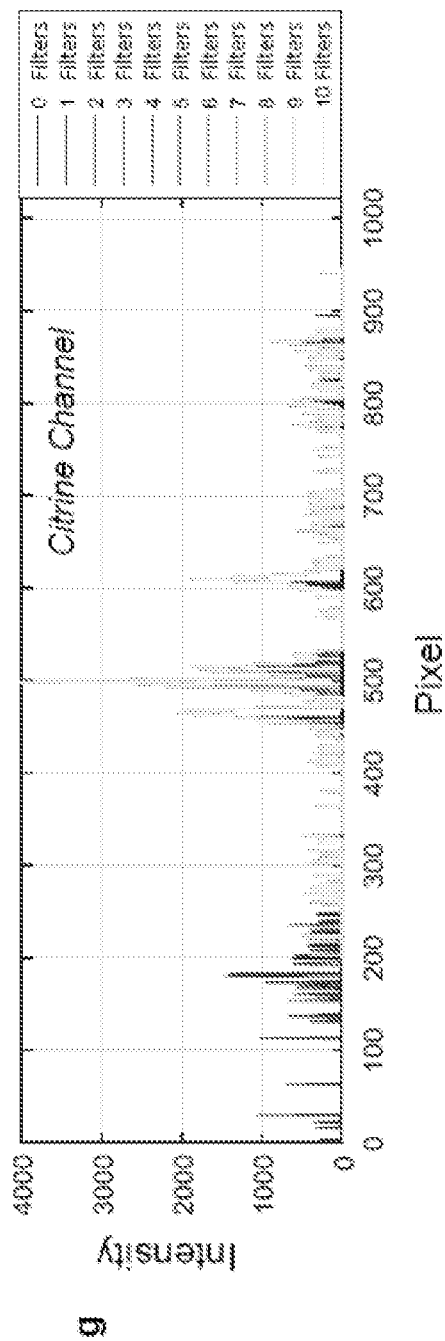

Spectral denoising in phasor space. Spectral denoising may be performed by applying filters directly in phasor space. This may maintain the original image resolution but may improve spectral fingerprinting in the phasor plot. The filter here applied may be a median filter. However, other approaches may also be possible. For any image of a given size (n×m pixels), S and G values may be obtained for every pixel, yielding 2 new 2D matrices, for S and G, with dimensions n×m. Since the initial S and G matrix entries may have the same indices as the pixels in the image, the filtered matrices S* and G*, therefore, may preserve the geometrical information. Effectively by using filtering in phasor space, S and G matrices may be treated as 2D images. First, this may reduce the scatter error, i.e. the localization precision on phasor plot increases (FIG. 8a-b), improving the spectral fingerprinting resolution while improving the already minimal Shifted-Mean Error (FIG. 8c-d). The effect on data may be an improved separation of distinct fluorescent proteins (FIG. 9a-d). Second, denoising in (G,S) coordinates may preserve both geometry, intensity profile as well as the original resolution at which the images were acquired (FIG. 9e-g). Effectively filtering in phasor space may affect the spectral dimension of the data achieving denoising of spectral noise without interfering with intensities.

Improved signal collection (FIG. 11) and reduced uncertainty may appear to make HySP an appealing technique for in vivo imaging. Studies of cellular and tissue interactions may often involve use of multiple fluorescent markers within the same anatomical region of developing embryos or other biological samples. Furthermore, dataset sizes for multi-(hyper) spectral fluorescence may be up to n times larger than standard confocal, with n equal to the number of bandwidths acquired (e.g. 32).

Four-dimensional (x,y,z,λ) data were acquired for whole-mount zebrafish embryos and represented spectral information from all pixels in a HySP plot to identify fluorophore fingerprints (Table 3), ranging from tissue to subcellular scale.

TABLE 3

Parameters for in vivo imaging. All data points are 16 bits integers.

| | Stage (hpf) | Imaged volume (xyzλt) (pixels) | Lateral pixel (x, y resolution) (μm) | Axial section (z resolution) (μm) | Pixel dwell time (μs) | Pinhole size (μm) | Laser Power (%) |
|---|---|---|---|---|---|---|---|
| FIGS. 1a; 6b, d; 7b; 10b (Tg(kdrl::eGFP); Gt(desm-citrine)$^{ct122a/+}$) | 72 | 3584 × 768 × 45 × 32 | 0.92 | 5.0 | 5.09 | 180 | 0.3 @488 nm |
| FIGS. 6d; 7b; 10b (Gt(desm-citrine)$^{ct122a/+}$) | 72 | 1408 × 384 × 39 × 32 | 1.84 | 5.0 | 5.09 | 180 | 0.5 @488 nm |
| FIGS. 6d; 7b; 10b (Tg(kdrl::eGFP)) | 72 | 1408 × 384 × 40 × 32 | 1.84 | 5.0 | 5.09 | 180 | 0.9 @488 nm |
| FIG. 6e, f | 72 | 600 × 60 × 45 × 32 | 0.95 | 5.0 | 5.09 | 180 | 0.3 @488 nm |
| FIGS. 2c; 12 | 74 | 2560 × 2048 × 29 × 32 | 0.277 | 5.0 | 3.15 | 186 | 3.0 @458 nm |
| FIGS. 2c; 12 | 74 | 2560 × 2048 × 29 × 32 | 0.277 | 5.0 | 3.15 | 186 | 0.3 @561 nm |

TABLE 3-continued

Parameters for in vivo imaging. All data points are 16 bits integers.

Figure 2A:
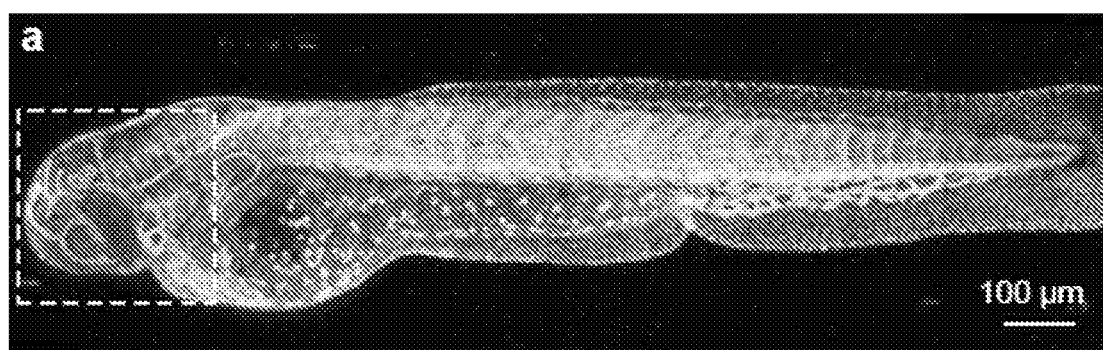
FIG. 2 Phasor analysis for multiplexing hyper-spectral fluorescent signals in vivo. (a) Maximum intensity projection image showing seven unmixed signals in vivo in a 72 hpf zebrafish embryo. Multiplexed staining was obtained by injecting mRNA encoding H2B-cerulean (cyan) and membrane-mCherry (red) in double transgenic embryos Gt(desm-citrine)$^{ct122a/+}$; Tg(kdrl:eGFP) (yellow and green respectively) with Xanthophores (blue). The sample was excited sequentially at about 458 nm and about 561 nm yielding their autofluorescence as two separate signals (magenta and grey respectively). Images were reconstructed by mapping the scatter densities from phasor plots (d) to the original volume in the 32-channel raw data. (b) Emission spectra of different fluorophores obtained by plotting normalized signal intensities from their respective regions of expression in the raw data. (c) Zoomed-in view of the head region of the embryo (box in (a)). Boxes labeled 1-3 denote sub-regions of this image used for comparing HySP with linear unmixing in (e-f). (d) Phasor plots showing the relative positions of pixels assigned to different fluorophores. Polygons denote the sub-set of pixels assigned to a particular fluorophore. (e) Zoomed-in views of Regions 1-3 (from (c)) reconstructed via both HySP analysis and linear unmixing of the same 32-channel signal. Arrows indicate the line along which normalized intensities obtained by the two techniques are plotted in (f) for comparison. By visual inspection itself it is evident that HySP analysis outperforms linear unmixing in distinguishing highly multiplexed signals in vivo. (f) Normalized intensity plots comparison of HySP analysis and linear unmixing. The x-axes denote the normalized distance along the arrows drawn in (e). y-axes in all graphs were normalized to the value of maximum signal intensity among the seven channels to allow relative comparison. Different panels show different set of channels (fluorophores) for clarity.
Figure 2B:
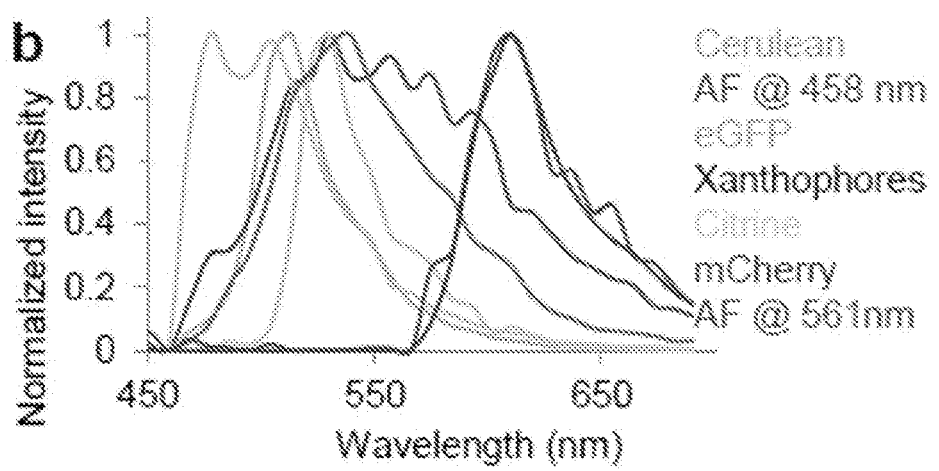
Figure 2C:
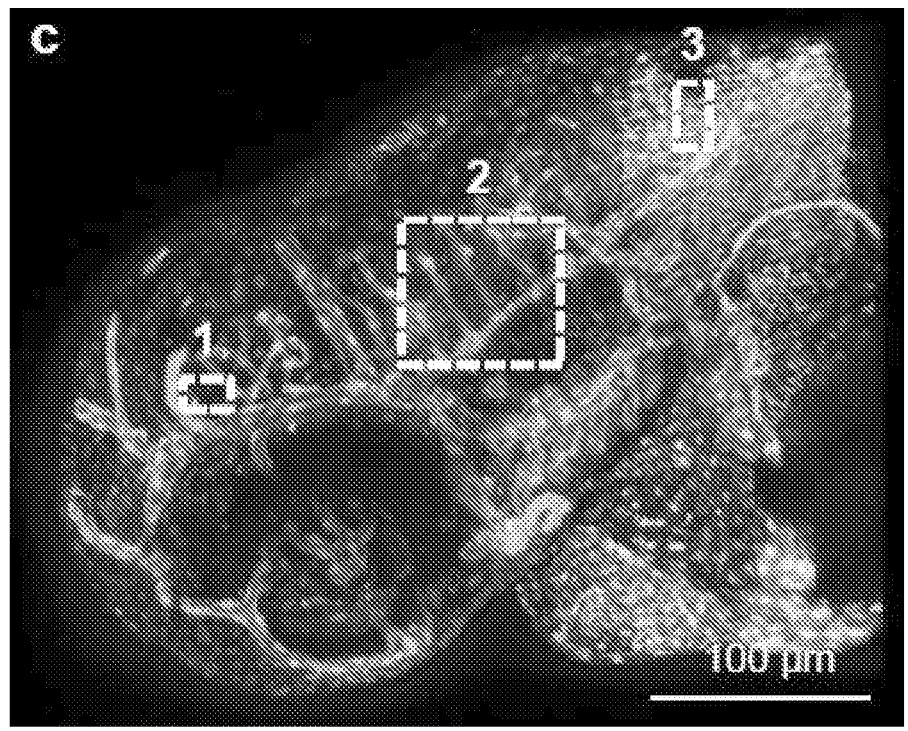
Figure 2D:
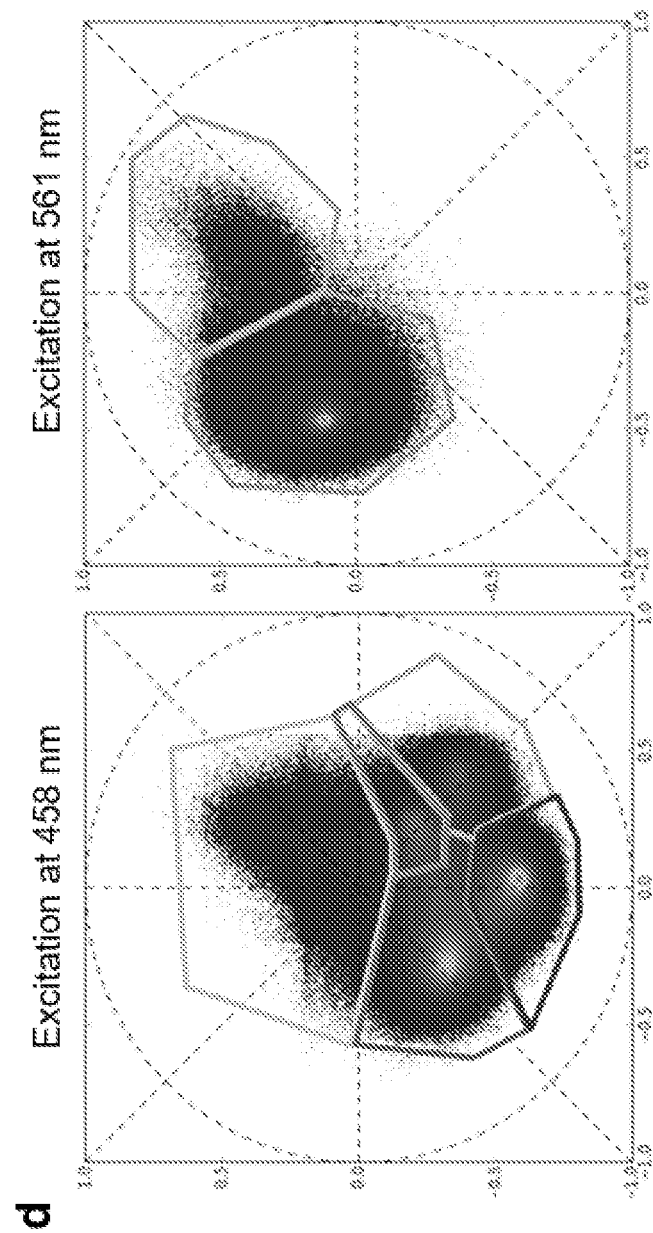
Figure 2E:
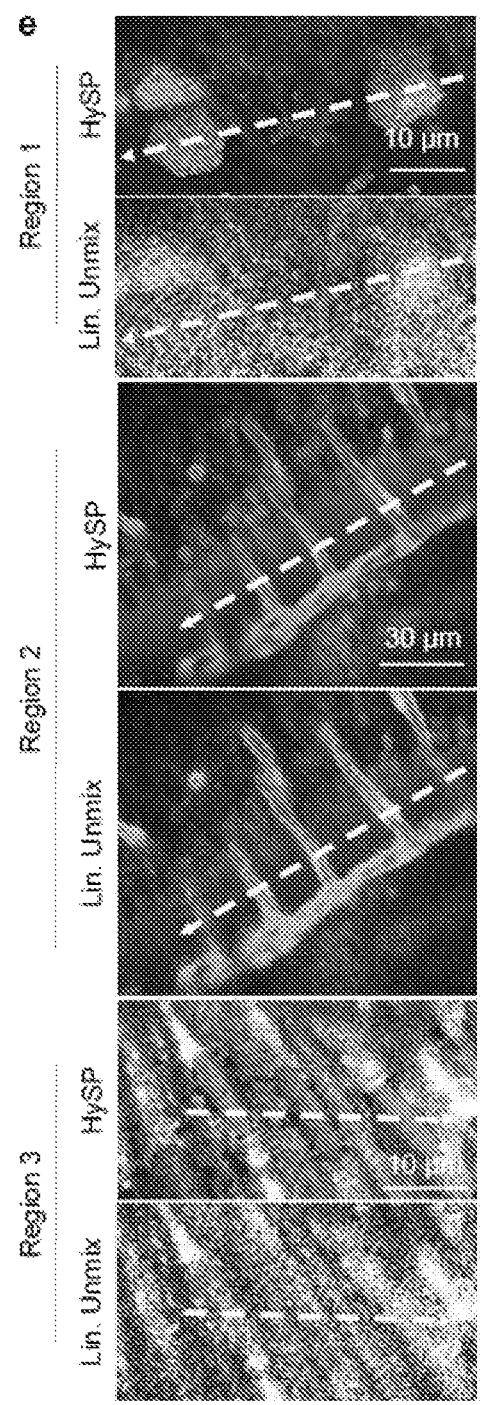
Figure 2F:
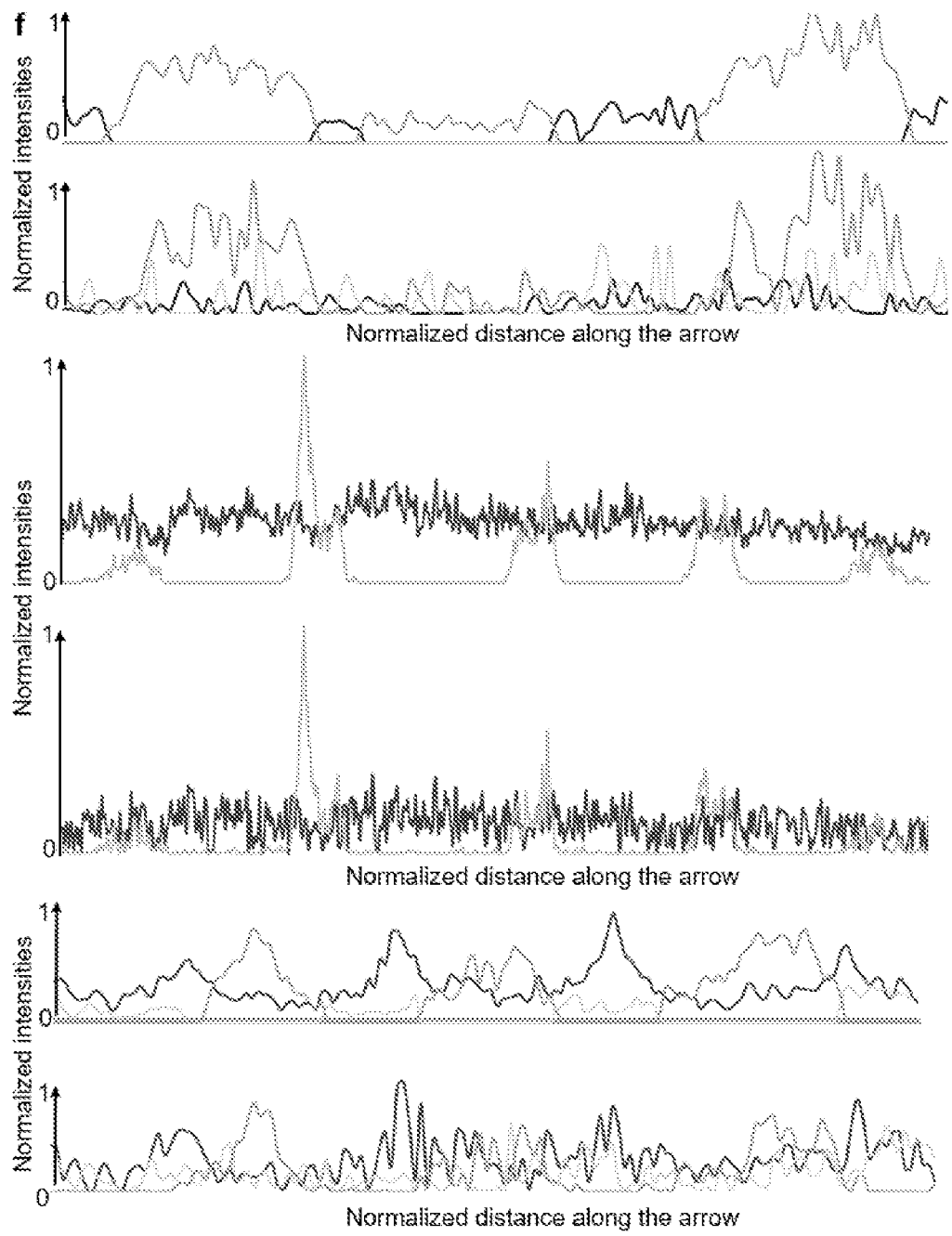
Figures 3A, 3B, 3C, 3D, 3E:
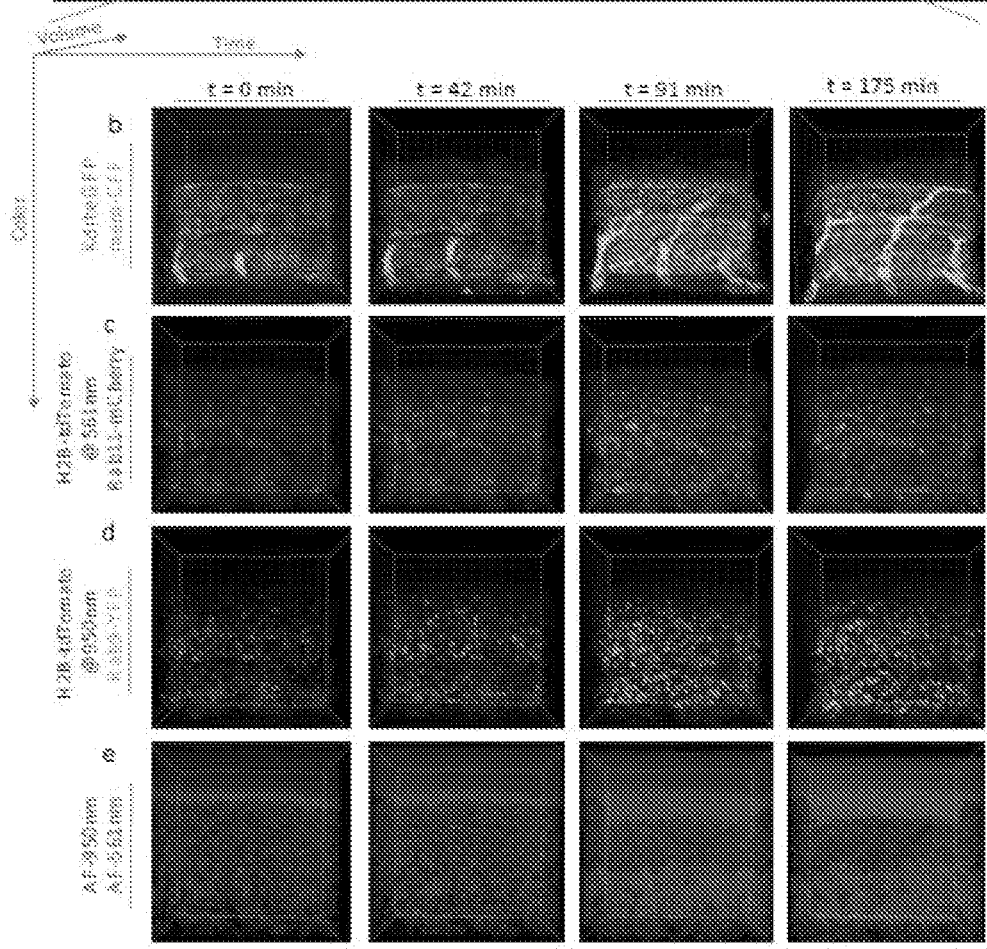
FIG. 3 Low laser power in vivo volumetric hyper-spectral time-lapse of zebrafish. (a) Brightfield image of zebrafish embryo about 12 hours post imaging (36 hpf). HySP improved performance at lower Signal to Noise Ratio allows for multi-color volumetric time-lapses with reduced phototoxicity. (b-e) Maximum intensity projection image showing eight unmixed signals in vivo in a zebrafish embryo starting at 24 hpf. Multiplexed staining was obtained by injecting mRNA encoding Rab9-YFP (yellow) and Rab11-RFP(red) in double transgenic embryos, Tg(ubiq: membrane-Cerulean-2a-H2B-mCherry); Tg(kdrkeGFP) (red, cyan and green respectively). The sample was excited sequentially at about 950 nm (b and d) and about 561 nm (c) yielding their autofluorescence as two separate signals (e) (purple and orange respectively). Time-lapse of 25 time-points at about seven minute intervals were acquired with laser power at about 5% at about 950 nm and about 0.2% at about 561 nm.

| | Stage (hpf) | Imaged volume (xyzλt) (pixels) | Lateral pixel (x, y resolution) (μm) | Axial section (z resolution) (μm) | Pixel dwell time (μs) | Pinhole size (μm) | Laser Power (%) |
|---|---|---|---|---|---|---|---|
| FIG. 9a-d | 72 | 1024 × 1024 × 1 × 32 | 0.13 | 1.4 | 3.15 | 70 | 1.0 @488 nm |
| FIGS. 2A, 13 | 72 | 1664 × 512 × 55 × 32 | 2.076 | 5.0 | 6.50 | 186 | 3.0-5.0 @458 nm |
| FIGS. 2A, 13 | 72 | 1664 × 512 × 55 × 32 | 2.076 | 5.0 | 6.50 | 186 | 0.18 @561 nm |
| FIG. 3b, c, d, e | 24 | 512 × 512 × (25-40) × 32 × 25 | 0.277 | 2.0 | 2.55 | 601 | 5 @950 nm |
| FIG. 3b, c, d, e | 24 | 512 × 512 × (25-40) × 32 × 25 | 0.277 | 2.0 | 2.55 | 601 | 0.2 @561 nm |

Figure 7A:
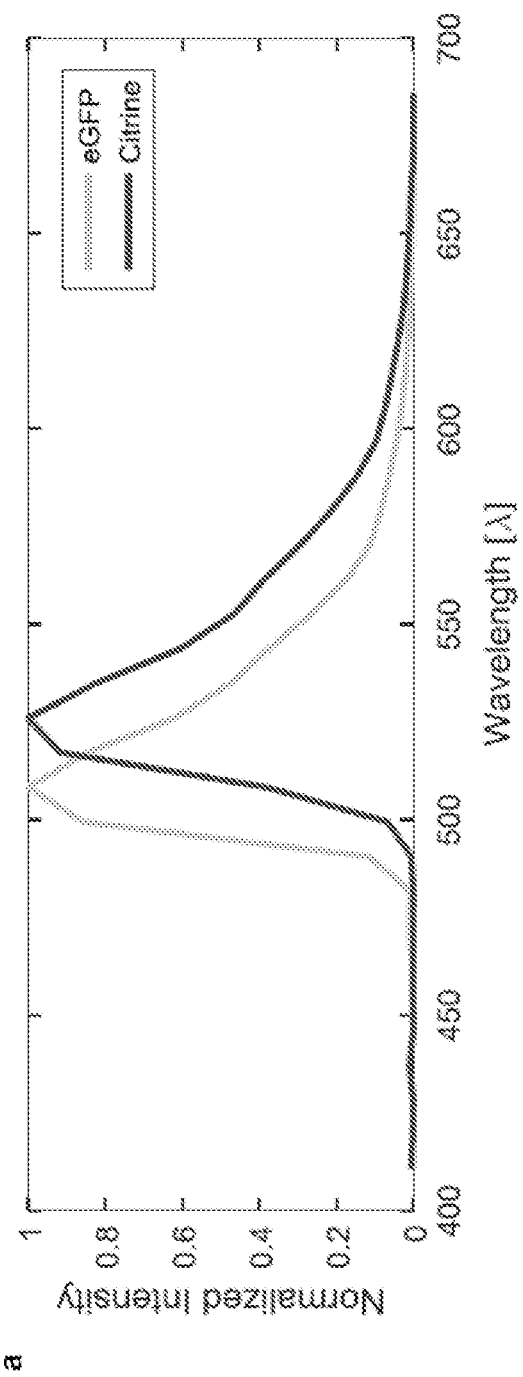
FIG. 7 Optical separation of eGFP and Citrine. (a) Spectra of citrine (peak emission about 529 nm, skeletal muscles) and eGFP (peak emission about 509 nm, endothelial tissue) measured using confocal multispectral lambda mode in transgenic zebrafish lines Gt(desm-citrine)$^{ct122a/+}$ and Tg(kdrl:eGFP) respectively. (b) Conventional optical separation (using emission bands on detector) of spectrally close fluorophores (eGFP and citrine) may not overcome the problem of bleed-through of signal in respective channels. Arrows indicate erroneous detection of eGFP or citrine expressions in the other channel. Scale bar about 300 µm. (c) Normalized intensity profiles along the length (600 pixels, about 553.8 µm) of the line in panel (a).
Figure 7B:
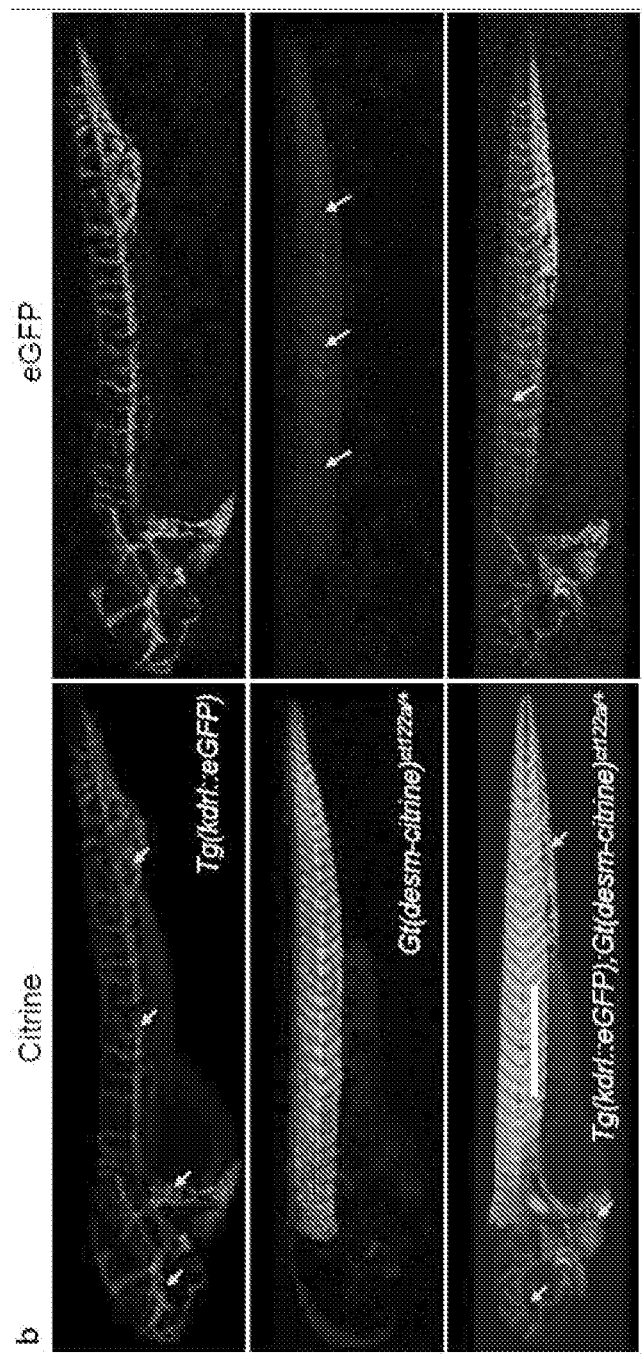
Figure 7C:
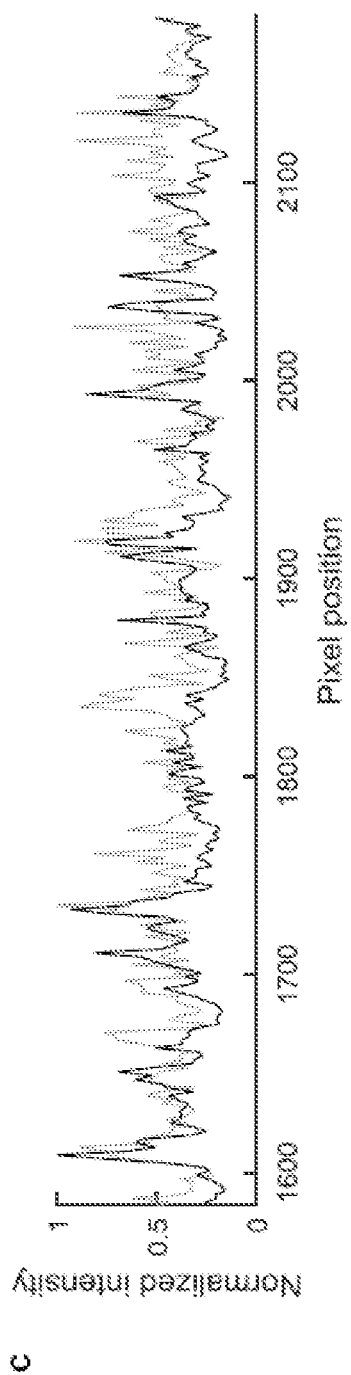

Points selected in phasor space were re-mapped in the original volume and rendered as Maximum Intensity Projections. This successfully captured the unique spectral fingerprints of citrine (skeletal muscles) and eGFP (endothelial tissue) in transgenic zebrafish embryos, Gt(desm-citrine)$^{ct122a/+}$ and Tg(kdrl:eGFP) respectively [23,24] (FIG. 6a, 7a). On a tissue scale, the method may preserve the individual spectral fingerprints (scatter densities) for citrine and eGFP even in the double transgenic Gt(desm-citrine)$^{ct122a/+}$; Tg(kdrkeGFP) embryos, which may feature co-expression within the same anatomical regions (FIG. 6d). The two easily separable scatter densities in phasor space (FIG. 6c) may cleanly distinguish the label in the skeletal muscles from that in the interdigitated blood vessels (endothelial tissue). Additionally, autofluorescence may clearly be separated by treating it as an independent HySP fingerprint (FIG. 10).

Autofluorescence in phasor space for in vivo imaging. Hyperspectral phasor may allow intuitive identification of fingerprints for fluorescent proteins. This may be shown for Citrine and eGFP but may be valid also for autofluorescence. Intracellular intrinsic fluorescence may be a known and common issue in in vivo biological imaging. Its spectral signature may be different from that of Citrine and eGFP. When represented on phasor plot as a scatter density, autofluorescence may have different (S,G) coordinates compared to fluorescent proteins and may create cluster regions in different area of the plot (FIG. 10a).

Figures 10A, 10B:
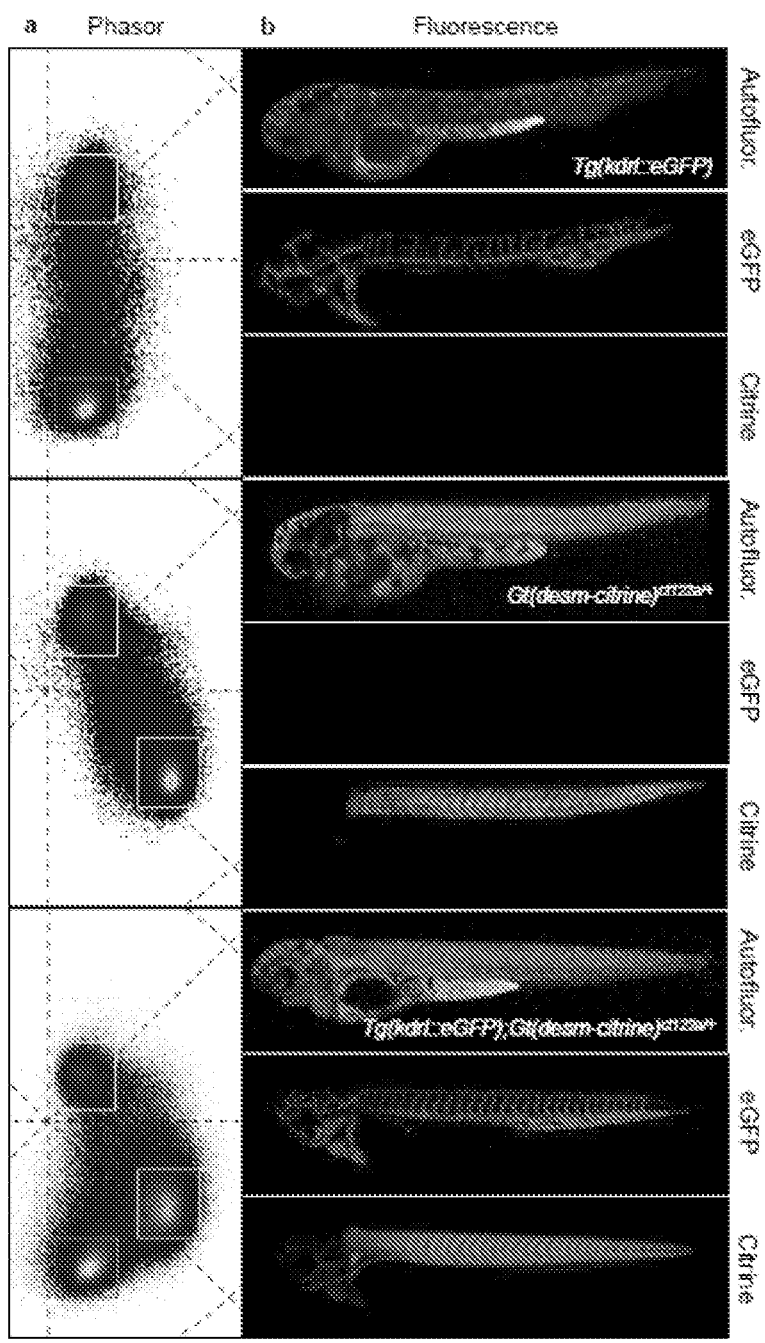
FIG. 10 Autofluorescence identification and removal in phasor space. (a) Phasor plots showing spectral fingerprints (scatter densities) for citrine, eGFP and autofluorescence may allow simple identification of intrinsic signal. (b) Maximum intensity projection images reconstructed by mapping the scatter densities from phasor plot to the original volume. Autofluorescence may have a broad fingerprint that can effectively be treated as a channel. Embryos imaged about 72 hours post fertilization.

Effectively, phasor plot may identify autofluorescence as a separate spectral fingerprint allowing it to be treated as an independent imaging channel (FIG. 10b).

The gap from tissue to sub-cellular scale may be bridged by expanding the color palette with nuclear H2B-cerulean and membrane localized mCherry in the same double transgenic embryo. HySP analysis may allow fast identification and separation of signal from Cerulean, eGFP and Citrine from the intrinsic signals of xanthophores and tissue autofluorescence at about 458 nm excitation. Similarly, it may separate mCherry from background autofluorescence at about 561 nm excitation (FIG. 2).

Finally, the multi-dimensionality may be expanded to include time obtaining five-dimensional (5D) datasets (x,y, z,t,λ) and the challenges of photo-damaging and bleaching in time-lapse imaging may be tackled by fully exploiting the advantages of HySP improved signal collection. New vessel sprouts in double transgenic zebrafish embryos (Tg(ubiq: membrane-Cerulea-2a-H2B-tdTomato); Tg(kdrkeGFP) expressing fusion proteins of the endosome components, Rab9 and Rab11 (YFP and mCherry respectively), and autofluorescence for each laser line (FIG. 3) may be imaged. The low laser power used (about 5% at about 950 nm, about 0.15% at about 561 nm) may not affect development over multiple samples (n=3), while allowing the simultaneous study of at least seven clearly distinctive components without affecting light-sensitive development. Increasing laser power to improve fluorescence signal caused increased photo-toxicity that blocked vessel sprouting.

Multispectral volumetric time-lapse in vivo imaging with phasor. Hyperspectral phasor may allow reduced photo-damage when performing multispectral volumetric time-lapses in vivo. The improved unmixing efficiency at decreased Signal to Noise Ratio (FIG. 11) may play a role in tackling issues related to excess photons.

Generally, when multiple fluorophores are present in the sample, each fluorophore may have an optimal excitation wavelength. It may however be complicated to use multiple wavelengths which are too close (e.g. about 458 nm-about 488 nm-about 514 nm for CFP, GFP, YFP respectively) for excitation without considerably affecting the emission spectra. One solution may be to sequentially excite a volume with each wavelength. Sequential excitation, while optimal to prevent overlapping of emission spectral, may require an extended scanning time and may result in increased photo-damage and bleaching. Additionally, extended scanning time may result in motion artifacts due to sample development. An alternative option may be to excite with a single wavelength multiple fluorophores. The disadvantage in this approach may be the excitation efficiency of the lowest wavelength fluorophore will be higher than the other fluorophores in the sample. For example, at about 458 nm the excitation efficiency of CFP is about 93%, while GFP is about 62% and YFP is about 10%. There is a series of factors that affect the actual number of photons emitted by each fluorophores, such as Quantum Yield, Brightness, pH and concentration. However, in general, we may observe a stronger signal from one fluorescent protein and a weak signal from another. One may want to increase laser power in an attempt to extract more photons from the weaker signal. The effects of increasing laser power above 10% for about 950 nm (n=2) or above 10% for about 458 nm (n=3), in experiments, resulted in halted development of vasculature due to photo-toxicity. The opposite solution may be to deal with lower noisier signals, allowing for correct development of the sample.

The Hyperspectral Phasor method may allow for improved performance at lower SNR, hence overcoming the issue of the weaker signals. This advantage may consequently carry over to 2-photon imaging where excitation efficiency is lower than 1-photon and changing laser wavelength may require a few seconds.

As a consequence, the number of volumes necessary to be acquired may be reduced from 3 to 1 in the 3-fluorophore example described above.

The same approach may be applied on different color-clusters of proteins, for example one "blue" cluster CFP-GFP-YFP (excited at about 458 nm), a second "red" cluster mCherry-tdTomato-RFP (excited at about 561 nm), a third cluster with the multiple iRFPs (excited at about 630 nm).

We show two-photon multicolor volumetric time-lapse imaging of multiple samples as an example of potential application with two color-clusters.

As a result of these 5D measurements, different behaviors of Rab9 and Rab11 in relationship to endothelial cells (kdrl positive) and muscle tissue were observed. In particular, Rab11 positive vesicles were detected at the leading of kdrl positive cells, while this behavior was not observed with rab9 proteins. This example showed how HySP may enable increasingly complex multi-color experiments to interrogate molecular network interactions in vivo.

Figures 11A, 11B:
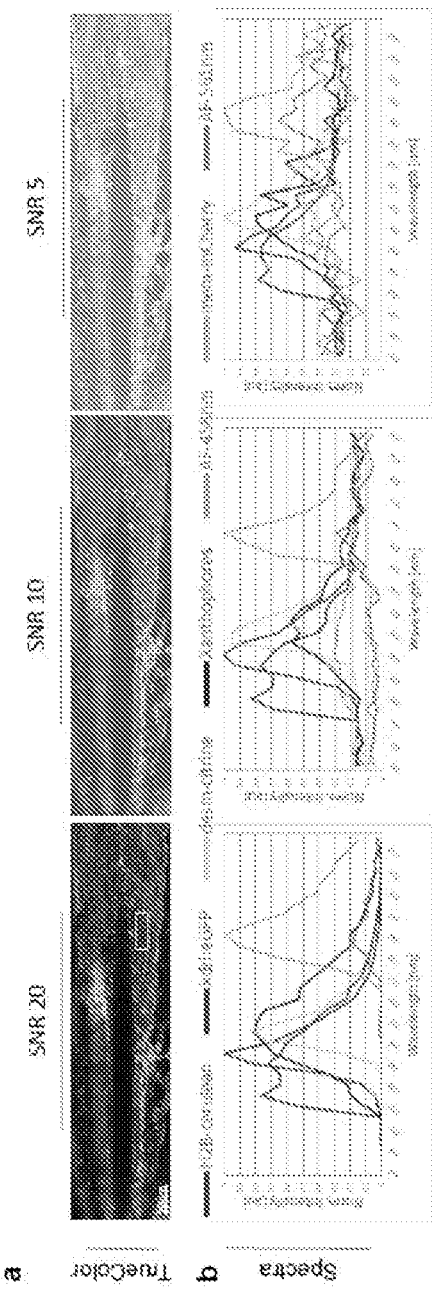
FIG. 11 Comparison of HySP and Linear unmixing under different Signal to Noise Ratio (SNR). (a) TrueColor images of 32 channel datasets of zebrafish labeled with H2B-cerulean, kdrl:eGFP, desm-citrine, Xanthophores, membrane-mCherry as well as Autofluorescence at about 458 nm and about 561 nm. The original dataset (SNR 20) was digitally degraded by adding noise and decreasing signal down to SNR 5. (b) Normalized spectra used for non-weighted linear unmixing. Spectra were identified on each sample from anatomical regions known to contain only the specific label. For example Xanthophore's spectrum was collected in dorsal area, nuclei's from fin, vasculature's intramuscularly. The chosen regions combinations were tested and corrected until optimal linear unmixing results were obtained. The same regions were then used for all three datasets. The same legend and color coding is used through the entire figure. (c) Processed zoomed-in region (box in (a)) for linear unmixing and HySP. The comparison shows three nuclei belonging to muscle fiber. At good SNR (20 and above) both linear unmixing and HySP results are accurate.
Figure 12A:
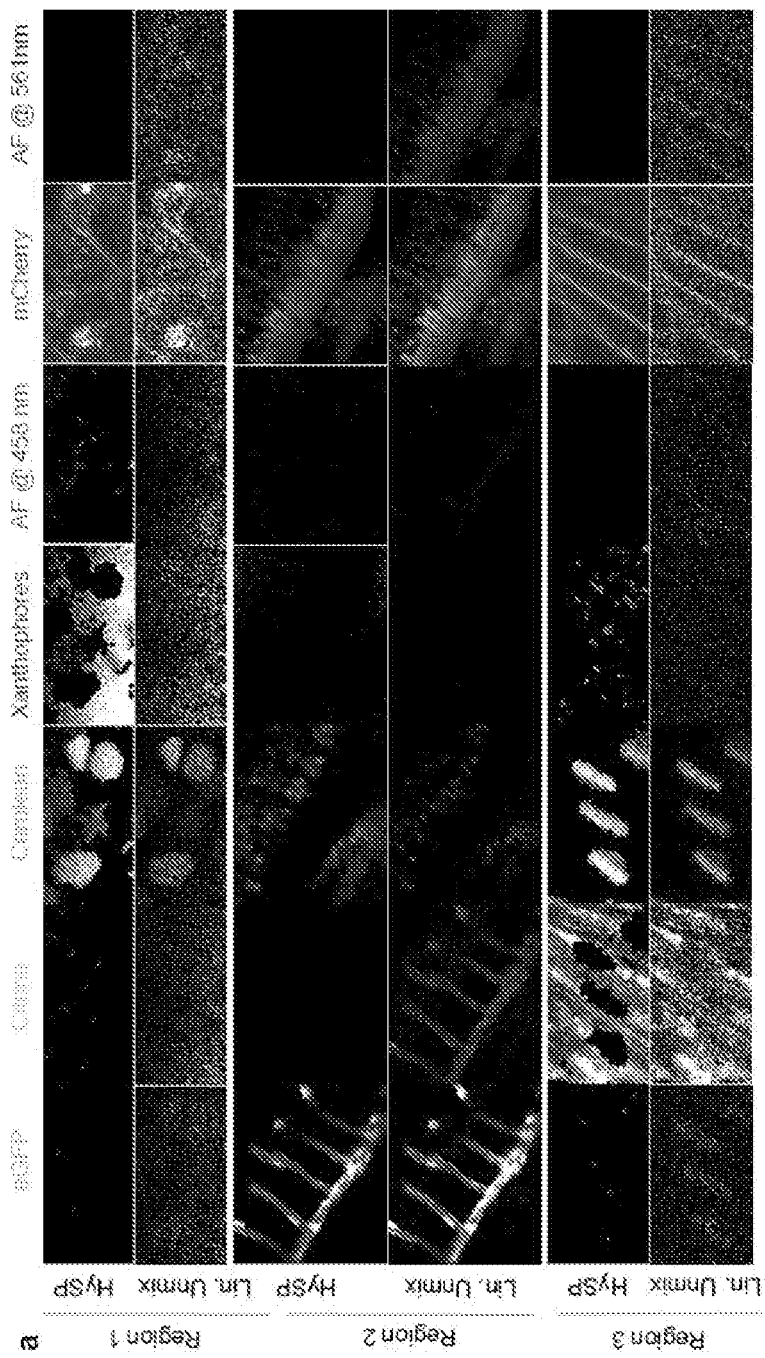
Figure 12B:
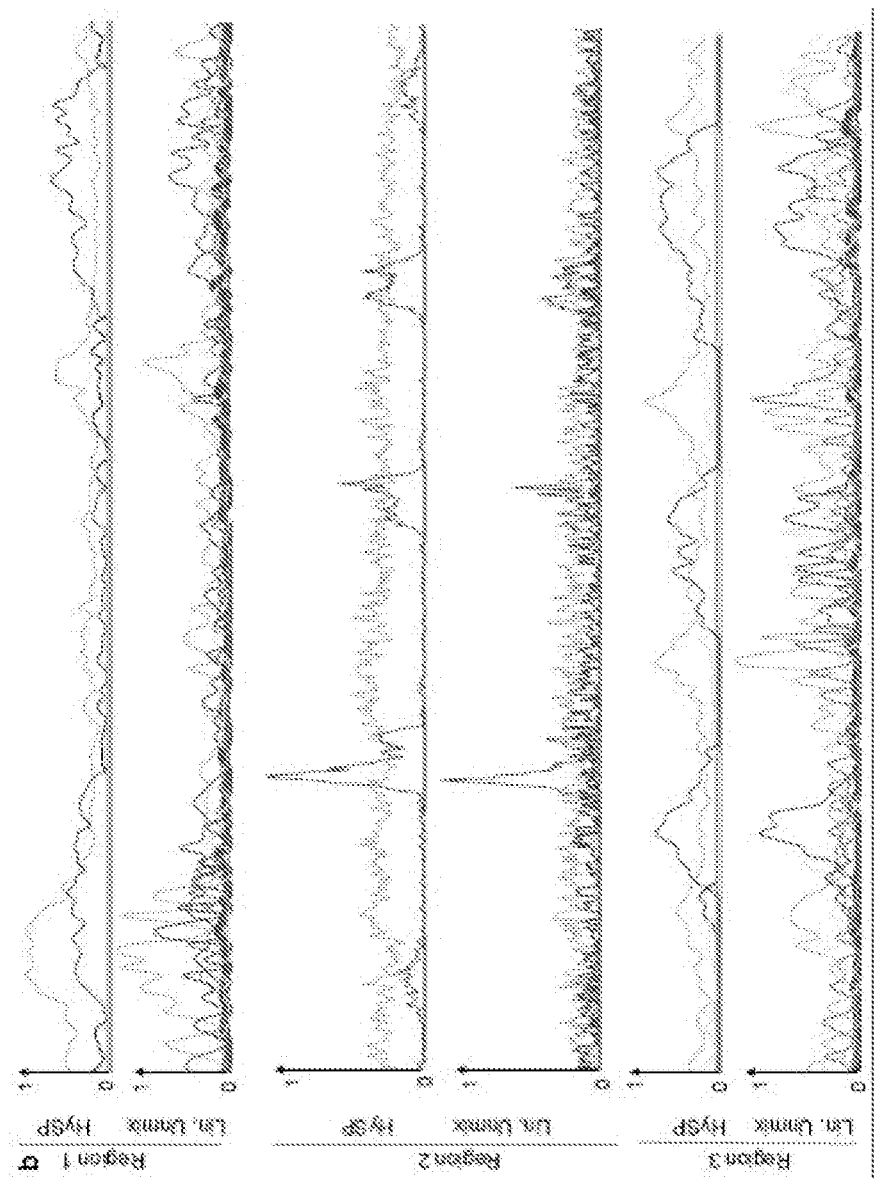

HySP may outperform other conventional multispectral approaches: optical filter separation and linear unmixing [4,6]. Conventional optical separation, due to the problem of signal bleed-through (FIGS. 6b,e,f; and 7), may yield low signal-to-background ratios (SBR). Linear unmixing may improve SBR significantly. However, HySP may offer superior performance especially in separating multiple colors within the same sample from multiple intrinsic signals (FIGS. 2, 3, 6e,f and 9) at lower SNR (FIG. 11). The reduced amount of signal required may allow for lower laser power and reduced photo-damage in time-lapse imaging. Furthermore, the analysis time for this about 10 Gigabytes dataset (FIG. 2a, Table 3) was about 10 minutes using HySP compared to about 2.5 hours using linear unmixing on the same computer. The simplicity and robustness of phasor approach may provide the potential of using HySP analysis post-acquisition of large samples. The HySP approach may well be poised to be used in the context of live imaging of biological processes in vivo as a solution for analysis of mosaic fluorescent protein expression systems [25-27] with the capability to handle multi-dimensional (x,y,z,λ,t) datasets with computational time in the order of minutes.

This analysis shows the robustness, speed, denoising capability and simplicity of the Hyper-Spectral Phasor representation. It may allow for a robust distinction of spectra, within the bounds of accuracy dictated primarily by the Poissonian noise in data acquisition. Because median filtering may be used to process the spectral data in phasor space without altering the intensity data, it may provide denoised images with substantially uncompromised resolution. The hyperspectral imaging system may be substantially oblivious to the mode of imaging as long as sufficient wavelength bins are available for calculating the Fourier coefficients of the spectral phasor (FIG. 13). These advantages may make HySP applicable in a variety of contexts ranging from time-lapse imaging to cell lineage analysis, from fluorescence microscopy to cultural heritage reflectance imaging, and from emission to excitation multi-spectral data.

Other examples of this disclosure are as follows.

EXAMPLES

Example 1. Zebrafish Lines

Adult fish were raised and maintained as described in [28] and in strict accordance with the recommendations in the Guide for the Care and Use of Laboratory Animals by University of Southern California, where the protocol was approved by the Institutional Animal Care and Use Committee (IACUC) (Permit Number: 12007 USC). Transgenic FlipTrap Gt(desm-citrine)$^{ct122a/+}$ line was obtained from a previously described screen in the lab [23], Tg(kdrkeGFP)$^{s843}$ line [24] was provided by the Stainier lab, and Tg(ubiq:membrane-Cerulean-2a-H2B-tdTomato) line was generated by injecting a construct containing tol2 transposable elements flanking the ubiquitin promoter, coding sequence for membrane localized cerulean, a short sequence encoding the ribosome-skipping peptide of Thosea asigna virus (2a) followed by H2B-tdTomato. Upon crossing appropriate adult lines, the embryos obtained were raised in Egg Water (about 60 µg/ml of Instant Ocean and about 75 µg/ml of CaSO$_4$ in Milli-Q water) at about 28.5° C. with addition of about 0.003% (w/v) 1-phenyl-2-thiourea (PTU) about 18 hpf to reduce pigment formation [28].

Example 2. Sample Preparation and Imaging

About 5 µM fluorescein (F1300, Invitrogen, Carlsbad, Calif.) solution in ethanol was prepared. For imaging, the solution was transferred into a sealed 10 mm glass bottom dish (P35G-1.5-10-c, MatTek Corporation, Ashland, Mass., USA) and mounted in an inverted confocal microscope. Imaging was performed on a Zeiss LSM780 inverted confocal microscope with QUASAR detector (Carl Zeiss, Jena, Germany). A typical dataset consists of 32 images, each of dimensions 512×512 pixels, corresponding to different wavelengths from about 410.5 nm to about 694.9 nm with about 8.9 nm bandwidth. The measurement is repeated 10 times using C-Apochromat 40×/1.20 W Korr Zeiss objective at any given imaging parameter. Fluorescein was imaged with about 488 nm laser at different acquisition parameters (Table 1).

For in vivo imaging 5-6 zebrafish embryos at appropriate stage were placed into about 1% agarose (Catalog No. 16500-100, Invitrogen™) moulds created in an imaging dish with #1.5 coverglass bottom, (Catalog No. D5040P, WillCo Wells) using a custom designed negative plastic mould [29]. Embryos were immobilized by adding about 2 ml of about 1% UltraPure™ Low Melting Point Agarose (Catalog No. 16520-050, Invitrogen™) solution prepared in about 30% Danieau (about 17.4 mM NaCl, about 210 µM KCl, about 120 µM MgSO$_4$.7H$_2$O, about 180 µM Ca(NO$_3$)$_2$, about 1.5 mM HEPES buffer in water, pH about 7.6) with about 0.003% PTU and about 0.01% tricaine. This solution was then added on top of the embryos already placed in the mold. Following solidification of agarose at room temperature (1-2 minutes), the imaging dish was filled with about 30% Danieau solution and about 0.01% Tricaine, at about 28.5° C. Subsequent imaging was performed on an inverted confocal microscope by positioning the petridish appropriately on the microscope stage. Samples were obtained by crossing Gt(desm-citrine)$^{ct122a/+}$ with Tg(kdrl:eGFP) fish for two color imaging. Samples with four fluorescent proteins result from same crossing followed by injection of about 100 pg per embryo of mRNA encoding H2B-cerulean and membrane-mCherry. Samples of Gt(desm-citrine)$^{ct122a/+}$ Tg(kdrl:eGFP) were imaged with about 488 nm laser to excite both Citrine and eGFP and a narrow about 488 nm dichroic to separate excitation and fluorescence emission. Samples of Gt(desm-citrine)$^{ct122a/+}$; Tg(kdrteGFP) with H2B-cerulean and membrane-mCherry labels were imaged with about 458 nm laser to excite Cerulean, eGFP and Citrine with a narrow about 488 nm dichroic, following an about 561 nm laser to excite mCherry with an about 458-561 nm dichroic.

For in vivo time-lapse imaging 5-6 zebrafish at appropriate stage were immobilized in an imaging dish with #1.5 coverglass bottom using about 0.5% Low Melting Point Agarose agarose (same as above) to allow for development and with about 0.003% PTU and about 0.01% tricaine. Subsequent imaging was performed on the same confocal-two photon inverted microscope at about 28.5° C. A solution of Egg Water was added every hour to the imaging dish to ensure proper hydration of the sample. Samples with five fluorescent proteins were obtained by crossing Tg(kdrl:eGFP) with Tg(ubiq:membrane-Cerulean-2a-H2B-tdTomato) zebrafish followed by injection of about 120 pg and about 30 pg per embryo of mRNA encoding Rab9-YFP and Rab11-mCherry, respectively. Volumetric data was acquired using about 950 nm to excite Cerulean, eGFP, YFP and (weakly) tdTomato with a 760+ bandpass filter, following an about 561 nm laser to excite mCherry and tdTomato with an about 458-561 nm dichroic.

Table 3 provides the detailed description of the imaging parameters used for all images presented in this work.

Example 3. Phasor Analysis

Transform:

For each pixel in a dataset, the Fourier coefficients of its normalized spectra define the coordinates of its phasor point ($z(n)$):

$$z(n) = G(n) + iS(n), \quad \text{Equation (1)}$$

where 
$$G(n) = \frac{\sum_{\lambda s}^{\lambda f} I(\lambda)\cos(n\omega\lambda)\Delta\lambda}{\sum_{\lambda s}^{\lambda f} I(\lambda)\Delta\lambda} \text{ and }$$

$$S(n) = \frac{\sum_{\lambda s}^{\lambda f} I(\lambda)\sin(n\omega\lambda)\Delta\lambda}{\sum_{\lambda s}^{\lambda f} I(\lambda)\Delta\lambda}$$

where $\lambda s$ and $\lambda f$ are starting and ending wavelengths respectively; $I$ is the intensity; $\omega = 2\pi/\tau s$ with $\tau s$=number of spectral channels (e.g. 32) and n is the harmonic (e.g. 2).

Scatter Error on Phasor Plot:

Scatter error is inversely proportional to square root of number of photons N:

$$std\{z(n)\} \propto \frac{|z(n)|}{\sqrt{N}} \quad \text{Equation (2)}$$

This proportionality has been derived as follows. We define the recorded total signal intensity (digital counts, obtained by area under the spectral curve) as a measure of N with the assumption that the number of digital levels detected in confocal analog mode is proportional to the number of photons collected [20]. This implies:

$$E_{\Delta s}^{\lambda f} I(\lambda)\Delta\lambda \propto N. \quad \text{Equation (3)}$$

Based on Equation 1 and by propagation of statistical errors we know that, $$std\{G(n)\} = \quad \text{Equation (4)}$$

$$G(n)\sqrt{\frac{\text{Var}\left\{\sum_{\lambda s}^{\lambda f} I(\lambda)\cos(n\omega\lambda)\Delta\lambda\right\}}{\left[\sum_{\lambda s}^{\lambda f} I(\lambda)\cos(n\omega\lambda)\Delta\lambda\right]^2} + \frac{\text{Var}\left\{\sum_{\lambda s}^{\lambda f} I(\lambda)\Delta\lambda\right\}}{\left[\sum_{\lambda s}^{\lambda f} I(\lambda)\cos\Delta\lambda\right]^2}}$$

where std and Var denote standard deviation and variance respectively. This can be further simplified as:

$$std\{G(n)\} \propto G(n)\sqrt{\frac{\sum_{\lambda s}^{\lambda f} \text{Var}\{I(\lambda)\}\cos^2(n\omega\lambda)}{G(n)N^2} + \frac{N}{N^2}} ; \quad \text{Equation (5)}$$

as std{digital counts} CON:

$$std\{G(n)\} \propto \sqrt{\frac{\sum_{\lambda s}^{\lambda f} \text{Var}\{I(\lambda)\}\cos^2(n\omega\lambda)}{N^2} + \frac{G(n)^2}{N}} \quad \text{Equation (6)}$$

From the above, we can see that the second term dominates and therefore we have:

$$std\{G(n)\} \propto \frac{G(n)}{\sqrt{N}} \quad \text{Equation (7)}$$

Similarly:

$$std\{S(n)\} \propto \frac{S(n)}{\sqrt{N}} \quad \text{Equation (8)}$$

Therefore:

$$std\{z(n)\} \propto \frac{|z(n)|}{\sqrt{N}} \quad \text{Equation (9)}$$

Shifted-Mean Error on Phasor Plot:

Based on the expected value ($z_e(n)$) and the true representation of a spectrum ($z_0(n)$), we can write:

$$|z_e - z_0| = \sqrt{|\langle G_e \rangle - \langle G_o \rangle|^2 + |\langle S_e \rangle - \langle S_o \rangle|^2} \quad \text{Equation }\langle 10\rangle$$

where $\langle . \rangle$ denotes the average values used to compute the respective quantities. This expression is defined as shifted-mean error. Further:

$$|z_e - z_0| = \sqrt{|z_e|^2 + |z_0|^2 - 2|z_e||z_0|\cos(\Delta\varphi)} = \quad \text{Equation (11)}$$

$$|z_0|\sqrt{1 + \frac{|z_e|^2}{|z_0|^2} - 2\frac{|z_e|}{|z_0|}\cos(\Delta\varphi)}$$

where $\Delta\varphi$ is the phase difference between the two phasor points. It can be seen from above that the shifted-mean error remains bound as:

$$||z_e|-|z_0|| \le |z_e - z_0| \le \sqrt{|z_e|^2 + |z_0|^2} \quad \text{Equation (12)}$$

Further we can also define a normalized shifted-mean error as defined as follows:

$$\frac{|z_e - z_0|}{z_0} = \sqrt{1 + \frac{|z_e|^2}{|z_0|^2} - 2\frac{|z_e|}{|z_0|}\cos(\Delta\varphi)} \quad \text{Equation (13)}$$

In this analysis the dataset is acquired with about 177 μs pixel dwell time at about 850 gain and about 21% laser power as the true representation of Fluorescein spectrum owing to its low value of scatter error. However, the general conclusions about the behavior of shifted-mean error remains the same irrespective of the value of $z_0(n)$.

Harmonic Number in Phasor Analysis:

Typically, phasor plots have been limited to using the first harmonic or the second harmonic of the Fourier representation of the spectral profile to determine the spectral signatures. This may be due to the presence of branch points in the Riemannian surfaces in complex plane corresponding to representations of harmonics greater than 2 that may not be easy to visualize. Based on Equation 1 we calculated residuals (p(n)) as the ratio of the absolute sum of all Fourier coefficients except the one corresponding to the harmonic number (n) of choice, to the absolute value of the $n^{th}$ Fourier coefficient. Therefore:

$$\rho(n) = \frac{\sum_{i=0, i \neq n}^{N} (\langle S_i \rangle^2 + \langle G_i \rangle^2)}{\langle S_n \rangle^2 + \langle G_n \rangle^2} \quad \text{Equation (14)}$$

Figure 5F:
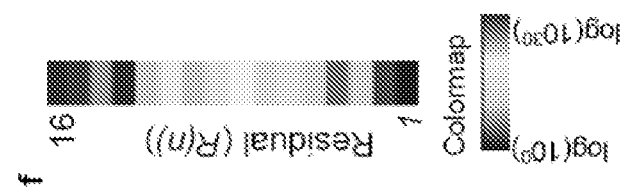

For typical fluorescent spectra, such as the Fluorescein emission spectrum here, 1 and 2 remain the dominant harmonic numbers, as the residuals for these are at least an order of magnitude smaller than the residuals for other harmonics (FIG. 5f). Further the fluctuations in residual values may be dependent on the exact nature of the spectrum being analyzed. However, such an approach may be easy to implement every time phasor analysis is done and may allow a quick verification of the choice of the harmonic number used for any recorded spectrum.

Example 4. Denoising

For any image of a given size (n×m pixels), S and G values are obtained for every pixel, yielding 2 new 2D matrices, for S and G, with dimensions n×m. Upon filtering of these two matrices, with new values S* and G*, may be obtained for every pixel. Since the initial S and G matrices had the same indices as the pixels in the image, the filtered matrices S* and G*, therefore, preserve the geometrical information.

Fluorescein data were analyzed using Matlab scripts utilizing the equations disclosed above. Large zebrafish microscopy datasets were recorded by using the hyperspectral imaging system as disclosed above. Linear Unmixing was done by using Zen Software (Zeiss, Jena, Germany).

Any combination of above features/configurations is within the scope of this disclosure.

The components, steps, features, objects, benefits, and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and/or advantages. These also include embodiments in which the components and/or steps are arranged and/or ordered differently.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases from a claim means that the claim is not intended to and should not be interpreted to be limited to these corresponding structures, materials, or acts, or to their equivalents.

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element proceeded by an "a" or an "an" does not, without further constraints, preclude the existence of additional elements of the identical type.

None of the claims are intended to embrace subject matter that fails to satisfy the requirement of Sections 101, 102, or 103 of the Patent Act, nor should they be interpreted in such a way. Any unintended coverage of such subject matter is hereby disclaimed. Except as just stated in this paragraph, nothing that has been stated or illustrated is intended or should be interpreted to cause a dedication of any component, step, feature, object, benefit, advantage, or equivalent to the public, regardless of whether it is or is not recited in the claims.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

The invention claimed is:

1. A hyperspectral imaging system for generating an unmixed color image of a target, comprising:
   an optics system; and
   an image forming system;
   wherein:
      the optics system comprises at least one optical component;
      the at least one optical component comprises at least one optical detector;
      the at least one optical detector has a configuration that:
         detects electromagnetic radiation absorbed, transmitted, refracted, reflected, and/or emitted ("target radiation") by at least one physical point on the target, the target radiation comprises at least two waves ("target waves"), each wave having an intensity and a different wavelength;

detects the intensity and the wavelength of each target wave; and transmits the detected target radiation, and the detected intensity and wavelength of each target wave to the image forming system;

the image forming system comprises a control system, a hardware processor, a memory, and a display; and the image forming system has a configuration that:

forms an image of the target using the detected target radiation ("target image"), wherein the target image comprises at least two pixels, and wherein each pixel corresponds to one physical point on the target;

forms at least one spectrum for each pixel using the detected intensity and wavelength of each target wave ("intensity spectrum");

transforms the formed intensity spectrum of each pixel using a Fourier transform into a complex-valued function based on the intensity spectrum of each pixel, wherein each complex-valued function has at least one real component and at least one imaginary component;

applies a denoising filter on both the real component and the imaginary component of each complex-valued function at least once so as to produce a denoised real value and a denoised imaginary value for each pixel;

forms one point on a phasor plane ("phasor point") for each pixel by plotting the denoised real value against the denoised imaginary value of each pixel;

maps back the phasor point to a corresponding pixel on the target image based on the phasor point's geometric position on the phasor plane;

assigns an arbitrary color to the corresponding pixel based on the geometric position of the phasor point on the phasor plane;

generates an unmixed color image of the target based on the assigned arbitrary color; and displays the unmixed color image of the target on the image forming system's display.

2. The hyperspectral imaging system of claim 1, wherein the at least one optical component further comprises at least one source to illuminate the target ("illumination source"), and wherein the illumination source generates an electromagnetic radiation ("illumination source radiation") that comprises at least one wave ("illumination wave").

3. The hyperspectral imaging system of claim 1, wherein the hyperspectral imaging system further comprises at least one illumination source, wherein the illumination source generates an illumination source radiation that comprises at least two illumination waves, and wherein each illumination wave has a different wavelength.

4. The hyperspectral imaging system of claim 2, wherein the at least one optical component further comprises an optical lens, an optical filter, a dispersive optic system, or a combination thereof.

5. The hyperspectral imaging system of claim 3, wherein the at least one optical component further comprises an optical lens, an optical filter, a dispersive optic system, or a combination thereof.

6. The hyperspectral imaging system of claim 2, wherein the at least one optical component further comprises an optical lens, an optical filter, a dispersive optic system, or a combination thereof; and wherein the optical components of the hyperspectral imaging system are configured to form a microscope.

7. The hyperspectral imaging system of claim 3, wherein the at least one optical component further comprises an optical lens, an optical filter, a dispersive optic system, or a combination thereof; and wherein the optical components of the hyperspectral imaging system are configured to form a microscope.

8. The hyperspectral imaging system of claim 6, wherein the optical components of the hyperspectral imaging system are configured to form a confocal fluorescence microscope, a two-photon fluorescence microscope, or a combination thereof.

9. The hyperspectral imaging system of claim 7, wherein the optical components of the hyperspectral imaging system are configured to form a confocal fluorescence microscope, a two-photon fluorescence microscope, or a combination thereof.

10. The hyperspectral imaging system of claim 2, wherein the at least one optical component further comprises a first optical lens, a second optical lens, and a dichroic mirror/beam splitter.

11. The hyperspectral imaging system of claim 3, wherein the at least one optical component further comprises a first optical lens, a second optical lens, and a dichroic mirror/beam splitter.

12. The hyperspectral imaging system of claim 2, wherein the at least one optical component further comprises an optical lens; and a dispersive optic and wherein at least one optical detector is an optical detector array.

13. The hyperspectral imaging system of claim 3, wherein the at least one optical component further comprises an optical lens; and a dispersive optic and wherein at least one optical detector is an optical detector array.

14. The hyperspectral imaging system of claim 2, wherein the at least one optical component further comprises an optical lens, a dispersive optic, and a dichroic mirror/beam splitter; and
wherein at least one optical detector is an optical detector array.

15. The hyperspectral imaging system of claim 3, wherein the at least one optical component further comprises an optical lens, a dispersive optic, and a dichroic mirror/beam splitter; and
wherein at least one optical detector is an optical detector array.

16. The hyperspectral imaging system of claim 2, wherein the at least one optical component further comprises an optical lens, a dispersive optic, and a dichroic mirror/beam splitter;
wherein at least one optical detector is an optical detector array; and wherein the illumination source directly illuminates the target.

17. The hyperspectral imaging system of claim 3, wherein the at least one optical component further comprises an optical lens, a dispersive optic, and a dichroic mirror/beam splitter;
wherein at least one optical detector is an optical detector array; and wherein the illumination source directly illuminates the target.

18. The hyperspectral imaging system of claim 1, wherein the image forming system uses at least one harmonic of the Fourier transform to generate the unmixed color image of the target.

19. The hyperspectral imaging system of claim 1, wherein the image forming system uses at least a first harmonic and/or a second harmonic of the Fourier transform to generate the unmixed color image of the target.

20. The hyperspectral imaging system of claim 1, wherein the image forming system uses only a first harmonic or only a second harmonic of the Fourier transform to generate the unmixed color image of the target.

21. The hyperspectral imaging system of claim 1, wherein the image forming system uses only a first harmonic and only a second harmonic of the Fourier transform to generate the unmixed color image of the target.

22. The hyperspectral imaging system of claim 2, wherein the illumination source illuminates the target at each illumination wavelength by simultaneously transmitting all illumination waves.

23. The hyperspectral imaging system of claim 3, wherein the illumination source illuminates the target at each illumination wavelength by simultaneously transmitting all illumination waves.

24. The hyperspectral imaging system of claim 2, wherein the illumination source illuminates the target at each illumination wavelength by sequentially transmitting each wave.

25. The hyperspectral imaging system of claim 3, wherein the illumination source illuminates the target at each illumination wavelength by sequentially transmitting each wave.

26. The hyperspectral imaging system of claim 1, wherein the target radiation comprises an electromagnetic radiation emitted by the target.

27. The hyperspectral imaging system of claim 1, wherein the target radiation comprises an electromagnetic radiation emitted by the target; and wherein the electromagnetic radiation emitted by the target comprises luminescence.

28. The hyperspectral imaging system of claim 1, wherein the target radiation comprises an electromagnetic radiation emitted by the target; wherein the electromagnetic radiation emitted by the target comprises luminescence; and wherein the luminescence comprises fluorescence, phosphorescence, or a combination thereof.

29. The hyperspectral imaging system of claim 1, wherein the target radiation comprises an electromagnetic radiation emitted by the target, and wherein the electromagnetic radiation emitted by the target comprises thermal radiation.

30. The hyperspectral imaging system of claim 1, wherein the target radiation comprises an electromagnetic radiation emitted by the target; and wherein the electromagnetic radiation emitted by the target comprises luminescence, thermal radiation, or a combination thereof.

31. The hyperspectral imaging system of claim 1, wherein the target radiation comprises an electromagnetic radiation emitted by the target; wherein the electromagnetic radiation emitted by the target comprises luminescence, thermal radiation, or a combination thereof; and
wherein the luminescence comprises fluorescence, phosphorescence, or a combination thereof.

32. The hyperspectral imaging system of claim 1, wherein the target radiation comprises an electromagnetic radiation emitted by the target; and wherein the electromagnetic radiation emitted by the target comprises fluorescence.

33. The hyperspectral imaging system of claim 1, wherein the at least one optical component further comprises an optical filtering system; wherein the target radiation comprises an electromagnetic radiation emitted by the target; and wherein the electromagnetic radiation emitted by the target comprises fluorescence.

34. The hyperspectral imaging system of claim 1, wherein the at least one optical component further comprises an optical filtering system placed between the target and the at least one optical detector; wherein the target radiation comprises an electromagnetic radiation emitted by the target; and wherein the electromagnetic radiation emitted by the target comprises fluorescence.

35. The hyperspectral imaging system of claim 1, wherein:
the at least one optical component further comprises an optical filtering system placed between the target and the at least one optical detector;
the optical filtering system comprises a dichroic filter, a beam splitter type filter, or a combination thereof;
the target radiation comprises an electromagnetic radiation emitted by the target; and
the electromagnetic radiation emitted by the target comprises fluorescence.

36. The hyperspectral imaging system of claim 1, wherein the at least one optical component further comprises a first optical filtering system and a second optical filtering system; wherein:
the first optical filtering system is placed between the target and the at least one optical detector;
the second optical filtering system is placed between the first optical filtering system and the at least one optical detector;
the first optical filtering system comprises a dichroic filter, a beam splitter type filter, or a combination thereof;
the second optical filtering system comprises a notch filter, an active filter, or a combination thereof;
the target radiation comprises an electromagnetic radiation emitted by the target; and
the electromagnetic radiation emitted by the target comprises fluorescence.

37. The hyperspectral imaging system of claim 1, wherein the at least one optical component further comprises a first optical filtering system and a second optical filtering system; wherein:
the first optical filtering system is placed between the target and the at least one optical detector;
the second optical filtering system is placed between the first optical filtering system and the at least one optical detector;
the first optical filtering system comprises a dichroic filter, a beam splitter type filter, or a combination thereof;
the second optical filtering system comprises an active filter;
the active filter comprises an adaptive optical system, an acousto-optic tunable filter, a liquid crystal tunable bandpass filter, a Fabry-Perot interferometric filter, or a combination thereof;
the target radiation comprises an electromagnetic radiation emitted by the target; and
the electromagnetic radiation emitted by the target comprises fluorescence.

38. The hyperspectral imaging system of claim 1, wherein the denoising filter comprises a median filter.

39. The hyperspectral imaging system of claim 2, wherein the illumination source comprises a coherent electromagnetic radiation source.

40. The hyperspectral imaging system of claim 3, wherein the illumination source comprises a coherent electromagnetic radiation source.

41. The hyperspectral imaging system of claim 2, wherein the illumination source comprises a coherent electromagnetic radiation source, and the coherent electromagnetic radiation source comprises a laser, a diode, a two-photon excitation source, a three-photon excitation source, or a combination thereof.

42. The hyperspectral imaging system of claim 3, wherein the illumination source comprises a coherent electromagnetic radiation source, and the coherent electromagnetic radiation source comprises a laser, a diode, a two-photon excitation source, a three-photon excitation source, or a combination thereof.

43. The hyperspectral imaging system of claim 1, wherein the at least one detector comprises a photomultiplier tube, a photomultiplier tube array, a digital camera, a hyperspectral camera, an electron multiplying charge coupled device, a Sci-CMOS, or a combination thereof.

44. The hyperspectral imaging system of claim 1, wherein the target radiation comprises at least four wavelengths.

45. The hyperspectral imaging system of claim 1, wherein the target comprises a target comprising an organic compound.

46. The hyperspectral imaging system of claim 1, wherein the target comprises a target comprising an organic compound; and wherein the target comprises a tissue, a fluorescent genetic label, or a combination thereof.

47. The hyperspectral imaging system of claim 1, wherein the hyperspectral imaging system forms the unmixed color image of the target at a signal-to-noise ratio of the at least one spectrum in the range of 1.2 to 50.

48. The hyperspectral imaging system of claim 1, wherein the hyperspectral imaging system forms the unmixed color image of the target at a signal-to-noise ratio of the at least one spectrum in the range of 2 to 50.

49. The hyperspectral imaging system of claim 1, wherein the at least one optical detector detects the electromagnetic radiation emitted by the target at a wavelength in the range of 300 nm to 800 nm.

50. The hyperspectral imaging system of claim 1, wherein the at least one optical detector detects the electromagnetic radiation emitted by the target at a wavelength in the range of 300 nm to 800 nm; and wherein the electromagnetic radiation emitted by the target comprises fluorescence.

51. The hyperspectral imaging system of claim 2, wherein the illumination source radiation comprises an illumination wave with a wavelength in the range of 300 nm to 1,300 nm.

52. The hyperspectral imaging system of claim 3, wherein the illumination source radiation comprises an illumination wave with a wavelength in the range of 300 nm to 1,300 nm.

53. The hyperspectral imaging system of claim 2, wherein the at least one illumination source comprises a one-photon excitation source; and wherein the illumination source radiation comprises an illumination wave with a wavelength in the range of 300 nm to 700 nm.

54. The hyperspectral imaging system of claim 3, wherein the at least one illumination source comprises a one-photon excitation source; and wherein the illumination source radiation comprises an illumination wave with a wavelength in the range of 300 nm to 700 nm.

55. The hyperspectral imaging system of claim 2, wherein the at least one illumination source comprises a two-photon excitation source; and wherein the illumination source radiation comprises an illumination wave with a wavelength in the range of 690 nm to 1,300 nm.

56. The hyperspectral imaging system of claim 3, wherein the at least one illumination source comprises a two-photon excitation source; and wherein the illumination source radiation comprises an illumination wave with a wavelength in the range of 690 nm to 1,300 nm.

57. The hyperspectral imaging system of claim 2, wherein the at least one illumination source comprises a two-photon excitation source; wherein the two photon excitation source comprises a tunable laser; and wherein the illumination source radiation comprises an illumination wave with a wavelength in the range of 690 nm to 1,300 nm.

58. The hyperspectral imaging system of claim 3, wherein the at least one illumination source comprises a two-photon excitation source; wherein the two photon excitation source comprises a tunable laser; and wherein the illumination source radiation comprises an illumination wave with a wavelength in the range of 690 nm to 1,300 nm.

59. The hyperspectral imaging system of claim 2, wherein the at least one illumination source comprises a one-photon excitation source, a two-photon excitation source, or a combination thereof; wherein the illumination source radiation of the one-photon radiation source comprises an illumination wave with a wavelength in the range of 300 nm to 700 nm; and wherein the illumination source radiation of the two-photon excitation source comprises an illumination wave with a wavelength in the range of 690 nm to 1,300 nm.

60. The hyperspectral imaging system of claim 3, wherein the at least one illumination source comprises a one-photon excitation source, a two-photon excitation source, or a combination thereof; wherein the illumination source radiation of the one-photon radiation source comprises a wave with an illumination wavelength in the range of 300 nm to 700 nm; and wherein the illumination source radiation of the two-photon excitation source comprises an illumination wave with a wavelength in the range of 690 nm to 1,300 nm.

61. The hyperspectral imaging system of claim 1, wherein the image forming system has a configuration that uses a reference material to assign an arbitrary color to each pixel.

62. The hyperspectral imaging system of claim 1, wherein the image forming system has a configuration that uses a reference material to assign an arbitrary color to each pixel, and wherein the unmixed color image of the reference material is generated prior to the generation of an unmixed color image of the target.

63. The hyperspectral imaging system of claim 1, wherein the image forming system has a configuration that uses a reference material to assign an arbitrary color to each pixel, wherein the unmixed color image of the reference material is generated prior to the generation of an unmixed color image of the target, and wherein the reference material comprises a physical structure, a chemical molecule, a biological molecule, a physical change and/or biological change caused by disease, or any combination thereof.

64. The hyperspectral imaging system of claim 1, wherein the image forming system has a configuration that uses a reference material to assign an arbitrary color to each pixel and diagnoses a health condition.

65. The hyperspectral imaging system of claim 1, wherein the image forming system has a configuration that uses a reference material to assign an arbitrary color to each pixel and diagnoses a health condition; and wherein the unmixed color image of the reference material is generated prior to the generation of an unmixed color image of the target.

66. The hyperspectral imaging system of claim 1, wherein image forming system has a configuration that uses a reference material to assign an arbitrary color to each pixel and diagnoses a health condition; wherein the unmixed color image of the reference material is generated prior to the generation of an unmixed color image of the target; and wherein the reference material comprises a physical structure, a chemical molecule, a biological molecule, a physical change and/or biological change caused by disease, or any combination thereof.

67. A hyperspectral imaging system for generating an unmixed color image of a target, comprising:
an image forming system;
wherein the image forming system has a configuration that:
acquires a target radiation comprising at least two target waves, each wave having an intensity and a different wavelength;
forms a target image, wherein the target image comprises at least two pixels, and wherein each pixel corresponds to one physical point on the target;
forms at least one intensity spectrum for each pixel using the intensity and the wavelength of each target wave;
transforms the formed intensity spectrum of each pixel using a Fourier transform into a complex-valued function based on the intensity spectrum of each pixel, wherein each complex-valued function has at least one real component and at least one imaginary component;
applies a denoising filter on both the real component and the imaginary component of each complex-valued function at least once so as to produce a denoised real value and a denoised imaginary value for each pixel;
forms one phasor point for each pixel by plotting the denoised real value against the denoised imaginary value of each pixel;
maps back the phasor point to a corresponding pixel on the target image based on the phasor point's geometric position on the phasor plane;
assigns an arbitrary color to the corresponding pixel based on the geometric position of the phasor point on the phasor plane; and
generates an unmixed color image of the target based on the assigned arbitrary color.

68. A hyperspectral imaging system for generating an unmixed color image of a target, comprising:
an image forming system;
wherein the image forming system has a configuration that:
acquires a target image, wherein the target image comprises at least two pixels, and wherein each pixel corresponds to one physical point on the target;
acquires at least one intensity spectrum for each pixel, wherein the intensity spectrum comprises at least two intensity points;
transforms the intensity spectrum of each pixel using a Fourier transform into a complex-valued function based on the intensity spectrum of each pixel, wherein each complex-valued function has at least one real component and at least one imaginary component;
applies a denoising filter on both the real component and the imaginary component of each complex-valued function at least once so as to produce a denoised real value and a denoised imaginary value for each pixel;
forms one phasor point for each pixel by plotting the denoised real value against the denoised imaginary value of each pixel;
maps back the phasor point to a corresponding pixel on the target image based on the phasor point's geometric position on the phasor plane;
assigns an arbitrary color to the corresponding pixel based on the geometric position of the phasor point on the phasor plane; and
generates an unmixed color image of the target based on the assigned arbitrary color.

69. A hyperspectral imaging system for generating an unmixed color image of a target, comprising:
an optics system; and
an image forming system;
wherein:
the optics system comprises at least one optical detector;
the at least one optical detector has a configuration that:
detects target radiation absorbed, transmitted, refracted, reflected, and/or emitted by at least one physical point on the target, the target radiation comprises at least two target waves, each target wave having an intensity and a different wavelength;
detects the intensity and the wavelength of each target wave; and
transmits the detected target radiation, and each target wave's intensity and wavelength to the image forming system;
the image forming system has a configuration that:
forms a target image, wherein the target image comprises at least two pixels, and wherein each pixel corresponds to one physical point on the target;
forms at least one intensity spectrum for each pixel using the detected intensity and wavelength of each target wave;
transforms the formed intensity spectrum of each pixel using a Fourier transform into a complex-valued function based on the intensity spectrum of each pixel, wherein each complex-valued function has at least one real component and at least one imaginary component;
applies a denoising filter on both the real component and the imaginary component of each complex-valued function at least once so as to produce a denoised real value and a denoised imaginary value for each pixel;
forms one phasor point for each pixel by plotting the denoised real value against the denoised imaginary value of each pixel;
maps back the phasor point to a corresponding pixel on the target image based on the phasor point's geometric position on the phasor plane;
assigns an arbitrary color to the corresponding pixel based on the geometric position of the phasor point on the phasor plane; and
generates an unmixed color image of the target based on the assigned arbitrary color.

* * * * *